United States Patent
Birkett et al.

(10) Patent No.: US 11,207,417 B2
(45) Date of Patent: *Dec. 28, 2021

(54) DRUG-POLYMER CONJUGATE

(71) Applicant: POLYACTIVA PTY LTD, Melbourne (AU)

(72) Inventors: Stephen Lonsdale Birkett, Langwarrin (AT); Andrew Craig Donohue, Bentleigh East (AU); Asha Marina D'Souza, Carnegie (AU); Sarah Man Yee Ng, Berwick (AU); Adrian Sulistio, Glen Iris (AU); Russell John Tait, Balwyn (AU); David Valade, Glenroy (AU); Alan Naylor, Harston (GB); Jason Watling, Gisborne (AU)

(73) Assignee: POLYACTIVA PTY LTD, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/493,258

(22) PCT Filed: Mar. 14, 2018

(86) PCT No.: PCT/AU2018/050233
§ 371 (c)(1),
(2) Date: Sep. 11, 2019

(87) PCT Pub. No.: WO2018/165710
PCT Pub. Date: Sep. 20, 2018

(65) Prior Publication Data
US 2020/0121798 A1    Apr. 23, 2020

Related U.S. Application Data

(63) Continuation-in-part of application No. 15/458,546, filed on Mar. 14, 2017, now Pat. No. 10,113,033.

(30) Foreign Application Priority Data

Mar. 14, 2017   (AU) ................................ 2017900888

(51) Int. Cl.
*A61K 31/5575*    (2006.01)
*A61K 47/50*    (2017.01)
*A61P 27/02*    (2006.01)
*A61K 47/59*    (2017.01)

(52) U.S. Cl.
CPC ........ *A61K 47/593* (2017.08); *A61K 31/5575* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 4,228,152 A | 10/1980 | Ferruti et al. | |
| 5,120,719 A | 6/1992 | Iwamoto et al. | |
| 9,572,892 B2 | 2/2017 | Ng et al. | |
| 10,111,886 B2 | 10/2018 | Ng et al. | |
| 10,113,033 B2* | 10/2018 | Ng .................... | A61K 31/5377 |
| 2010/0104654 A1 | 4/2010 | Robinson et al. | |
| 2011/0319487 A1 | 12/2011 | Mercier | |
| 2014/0120058 A1 | 5/2014 | O'Shea et al. | |
| 2016/0000929 A1* | 1/2016 | Ng .................... | A61K 31/5575 |
| | | | 526/257 |

FOREIGN PATENT DOCUMENTS

| | | |
|---|---|---|
| EP | 0 369 463 A2 | 5/1990 |
| JP | 2004-059439 A | 2/2004 |
| JP | 2013-035802 A | 2/2013 |
| WO | WO-2007/018431 A2 | 2/2007 |
| WO | WO-2010/040187 A1 | 4/2010 |
| WO | WO 2010/040188 A1 | 4/2010 |

(Continued)

OTHER PUBLICATIONS

U.S. Appl. No. 16/493,252, filed Sep. 11, 2019.
Gao et al., "Linear Cationic Click Polymer for Gene Delivery: Synthesis, Biocompatibility, and In Vitro Transfection," Biomacromolecules, vol. 11, No. 11, pp. 3102-3111, Nov. 2010.
Meudtner et al., "Responsive Backbones Based on Alternating Triazole-Pyridine/Benzene Copolymers: From Helically Folding Polymers to Metallosupramolecularly Crosslinked Gels," Macromolecular Rapid Communications, vol. 29, No. 4, pp. 347-351, Feb. 2008.

(Continued)

*Primary Examiner* — Brian Gulledge
(74) *Attorney, Agent, or Firm* — Foley & Lardner LLP

(57) ABSTRACT

A polymer-prostaglandin conjugate comprising: a polymer backbone comprising a plurality of moieties of formula (I): where: T represents a triazole moiety; Q is independently selected at each occurrence and may be present or absent and when present represents a linking group; R is selected from the group consisting of linear or branched hydrocarbon; D is selected from prostaglandins; and L is a group of formula (II) wherein $R^5$ is selected from hydrogen and $C_1$ to $C_6$ alkyl; (R) indicates the end of the group bonded to the R group; and (D) indicates the end of the group attached to the group D.

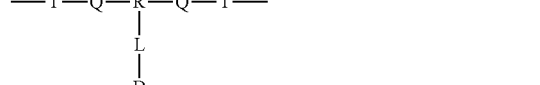

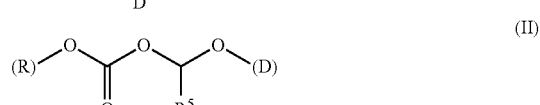

18 Claims, 5 Drawing Sheets

(56) References Cited

FOREIGN PATENT DOCUMENTS

| WO | WO 2010/141507 A1 | 12/2010 | | |
|---|---|---|---|---|
| WO | WO 2012/075117 A2 | 6/2012 | | |
| WO | WO-2012/139164 A1 | 10/2012 | | |
| WO | WO-2014/134689 A1 | 9/2014 | | |
| WO | WO-2014134689 A1 * | 9/2014 | ............. | A61K 47/60 |

OTHER PUBLICATIONS

Efthymiou et al., "Efficient synthesis and cell-based silencing activity of siRNAs that contain triazole backbone linkages," Bioorganic & Medicinal Chemistry Letters, vol. 22, No. 4, pp. 1722-1726, Feb. 2012.

Supplementary European Search Report dated Oct. 20, 2016 in application No. EP 14 76 0322.

International Search Report dated May 26, 2014 in application No. PCT/AU2014/000231.

Gao et al., "Linear Cationic Click Polymers/DNA Nanoparticles: In Vitro Structure—Activity Relationship and In Vivo Evaluation for Gene Delivery," Bioconjugate Chemistry, vol. 22, pp. 1153-1161, May 2011.

International Search Report dated May 17, 2012 in application No. PCT/AU2012/00376.

Miller et al., "Feasibility of Using a 1-4, 7, 8 Bone Targeted, Macromolecular Delivery System Couples with Prostaglandin E1 to Promote Bone Formation in Aged, Estrogen-Deficient Rats," Pharmaceutical Research, vol. 25, No. 12, pp. 2889-2895, (Aug. 2008).

Pan et al., "Proceeding published 2009 by the American Chemical Society: Bone Targeting HPMA Copolymer—Prostaglandin Conjugates", Polymer Preprints, vol. 50, No. 1, pp. 294-295 (Jan. 2009).

Pan et al., "Release of Progstaglandin E 1 from N-(2-Hydroxypropyl)methacrulamide Copolymer Conjugates by Bone Cells," Macromolecular Bioscience, vol. 8, No. 7, pp. 559-605 (Jul. 2008).

Pan et al., "Water-soluble HPMA copolymer-prostaglandin E1 conjugates containing a cathepsin K sensitive spacer," Journal of Drug Targeting, vol. 14, No. 6, pp. 425-435, (Jan. 2006).

Pan et al., "Stability in Plasmas of Various Species of HPMA Copolymer-$PGE_1$ Conjugates," Pharmaceutical Research, vol. 24, No. 12, pp. 2270-2280, (Dec. 2007).

Supplementary European Search Report issued in application No. EP 12 77 0802 dated Sep. 4, 2014.

International Search Report dated May 9, 2018 in application No. PCT/AU2018/050234.

International Search Report dated Apr. 24, 2018 in application No. PCT/AU2018/050233.

* cited by examiner

DRUG-POLYMER CONJUGATE

CROSS-REFERENCE TO RELATED APPLICATIONS

The present application is the U.S. National Stage of International Application No. PCT/AU2018/050233, filed Mar. 14, 2018, which claims priority to Australian Patent Application No. 2017900888, filed Mar. 14, 2017, and U.S. patent application Ser. No. 15/458,546, filed Mar. 14, 2017.

FIELD

The invention relates to a polymer-prostaglandin conjugate, to a monomer-prostaglandin conjugate for use in preparation thereof and to an implant containing the polymer-prostaglandin conjugate.

BACKGROUND

Polymer-drug conjugates containing a drug covalently bound to a polymer are of interest for the targeted and controlled delivery of therapeutic agents. In the treatment of many different conditions, the site-specific delivery of a drug directly to or near a desired site of action in the body of a subject can be highly desirable to improve the efficacy and/or safety of the drug. Certain sites in a subject may require sophisticated delivery vehicles to overcome barriers for effective drug delivery. For example, the eye has a limited volume for administration and requires a pharmaceutical product with a high drug loading to ensure that adequate doses of drug can be delivered while keeping product volume to a minimum. Despite the limited volume it is desirable to be able to deliver drug to the site continuously and in a controlled manner over an extended period of time. Administration to the target site generally involves injection of the product. Consequently it is both an advantage and desirable for the product to biodegrade and disappear at the target site after treatment is provided, obviating the need for removal at the end of therapy. Such removal typically requires surgical intervention.

Prostaglandins and β-blockers used in the treatment of glaucoma are presently formulated as eye drops, which if administered conscientiously to the affected eye will lower intraocular pressure. This in turn can slow the progression of glaucoma. The prostaglandins and β-blockers are administered as eye drops, either alone (i.e. as a single agent) or in combination. It is postulated that combining prostaglandins with β-blockers that exert their effect through a different mechanism, may provide an additive effect in reducing intraocular pressure. For example, some pharmaceutical preparations used in the treatment of glaucoma, such as Xalacom™ eye drops marketed by Pfizer and Ganfort™ eye drops marketed by Allergan, contain a prostaglandin in combination with a β-blocker.

Unfortunately, as glaucoma is an asymptomatic disease many patients do not use their drops conscientiously, compromising therapy. A recent study by Friedman et al. (Friedman et al. *IOVS* 2007:48, 5052-5057) showed that adherence to glaucoma treatment options is poor with only 59% of patients in possession of an ocular hypotensive agent at 12 months, and only 10% of patients used such medication continuously. Patient compliance in glaucoma therapy is therefore an issue.

Unfortunately, as ocular surgery is more prevalent in the elderly many patients do not have the drop competence to administer their drops effectively, compromising therapy. A recent study by An et al showed that drop competence in the elderly is poor with only 7.4% of patients capable of administering their drops effectively following cataract surgery (An J A, Kasner O, Samek D A, Levesque V. *Evaluation of eye drop administration by inexperienced patient after cataract surgery*. J Cataract Refract Surg. 2014; 40:1857-1861). Drop competence in post-surgical drop therapy is therefore an issue.

Drug delivery systems have been developed to aid in the administration and/or sustained delivery of agents (such as drugs) to a desired site of action. One mode of delivering a drug to a subject involves the use of a polymer in association with the drug so that it can be delivered to and/or retained at a specific location.

One form of a polymer/drug delivery system utilises an admixture of a polymer with a drug, where the drug is blended with the polymer matrix. However, such admixtures generally result in poor control over the release of the drug, with a "burst effect" often occurring immediately after administration and significant changes in the physical properties of the admixture occurring as the drug is released (Sjoquist, B.; Basu, S.; Byding, P.; Bergh, K.; Stjernschantz, J. *Drug Metab. Dispos.* 1998, 26, 745). In addition, such admixtures have limited dose loading capacity, resulting in a prohibitively large device for convenient administration to some sites in a subject.

Another form of a polymer/drug delivery system is based on the polymerisation of a drug so as to incorporate the drug molecule as part of the backbone of a polymer chain. Such a system is described in U.S. Pat. No. 6,613,807, WO2008/128193, WO94/04593 and U.S. Pat. No. 7,122,615. However, such polymer systems generally provide inefficient delivery of the drug, as release of the drug relies on breakdown of the polymer backbone. Furthermore, breakdown of the polymer backbone produces inactive intermediates. Such intermediates can complicate regulatory approval, which may require the safety of the intermediates to be demonstrated.

Another approach for preparing polymer-drug conjugates involves the covalent attachment of drug molecules to a pre-formed polymer backbone. Examples of such polymer conjugates have been reviewed in *Nature Reviews: Drug Discovery* 2003:2, 347-360. However, this approach can also be problematic. In particular, steric and thermodynamic constraints can affect the amount of drug that can be covalently attached, and also impact on the distribution of the drug along the polymer backbone. These factors can, in turn, reduce control over the release of the drug. Furthermore, the use of a pre-formed polymer backbone provides limited scope for modification of the polymer conjugate after attachment of the drug, should the properties of the conjugate need to be adjusted to improve drug release and/or to aid patient comfort, particularly in the eye.

In preparing polymer-drug conjugates, step-growth polymerisation is one approach that has been used. By means of step-growth polymerisation, polymer-drug conjugates can be prepared by covalently reacting a drug-functionalised monomer having at least two terminal reactive functional groups, with a co-monomer of complementary terminal functionality. An example is the reaction of a drug-functionalised dihydroxy monomer with a diisocyanate co-monomer to form a drug-polymer conjugate with a polyurethane polymer backbone. However, one problem with step-growth polymerisation methods is that many drug molecules can contain multiple functional groups that are capable of participating in the covalent reactions used to form the polymer. In such circumstances, there is a risk that a functional group on a drug molecule could react with a terminal functional group of a monomer, leading to intra-chain incorporation of the drug in the polymer. As a result, the drug becomes part of the polymer backbone structure, rather than forming a pendant group. Prostaglandins are drugs with multiple nucleophilic functional groups with a consequential high risk of in-chain incorporation.

It would be desirable to provide new polymer-drug conjugates, which address or ameliorate one or more disadvantages or shortcomings associated with existing materials and/or their method of manufacture, or to at least provide a useful alternative to such materials and their method of manufacture.

SUMMARY

In one aspect the invention provides a polymer-prostaglandin conjugate comprising:
a polymer backbone comprising a plurality of moieties of formula (I):

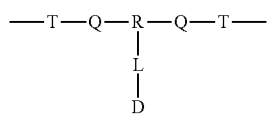

where:
T represents a triazole moiety;
Q is independently selected at each occurrence and may be present or absent and when present represents a linking group;
R is selected from the group consisting of linear or branched hydrocarbon;
D is selected from prostaglandins; and
L is a group of formula (II)

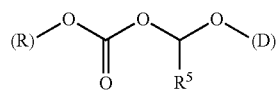

wherein R5 is selected from hydrogen and $C_1$ to $C_6$ alkyl;
(R) indicates the end of the group bonded to the R group; and
(D) indicates the end of the group attached to the group D.

The polymer-prostaglandin conjugate may include functional groups which facilitate biodegradation. In one embodiment the group Q provides biodegradable groups and a preferred embodiment of formula I for provision biodegradable backbone is of formula Ia

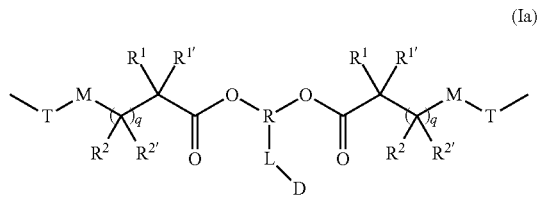

wherein
$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N(R$^w$)—($C_1$ to $C_{10}$ straight or branched chain aliphatic) and an amine linking group comprising $C_1$ to $C_{10}$ straight or branched chain aliphatic interrupted by the group N(R$^w$) wherein R$^w$ is selected from hydrogen and $C_1$ to $C_4$ alkyl;

q is 0 or 1;
R is selected from the group consisting of linear or branched hydrocarbon;
D is selected from prostaglandins;
L is the linker group of formula II

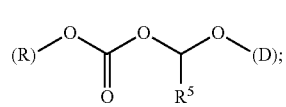

wherein $R^5$ is selected from hydrogen and $C_1$ to $C_6$ alkyl;
(R) indicates the end of the group bonded to the R group; and
(D) indicates the end of the group attached to the group D and
T is a triazole moiety.

Biodegradation of the backbone may allow clearance of the polymer from the site of use such as the eye. In some circumstances it is desirable for the polymer to remain at the site of use for a period to facilitate controlled release of the prostaglandin in the target tissue prior to degradation of the polymer backbone and clearance of the polymer and drug from the site of use.

Biodegradability is controlled by the presence of one of more substituents in the backbone and control of degradation is generally enhanced where at least one of $R^1$, $R^{1'}$, $R^2$, $R^{2'}$ present in the polymer is not hydrogen. For example, at least one of $R^1$ and $R^{1'}$ may be other than hydrogen and/or at least one of $R^2$ and $R^{2'}$ may be other than hydrogen.

The prostaglandin may be covalently bonded to the linker L via a range of position on the prostaglandin including the 1, 9, 11 or 15-positions of the prostaglandin. The effectiveness of the prostaglandin and release generally favours covalent linking at the 1-position of the prostaglandin. In this set of embodiments the drug D in Formula I and Formula Ia is generally of Formula Xb:

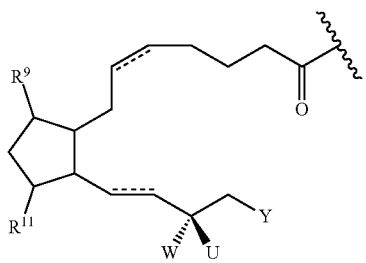

wherein:
〰️ represents the point of attachment of the prostaglandin to L;
----- represents a double or single bond;
Y is optionally substituted $C_4$ to $C_{10}$ hydrocarbyl or optionally substituted $C_4$ to $C_{10}$ hydrocarbyloxy;
$R^9$ and $R^{11}$ are hydroxy; and
W is hydroxy and U is hydrogen, or W and U are both fluoro, or W and U together form oxo.

The polymer-prostaglandin conjugate is generally obtainable as a copolymer of at least one monomer of formula (IV):

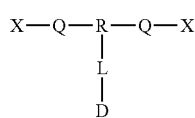

where:
X may be the same or different at each occurrence and represents a terminal functional group comprising an alkyne or an azide;
Q is independently selected at each occurrence and may be present or absent and when present, represents a linking group;
R is selected from the group consisting of linear or branched hydrocarbon, optionally substituted aryl and optionally substituted heteroaryl;
D is a prostaglandin;
L is a group of formula

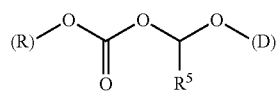

wherein $R^5$ is selected from hydrogen and $C_1$ to $C_6$ alkyl;
(R) indicates the end of the group bonded to the R group; and
(D) indicates the end of the group attached to the group D; and
a monomer of formula (V):

$$Z\text{-}(A)_n \qquad (V)$$

where:
A may be the same or different at each occurrence and represents a group comprising a terminal functional group comprising an alkyne or an azide functionality, wherein said terminal functional group is complementary to the terminal functional group X of formula (IV);
Z is an optionally substituted linker group; and
n is an integer and is at least 2, such as 2 to 8 or 3 to 8.

In the preferred embodiment the polymer-prostaglandin conjugate is obtainable as a copolymer wherein the monomer of Formula IV is of Formula IVa

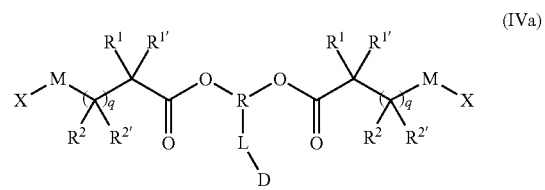

wherein
M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1;
X is a terminal functional group comprising an alkyne or an azide;
R is selected from the group consisting of linear or branched hydrocarbon;
D is selected from prostaglandins;
L is a linker group of formula II

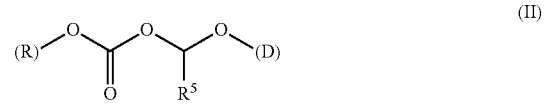

where (R) and (D) show the ends of the linker attached to respective groups and $R^5$ is selected from hydrogen and $C_1$ to $C_6$ alkyl; and the co-monomer of Formula V has the formula Va $$J\text{-}(Y\text{-}A)_n \qquad Va$$

J represents a linking functional group,
n is 2 to 8;
Y comprises a chain of one or more groups selected from the group consisting of polyether, optionally substituted straight or branched $C_1$ to $C_{10}$ alkylene, amino ester, amide, carbonate and carbamate;
A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (IVa);
wherein in the monomers of formula (IVa), the groups $R^1$, $R^{1'}$, $R^2$, $R^{2'}$, are independently selected from the group consisting of hydrogen, alkyl, alkoxy, alkoxy-alkyl, amino, alkyl amino, dialkylamino, amino-alkyl, alkylamino-alkyl, dialkylamino-alkyl and wherein one of the pairs of $R^1,R^{1'}$ and $R^2,R^{2'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl.

In one set of embodiments the comonomer of Formula Va is of Formula Vb

  (Vb)

wherein
A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (IVa);
J represents a linking functional group,
$R^a$ is selected from ethylene, propylene, butylene and mixtures thereof;
m is 1 to 300;
n is 2 to 8;
B is a bond, oxygen, the group of formula -MOC(O)N(H)M'-,-, -MOC(O)OM'-MC(O)NHM'-, the group formula (VIa) or the group of formula (VIb)

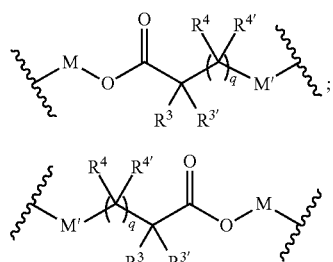 (VIa)

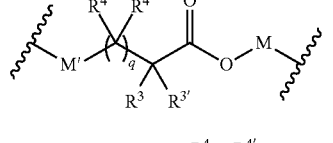 (VIb)

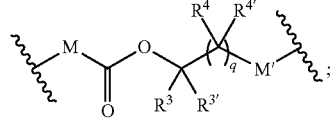 (VIc)

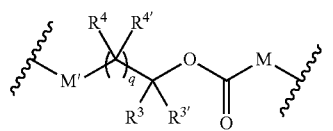 (VId)

M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1; and
wherein in the monomers of formula (IVa), (Va) and (Vb) the groups $R^1$, $R^{1'}$, $R^2$, $R^{2'}$, $R^3$, $R^{3'}$, $R^4$ and $R^{4'}$ are independently selected from the group consisting of hydrogen, alkyl, alkoxy, alkoxy-alkyl, amino, alkyl amino, dialkylamino, amino-alkyl, alkylamino-alkyl, dialkylamino-alkyl and wherein one of the pairs of $R^1,R^{1'}$ and $R^2,R^{2'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl; and wherein one of the pairs of $R^3,R^{3'}$, $R^4,R^{4'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl.

The present of one or more of (VIa), (VIb), (Vic) or (Vid) introduces a further site of biodegradation which may be regulated where at least one of $R^3$, $R^{3'}$, $R^4$ and $R^{4'}$ is other than hydrogen.

The retention of the polymer at the site of use during release of the prostaglandin is further facilitated when the polymer backbone is branched or forms a network. The formation of a branched or network polymer backbone may in a preferred set of embodiment from the use of a monomer of Formula Va or Vb wherein n is 3 or more such as from 3 to 8.

The polymer-prostaglandin conjugate may be in the form of a polymer network comprising network segments of formula (XXX):

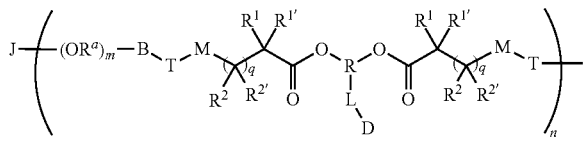 (XXX)

wherein
J represents a linking functional group, preferably an optionally substituted hydrocarbon or hydrocarbon ether or polyether of from $C_2$ to $C_4$ hydrocarbon units;
$R^a$ at each occurrence may be ethylene, propylene or butylene;
m is from 1 to 300;
n is 2 to 8, preferably 3 to 8, particularly 3 or 4;
B is a bond, oxygen, the group of formula -MOC(O)N(H)M'-,-, -MOC(O)OM'-MC(O)NHM'-, the group formula (VIa), (VIb), (VIc) or (VId):

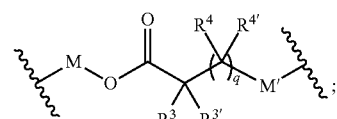 (VIa)

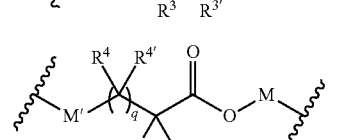 (VIb)

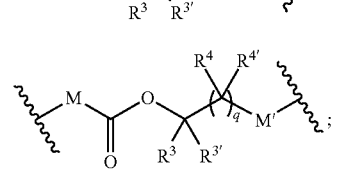 (VIc)

-continued

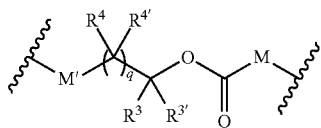
(VId)

wherein M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and wherein the groups $R^1$, $R^{1'}$, $R^2$, $R^{2'}$, $R^3$, $R^{3'}$, $R^4$ and $R^{4'}$ are independently selected from the group consisting of hydrogen, alkyl, alkoxy, alkoxy-alkyl, amino, alkyl amino, dialkylamino, amino-alkyl, alkylamino-alkyl, dialkylamino-alkyl and wherein one of the pairs of $R^1,R^{1'}$ and $R^2,R^{2'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl; and wherein one of the pairs of $R^3,R^{3'}$, $R^4,R^{4'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl;

q is 0 or 1;

R is selected from the group consisting of linear or branched hydrocarbon;

L is the linker group of formula II

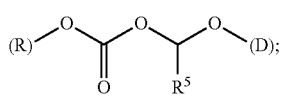
(II)

wherein $R^5$ is selected from hydrogen and $C_1$ to $C_6$ alkyl;

(R) indicates the end of the group bonded to the R group; and (D) indicates the end of the group attached to the group D D is selected from prostaglandins; and T is a triazole moiety.

In the copolymers of the invention biodegradability may be further controlled wherein at least one of $R^1$, $R^{1'}$, $R^2$, $R^{2'}$, $R^3$, $R^{3'}$, $R^4$ and $R^{4'}$ present in the polymer-prostaglandin conjugate is not hydrogen. Generally speaking the presence of the substituents provides a rate of degradation slower than would otherwise be observed. Without wishing to be bound by theory it is believed the substituents slow the rate of hydrolysis of the backbone providing a more extended period of controlled release at the required site prior to biodegradation and clearance of the polymer.

There is further provided a monomer-prostaglandin conjugate of formula (IV):

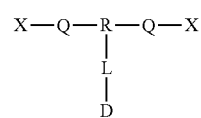
(IV)

where:

X may be the same or different at each occurrence and represents a terminal functional group comprising an alkyne or an azide;

Q is independently selected at each occurrence and may be present or absent and when present, represents a linking group;

R is selected from the group consisting of optionally substituted linear or branched hydrocarbon;

D is selected from prostaglandins;

L is a group of formula

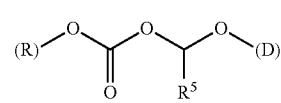
(II)

wherein $R^5$ is selected from hydrogen and $C_1$ to $C_6$ alkyl;

(R) indicates the end of the group bonded to the R group; and (D) indicates the end of the group attached to the group D.

In one aspect the monomer incorporates functional groups providing more effective biodegradation. Accordingly we provide the monomer-prostaglandin conjugate of formula IVa

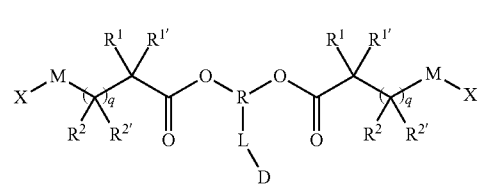
(IVa)

M is selected from the group consisting of a bond, optionally substituted $C_1$ to $C_{10}$ straight or branched chain aliphatic, the group —O ($C_1$ to $C_{10}$ straight or branched chain aliphatic) and an ether linking group comprising $C_1$ to $C_{10}$ straight or branched chain aliphatic interrupted by a oxygen (—O—);

q is 0 or 1;

X is a terminal functional group comprising an alkyne or an azide;

R is selected from the group consisting of optionally substituted linear or branched hydrocarbon;

D is selected from prostaglandins;

L is a group of formula

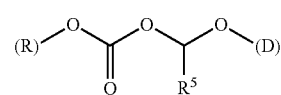
(II)

wherein $R^5$ is selected from hydrogen and $C_1$ to $C_6$ alkyl;
(R) indicates the end of the group bonded to the R group; and
(D) indicates the end of the group attached to the group D; and
$R^1$, $R^{1'}$, $R^2$ and $R^{2'}$ are independently selected from the group consisting of hydrogen, alkyl, alkoxy and alkoxyalkyl and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members.

The rate of biodegradation may be controlled where at least one of $R^1$, $R^{1'}$ and $R^2$, $R^{2'}$ is other than hydrogen.

The polymer prostaglandin conjugate is particularly useful in the form of an ocular implant and accordingly in a further embodiment there is provided an ocular implant comprising the above described polymer-prostaglandin conjugate.

Biodegradation of the polymer-prostaglandin conjugate in vivo may be controlled by the presence of substituents when at least one of $R^1$, $R^{1'}$, $R^2$, $R^{2'}$, $R^3$, $R^{3'}$, $R^4$ and $R^{4'}$ present in the monomers is not hydrogen and/or when the comonomer of formula (Va) is present and n is from 3 to 8 (preferably 3 or 4. This biodegradation chemistry introduced in the polymer backbone in formula (Ia), and (Va) and (Vb) can be used to ensure the in-use life of the product is greater than the treatment period controlled by the pendant linker chemistry. Conversely, the backbone substitution and resultant biodegradation chemistry can be used to control the treatment period independently of the pendant linker chemistry by ensuring the rate of biodegradation is faster than the rate of drug release. Such a system ensures no loss of potency near the end of the in-use life of the product.

The invention further allows the product to maintain its integrity and have minimal loss of function during the treatment period, yet biodegrade and dissolve as soon as possible thereafter. Such a system may be used to provide a non-linear loss of mass with respect to time during its in-use lifetime with minimal mass loss attributable to the polymer backbone during the treatment period and rapid mass loss of the polymer backbone after the treatment period. A cross-linked or hyperbranched polymer architecture provided by co-monomer (IIIa) where n is 3 or more with biodegradation chemistry incorporated into the polymer architecture provides such a mass loss profile.

Polymers can be modified to a network architecture, where n is from 3 to 8, that provides a non-linear loss of product mass compared with an equivalent linear polymer system. We have found that the underlying hydrolysis of biodegradation chemistry (e.g. ester) such as in the biodegradable backbone of formula (Ia) is the same, whether contained in a liner polymer or a cross-linked hydrogel. However, in the case of the cross-linked polymer, we have found that the cross-linked architecture ensures no significant loss of product mass occurs until a critical proportion of all the biodegradation moieties within the polymer chain are cleaved. Rapid mass loss occurs once that critical level is achieved. Hence, the mass loss profile is non-linear with very little loss of mass until the critical proportion of cleavage occurs after which there is a rapid loss of mass. Such a system allows a product to be produced that has little or no mass loss during the treatment period and rapid mass loss after the treatment period The combination of the linkage chemistry of the pendant drug to the polymer chain and the biodegradation chemistry incorporated into the polymer chain provides a means to separately control the rate of drug release from the rate of biodegradation of the polymer. The treatment period of the product can then be determined by either the period of controlled drug release or the period its takes for the polymer to biodegrade, whichever comes sooner. Often changes to polymer backbone to introduce the biodegradation chemistry also affects the rate of drug release (e.g. by introducing further hydrophilicity into the material). The use of the acyloxyalkylacyl linker allows changes to the biodegradation chemistry (in particular where such changes are incorporated into Q-X of the drug monomer) to occur without a significant change to the drug release rate.

BRIEF DESCRIPTION OF THE DRAWINGS

Specific embodiments of the invention are described with respect to the attached drawings.

In the drawings.

DETAILED DESCRIPTION

Figure 1:
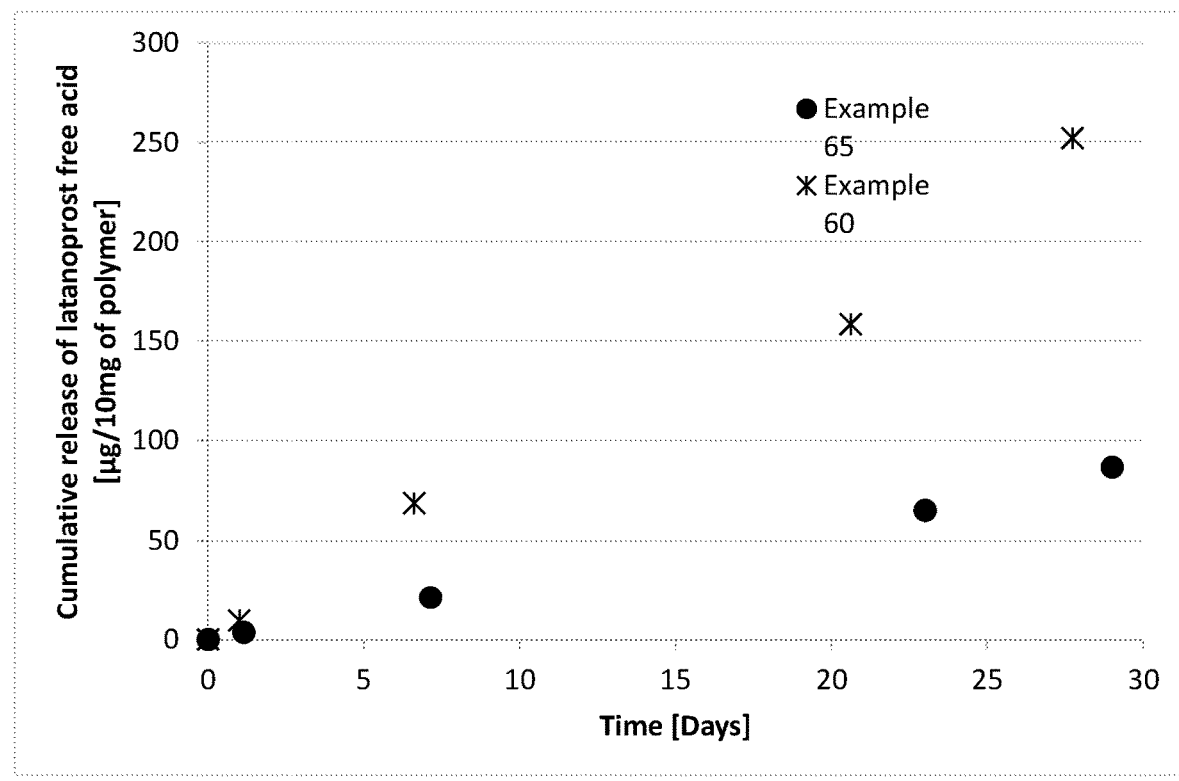
FIG. 1 is a graph including two plots showing the cumulative release (μg/10 mg) of latanoprost free acid with time exposed to isotonic phosphate buffer (pH 7.4) at 37.0° C. from drug-polymer conjugates of Examples 60 and 65.

The term "drug" refers to a substance for therapeutic use whose application (or one or more applications) involves: a chemical interaction, or physico-chemical interaction, with a subject's physiological system; or an action on an infectious agent, or on a toxin or other poison in a subject's body, or with biological material such as cells in vitro.

As used herein, the term "prodrug" refers to a derivative of the drug moiety, wherein the derivative may have little or none of the activity of the drug moiety per se yet is capable of being converted in vivo or in vitro into a drug moiety. An example of such derivatisation is the acetylation of one or more hydroxyl groups on a drug moiety, such that subsequent to being released in vivo the released prodrug is deactylated to produce the drug moiety.

As used herein, the term "pharmaceutically acceptable salt" means those salts that are safe and effective for use in pharmaceutical preparations. Pharmaceutically acceptable salts include salts of acidic groups present in compounds of the invention. Suitable salts may include sodium, potassium, ammonium, calcium, diethylamine and piperazine salts and the like. Pharmaceutically acceptable salts are described in Stahl P H, Wermuth C G, editors. 2002. Handbook of pharmaceutical salts: Properties, selection and use. Weinheim/Zurich: Wiley-VCH/VHCA.

As used herein, it is contemplated that the term "prostaglandin" includes, without limitation, natural prostaglandins and prostaglandin analogs. The prostaglandins are generally present in the polymer-prostaglandin conjulates and monomer prostaglandin conjugates as the acid residue portion of an ester formed at the (D) end of the linker.

The term "ACOA" refers to the group [(alkoxycarbonyl) oxy]alkyl alcohol portion of the ester which is the linker of the acid portion of the ester provided by drug (D). The ACOA links the drug to the polymer backbone moiety R and has the formula (II)

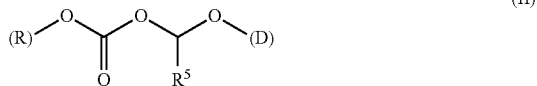

(II)

Polymers having drug s covalently attached thereto are sometimes referred to in the art as "polymer—drug conjugates". In some instances, it may be convenient to refer to a polymer-drug agent conjugate of the invention as a "drug-polymer conjugate", "drug-polymer conjugate", "drug-polymer conjugate", "polymer conjugate", "polymeric prodrug" or simply a "conjugate".

A hydrogel is a macromolecular polymer gel constructed of a network of cross-linked polymer chains. Hydrogels are synthesized hydrophilic monomers by either chain or step growth polymerisation, along with a functional crosslinker to promote network formation.

In one aspect, the present invention relates to a polymer-drug agent conjugate comprising a polymer backbone and a plurality of releasable drugs covalently bonded to and pendant from the polymer backbone. In accordance with this aspect, the polymer backbone comprises a plurality of triazole moieties.

Triazole moieties present in the polymer backbone of the polymer-drug conjugates, which are the product of an azide/alkyne coupling, are 1,2,3-triazole moieties.

1,2,3-Triazole moieties can be produced through the reaction of co-monomers having appropriate complementary terminal functional groups comprising alkyne and/or azide functionalities, under click reaction conditions. The terms "complementary terminal functionality" and "complementary terminal functional group" as used in the context of the present invention means a terminal chemical group that is capable of reacting with another chemical group to form a covalent intermolecular bond there between.

An appropriate click reaction for the formation of 1,2,3-triazoles is the Huisgen 1,3-dipolar cycloaddition of azides and alkynes (thermal) which gives a mixture of the 1,4 and 1,5 regioisomers of the 1,2,3-triazole. Click reactions suitable for forming triazole moieties may also be metal catalysed. For example, a Copper(I)-catalyzed Azide-Alkyne Cycloaddition (CuAAC) variant of the Huisgen cycloaddition of azides and terminal alkynes forms 1,2,3-triazoles. Use of a copper catalyst in the Huisgen cycloaddition reaction results in formation of a 1,4-substituted 1,2,3-triazole from azides and terminal alkynes, while use of a ruthenium catalyst enables use of terminal or internal alkynes and results in the formation of the alternate 1,5-regiosiomer. The use of a silver catalyst also results in the 1,4-substituted 1,2,3-triazole. Other metals that can be used include, but are not limited to, Ni, Pt, Pd, Rh, and Ir; the regiochemistry of the 1,2,3 triazole resulting from the use of these metal catalysts is less well defined Some exemplary click functional groups have been described by W. H. Binder and R. Sachsenhofer in Macromol. Rapid Commun., 2007, 28, 15-54, the disclosure of which is incorporated herein by reference.

The polymer-prostaglandin conjugate of Formula (I) is generally obtainable as a copolymer of at least one monomer of formula (IV):

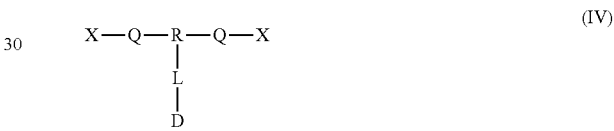

(IV)

where:
X may be the same or different at each occurrence and represents a terminal functional group comprising an alkyne or an azide;
Q is independently selected at each occurrence and may be present or absent and when present, represents a linking group;
R is selected from the group consisting of linear or branched hydrocarbon;
D is a prostaglandin;
L is a group of formula

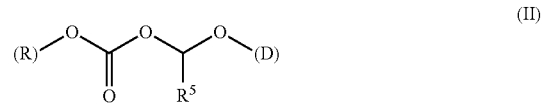

(II)

wherein $R^5$ is selected from hydrogen and $C_1$ to $C_6$ alkyl;
(R) indicates the end of the group bonded to the R group; and
(D) indicates the end of the group attached to the group D; and
a monomer of formula (V):

(V)

where:
A may be the same or different at each occurrence and represents a group comprising a terminal functional group comprising an alkyne or an azide functionality, wherein said terminal functional group is complementary to the terminal functional group X of formula (IV);

Z is an optionally substituted linker group; and n is an integer and is at least 2, such as 2 to 8 or 3 to 8.

The group Q may be absent and in some embodiments may be selected from the group consisting of:

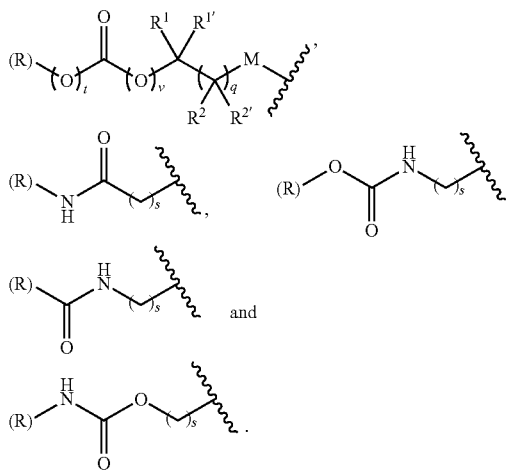

wherein (R) indicates the end of the group attached to the group R and the opposite end is attached to T in formula (I) (Ia) and (XXX) and to X in formula (IV), (IVa) and (IVb).

each of t and v are independently 0 or 1 and at least one of t and v is 1 (preferably one of t and v is 1 and the other is 0);

$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and s is from 0 to 10 preferably from 0 to 6; and preferred examples of Q include the following.

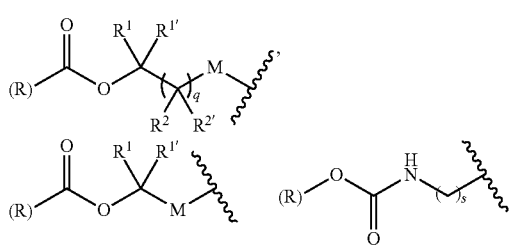

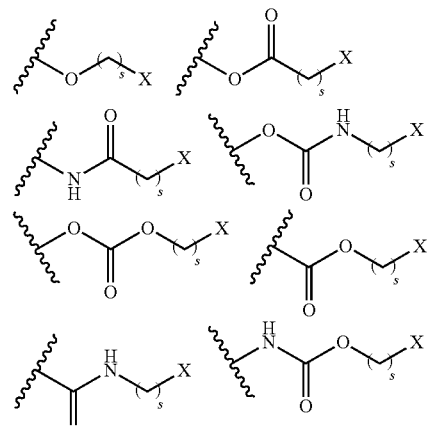

In a further set of embodiments Q is present in the monomer of formula (IV) (and the resulting segment of formula I), and each Q-X is independently selected from the following group:

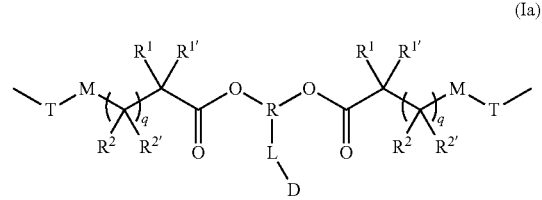

wherein s is from 0 to 10, preferably 0 to 6.

In one set of embodiments the drug-polymer conjugate comprising a plurality of polymer segments of formula Ia (Ia)

wherein $R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and at least one of $R^1$, $R^{1'}$, $R^2$ and $R^{2'}$ present in the polymer is not hydrogen;

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1;

R is selected from the group consisting of linear or branched hydrocarbon;

L is a linker group; and
D is selected from prostaglandins; and
T is a triazole moiety.

In some embodiments of the co-monomer of formula Vb the group B is a bond, oxygen, the group of formula -MOC(O)N(H)M'- or the group formula (VI)

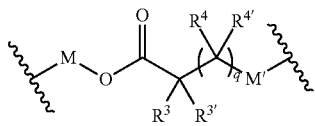
(VI)

wherein
M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$)
wherein $R^w$ is selected from hydrogen and $C_1$ to $C_4$ alkyl;
q is 0 or 1; and
wherein
the groups $R^3$, $R^{3'}$, $R^4$ and $R^{4'}$ are selected from the group consisting of hydrogen, $C_1$ to $C_6$ alkyl, $C_1$ to $C_6$ alkoxy and $C_1$ to $C_6$ alkoxy-($C_1$ to $C_6$ alkyl) and wherein one of the pairs of $R^3$,$R^{3'}$ and $R^4$, $R^{4'}$, may between the members of the pair form a carbocycle or heterocycle of 3 to 6 constituent ring members wherein the heterocycle may comprise from 1 to 3 constituent oxygen heteroatom ring members.

In some embodiments at least one of the groups R3, R3', R4 and R4' is other than hydrogen.

In preferred embodiments formula (Via) is of formula (Via-1) or (VIa-2)

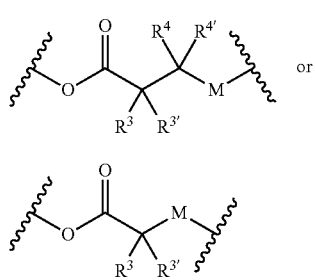
(VIa-1)

or (VIb-2)

In this embodiment the resulting polymer comprises substituents $R^1$, $R^{1'}$, $R^2$, $R^{2'}$, $R^3$, $R^{3'}$, (and in the case of formula (IVa) $R^4$ and $R^{4'}$) at least one of which is not hydrogen. In some embodiments at least one of $R^1$, $R^{1'}$, $R^2$, $R^{2'}$ is other than hydrogen, in other embodiments at least one of $R^3$, $R^{3'}$, $R^4$ and $R^{4'}$ is other than hydrogen one in some embodiments at least one of the groups $R^1$, $R^{1'}$, $R^2$, $R^{2'}$ is other than hydrogen and at least one of $R^3$, $R^{3'}$, $R^4$ and $R^{4'}$ is other than hydrogen.

In some embodiments, the polymer backbone of the polymer-drug conjugate comprises at least one triazole moiety selected from the group consisting of formula (VIIa) and (VIIb)):

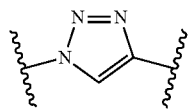
(VIIa)

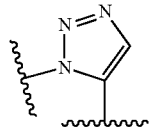
(VIIb)

The backbone may comprise a multiplicity of triazole moiety such as (VIIa), (VIIb) and combinations thereof.

Additional co-monomers useful for the preparation of polymer-drug conjugates of the invention comprise terminal functional groups comprising an alkyne and/or an azide. One skilled in the relevant art would understand that under appropriate reaction conditions, an alkyne and an azide containing functional groups can covalently react to form a triazole moiety. Click reaction conditions have been described in for example, Chem. Rev. 2008, 108, 2952, Angew Chem Int Ed 2001, 40, 2004, Angew Chem Int Ed Engl. 2002, July 15, 41(14): 2596-9, Aldrichimica Acta 2010, 43 (1) 15 and *Accounts of Chemical Research* 44 (9): 666-676.

In one aspect of the invention the drug conjugated with the polymer backbone of the drug-polymer conjugate and in the monomer is selected from the group consisting of prostaglandins, β-blockers and combinations of two or more thereof. In some embodiments it is useful to have drugs from two or more of these drug classes for specific treatments or to optimise treatment. Combinations of drugs from the prostaglandin and β-blocker classes are examples of combination therapies that may be provided by conjugation of two or more drugs to the same polymer backbone.

In the monomer-drug conjugate of formula (Ia) each substituent X represents a group comprising a terminal functional group comprising an alkyne or azide functionality. The terminal functional group X may be the same or different at each occurrence. Where the terminal functional groups (X) are the same, the monomer will generally be a diazide or dialkynyl monomer.

One skilled in the relevant art would understand that the terms "alkyne" and "azide" represent the following structures:

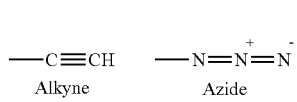

In one embodiment the drug is conjugated to the polymer backbone via an ACOA linkage formed between the drug D and the linker L. For example in one embodiment the drug is covalently bonded to the linker by a carboxylic acid ester. The ester may comprise an acid portion —C(O)— derived from an acid functional group of the drug and an alcohol portion provided by the linker or an acid portion of the ACOA may be derived from the linker and the alcohol portion by the drug.

Prostaglandins as described herein constitute an α-chain, an ω-chain and a 5-membered ring, numbered according to the C20 prostanoic acid as follows:

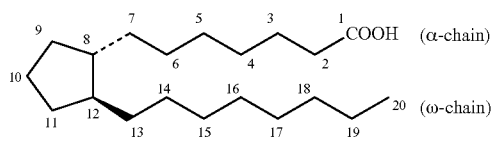

In one aspect, the present invention relates to a drug-polymer conjugate comprising a polymer backbone and a PGF2α class of prostaglandin conjugated to the polymer backbone.

Prostaglandins delivered by polymer-drug conjugates of the invention comprise at least one functional group selected from the group consisting of a carboxylic acid group at the 1 position, a hydroxy group at the 9 position, a hydroxy group at the 11 position, and a hydroxy group at the 15 position.

The carboxylic acid group at the 1 position, and the hydroxy groups at the 9, 11 and 15 position of the prostaglandin can serve as reactive functional groups for conjugation of the prostaglandin drug to a polymer. In conjugating the drug to the polymer backbone, the prostaglandin is conjugated to the polymer backbone via a selected group at the 1, 9, 11 or 15 position. The drug moiety (denoted D in formulae described herein) linked to the polymer is therefore an acid residue (in the case of conjugation at the 1 position) or an alcohol residue (in the case of conjugation at the 9, 11 or 15 positions) of the ACOA linking group conjugating the prostaglandin to the polymer backbone. The moiety represented by D may therefore be a releasable prostaglandin.

The prostaglandin is conjugated to the polymer backbone via an [alkoxycarbonyl)oxy]alkyl (ACOA) esterlinking group of Formula II. The [alkoxycarbonyl)oxy]alkyl ester-linking groups have been found to be hydrolytically labile in biological environments and can help to ensure that a sufficient amount of the drug is effectively released from the polymer conjugate to achieve therapeutic levels in the immediate vicinity of the polymer conjugate material.

When the prostaglandin is conjugated to the polymer backbone by an ACOA esterlinking group of Formula II, the ACOA ester linking group may link the drug at a position selected from the group consisting of the 1, 9, 11 and 15 position of the drug.

Typically the ACOA linking group of Formula II may link the drug at the 1 position of the prostaglandin thereby forming a linkage with the prostaglandin. An ACOA linkage is a form of an ester. Esters are normally described with respect to the acid residue and alcohol residue from which they are notionally derived. In the terms of an ACOA the prostaglandin provides the acid residue of the ester and the R group provides the alcohol residue of the ester.

As used herein, the term "acid residue" is a reference to that part of an ACOA linking group that is derived from a carboxylic acid functional group of a drug, after conjugation of the drug to the polymer backbone. The acid residue will generally have the structure —C(O)—. In the case of a prostaglandin, the carboxylic acid group is located at the 1 position.

As used herein the term "alcohol residue" is a reference to that part of an ACOA linking group that is derived from a hydroxy functional group of a drug, after conjugation of the drug to the polymer backbone. The alcohol residue will generally have the structure —O—. In the case of a prostaglandin, the hydroxy group may be selected by located at the 9, 11 or 15 position.

Typically the group D is a prostaglandin according to formula Xb

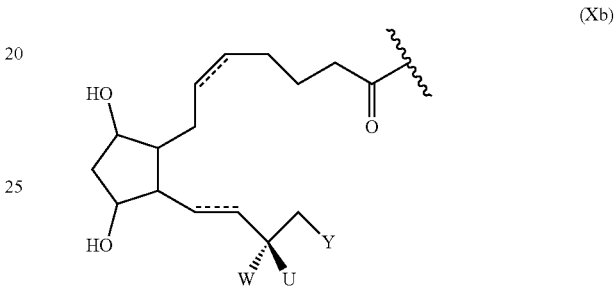

wherein $\sim\!\sim\!\sim\!\sim$ represents the point of attachment of the prostaglandin to linking group L;

------ represents a double or single bond;

Y is optionally substituted $C_4$ to $C_{10}$ hydrocarbyl or optionally substituted $C_4$ to $C_{10}$ hydrocarbyloxy;

W is hydroxy and U is hydrogen, or W and U are both fluoro, or W and U together form oxo.

It will be understood that prostaglandin contains chiral centres and is preferably of formula X(e)

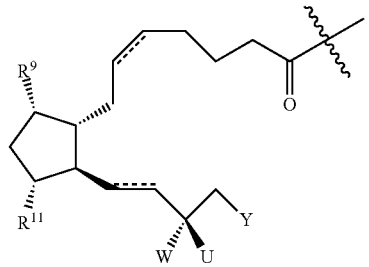

In preferred embodiments at least 80 mol % (more preferably at least 90 mol %) of the prostaglandin is present in the drug-polymer conjugate in the form of one optical isomer.

Examples of the drug monomer conjugate of formula II wherein the drug is a prostaglandin in acid residue form include monomers of formula (IIb):

Specific drug-monomers are of formula (IVa):

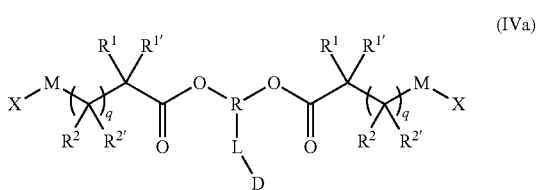
(IVa)

wherein the substituents are as hereinbefore defined except that D is selected from the specific prostaglandins in the form of the acid residue as shown in Table 1.

TABLE 1

| Drug | 1-COOH |
|---|---|
| PGF$_{2\alpha}$ | |
| Travoprost | |
| Carboprost | |
| Tafluprost | |
| Latanoprost | |

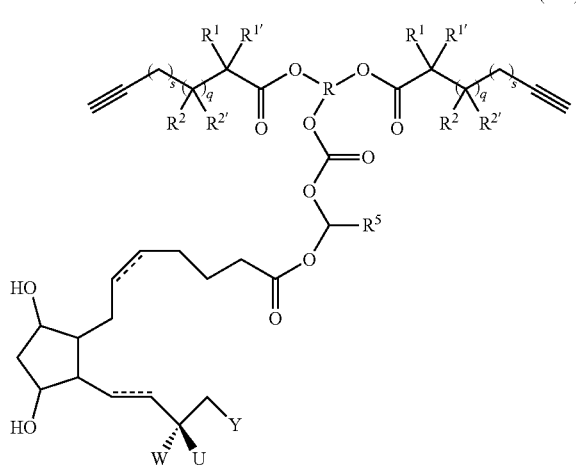
(IVb)

wherein:

R is straight or branched chain aliphatic;

the groups $R^1$, $R^{1'}$, $R^2$ and $R^{2'}$ are independently selected from the group consisting of hydrogen, $C_1$ to $C_6$ alkyl, $C_1$ to $C_6$ alkoxy, $C_1$ to $C_6$ alkoxy-($C_1$ to $C_6$ alkyl), and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and wherein at least one of $R^1$, $R^{1'}$, $R^2$ and $R^{2'}$ is preferably other than hydrogen;

q is 0 or 1;

s is from 0 to 10, preferably 0 to 6;

$R^5$ is selected from hydrogen and $C_1$ to $C_6$ alkyl, preferably from the group consisting of hydrogen, methyl, ethyl, propyl, isopropyl, butyl, isobutyl, sec-butyl, and tert-butyl and wherein:

------ represents a double or single bond;

Y is optionally substituted $C_4$ to $C_{10}$ hydrocarbyl or optionally substituted $C_4$ to $C_{10}$ hydrocarbyloxy;

W is hydroxy and U is hydrogen, or W and U are both fluoro, or W and U together form oxo.

Specific examples of the drug-polymer conjugate include conjugates of formula (Ia)

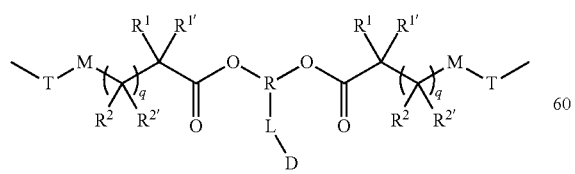
(Ia)

wherein the substituents are as hereinbefore defined except that D is selected from the specific prostaglandins in the form of the acid residue as shown in Table 1.

TABLE 1-continued

| Drug | 1-COOH |
|---|---|
| Unoprostone | 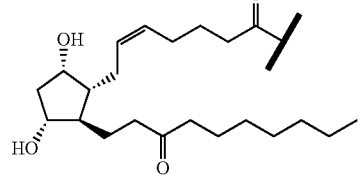 |
| Bimatoprost | 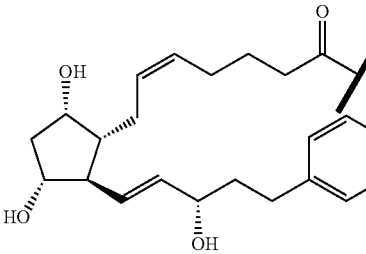 |

In this embodiment the linker L provides the alcohol portion of the ester formed with the acid residue of the prostaglandin.

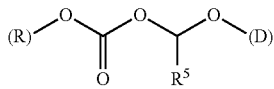

where $R^5$ is selected from hydrogen and $C_1$ to $C_6$ alkyl, preferably from the group consisting of hydrogen, methyl, ethyl, propyl, isopropyl, butyl, isobutyl, sec-butyl, and tert-butyl and more preferably is independently selected from hydrogen and methyl.

In the most preferred embodiment the drug-polymer comprises a plurality of segments of formula (Ib) or mixture thereof:

(Ib)

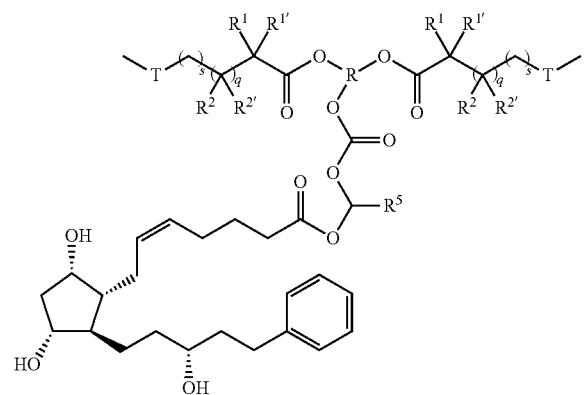

In a further set of embodiments there is provided a drug-monomer and co-polymer formed therefrom wherein the drug monomer is of (IVc):

(IVc)

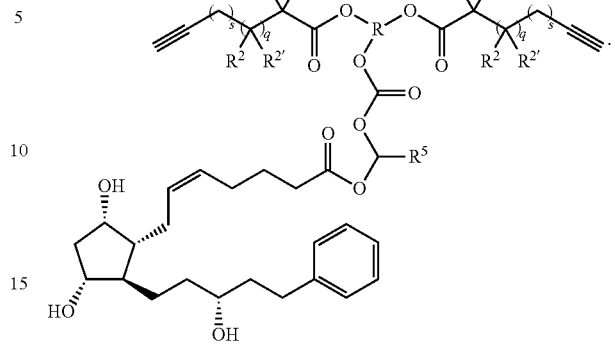

In one aspect the invention provides a drug-polymer conjugate comprising a polymer backbone and a plurality of drugs covalently bound to and pendant from the polymer backbone wherein the polymer backbone comprises a plurality of biodegradable groups of Formula (IX):

(IX)

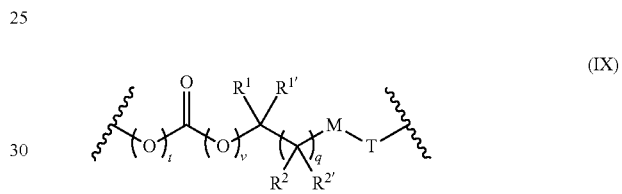

wherein:

each of t and v are independently 0 or 1 and at least one of t and v is 1 (preferably one of t and v is 1 and the other is 0); $R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and preferably at least one of $R^1$, $R^{1'}$, $R^2$ and $R^{2'}$ is preferably not hydrogen;

q is 0 or 1; and

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

and

T is a triazole moiety.

The polymer-prostaglandin conjugate in preferred embodiments comprises a polymer backbone and a plurality of prostaglandin groups covalently bound to a pendant from the polymer backbone via the linking group of formula (II). The polymer backbone comprises a plurality of biodegradable groups of Formula (IX):

wherein:

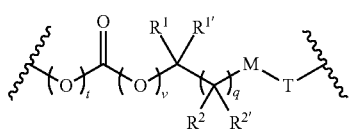
(IX)

each of t and v are independently 0 or 1 and at least one of t and v is 1 (preferably one of t and v is 1 and the other is 0);
$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and
preferably at least one of $R^1$, $R^{1'}$, $R^2$ and $R^{2'}$ is not hydrogen;
M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1; and
T is a triazole moiety.

The compound of formula (IX) includes a number of variables and may be in the form of any one of formulae (IXa), (IXb), (IXc), (IXd) or combinations of two or more thereof in the polymer backbone:

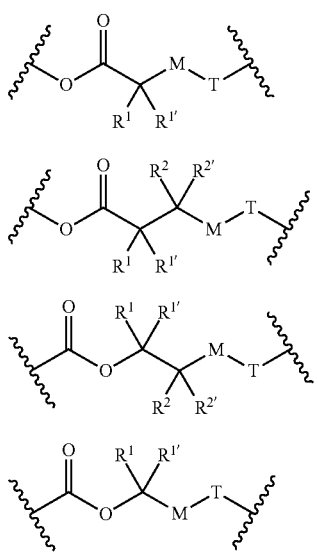

wherein the groups $R^1$, $R^{1'}$, $R^2$, $R^{2'}$, M and T are as herein defined in respect of formula I.

The present invention typically employs an ester to conjugate the prostaglandin drug to the polymer backbone. We have found the ACOA linking groups to be hydrolytically labile in biological environments and subject to less influence from the backbone groups. This allows the backbone biodegradation to be enhanced by the inclusion of ester groups as in Formulae (I), (Ia) (XXX) and the monomer of Formula (IVa) and (IVa) and the biodegradation to be further controlled by use of non-hydrogen substituents at one or more of $R^1$, $R^{1'}$, $R^2$, $R^{2'}$, R3, R3', R4 and R4'. Biodegradable moieties that may be present in the polymer backbone of polymer conjugates of some embodiments of the invention. Ester, anhydride and carbonate biodegradable moieties groups may further help to ensure that a sufficient amount of the drug is effectively released from the polymer conjugate to achieve therapeutic levels in the immediate vicinity of the polymer conjugate material and effective clearance of the polymer from the site of application trough biodegradation of the backbone. Biodegradation of the backbone may be controlled to allow completion of delivery of the prostaglandin payload from the polymer backbone or may degrade sufficiently rapidly to provide clearance of drug from the site of use before complete release from the linker of formula II.

Breakdown of the cleavable covalent bond can be promoted hydrolytically (i.e. hydrolytic cleavage) and may take place in the presence of water and an acid or a base. In some embodiments the cleavage may take place in the presence of one or more hydrolytic enzymes or other endogenous biological compounds that catalyze or at least assist in the cleavage process. For example, an ACOA linkage may be hydrolytically cleaved to produce a prostaglandin 1-carboxylic acid, an aldehyde and an alcohol. An ester biodegradation moiety may be hydrolytically cleaved to produce a carboxylic acid and an alcohol.

At the very least the drug will be releasable from the conjugate per se. However, as further described below, the polymer backbone may also biodegrade in vivo or in vitro such that the polymer backbone breaks into lower molecular weight fragments, with the drug remaining tethered to such a fragment(s) via L. In that case, the drug will nevertheless still be capable of being released or cleaved from L, which may or may not still be associated with the polymer conjugate per se.

In some embodiments monomers of formula (V) having complementary terminal functionality may be homofunctional. That is, each of the co-monomers may comprise one type of terminal functional group. The terminal functional groups of the co-monomers would be complementary and capable of reacting with one another to form a triazole moiety. For example, one co-monomer of formula (V) may comprise a terminal functional group comprising an alkyne functionality while the other co-monomer of formula (V) comprises a terminal functional group comprising an azide functionality. These co-monomers would be able to copolymerise under appropriate conditions to form a polymer conjugate having triazole moieties in the polymer backbone.

Examples of complementary monomers of formula (IV), (IVa) and (IVb) that are capable of copolymerising to form a polymer-prostaglandin conjugate with a monomer of formula (V), (Va), (Vb) include monomers of formula (IV), (IVa) and (IVb) where each group X is alkyne and a monomer of formula (IV), (IVa) and (IVb) wherein each group X is azide.

The monomers of formula (IV) and (V) may react with one another, for example, in a mole ratio of 1:1.

The co-monomer for reaction with the drug-monomer conjugate is of formula (V)

$$Z\text{-}(A)_n \qquad (V)$$

where:
A may be the same or different at each occurrence and represents a group comprising a terminal functional group comprising an alkyne or an azide functionality, wherein said terminal functional group is complementary to the terminal functional group X of formula (IV);
Z is an optionally substituted linker group; and
n is an integer and is at least 2.

In one set of embodiments the comonomer of Formula (V) has formula (Va)

(Va)

J represents a linking functional group,
n is 2 to 8;
Y comprises a chain of one or more groups selected from the group consisting of polyether, optionally substituted straight or branched $C_1$ to $C_{10}$ alkylene, amino, alkylamino, ether (—O—), ester, amide, carbonate and carbamate. In this embodiment it is preferred that Y comprises a polyether of formula $(OR^a)_m$ wherein $R^a$ is independently ethylene, propylene and butylene and m is from 1 to 300 (preferably 2 to 300) and the polyether is in chain with one or more groups selected from the group consisting optionally substituted straight or branched $C_1$ to $C_{10}$ alkylene, amino, ether, ester, amide, carbonate and carbamate The co-monomer may be of Formula V may have the formula Vb

(Vb)

wherein
A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (IVa);
J represents a linking functional group,
$R^a$ is selected from ethylene, propylene, butylene and mixtures thereof;
m is 1 to 300;
n is 2 to 8;
B is a bond, oxygen, the group of formula -MOC(O)N(H)M'-,-, -MOC(O)OM'-MC(O)NHM'-, the group formula selected from (VIa), (VIb), (VIc) and (VId):

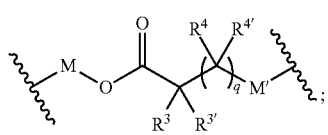

(VIa)

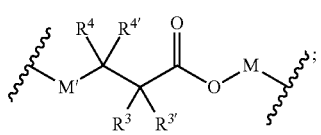

(VIb)

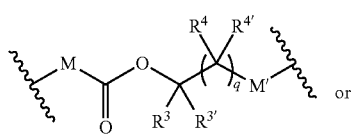

(VIc) or

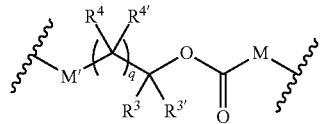

(VIc)

wherein
M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1; and
wherein in the monomers of formula (Va), (Vb), (Vc) and (Vc) the groups R3, R3', R4 and R4' are independently selected from the group consisting of hydrogen, alkyl, alkoxy, alkoxy-alkyl, amino, alkyl amino, dialkylamino, amino-alkyl, alkylamino-alkyl, dialkylamino-alkyl and wherein one of the pairs of $R^1,R^{1'}$ wherein one of the pairs of $R^3,R^{3'}$, $R^4,R^{4'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl.

In one set of embodiments the comonomer of formula (V) has formula (Vb):

(Vb)

$R^a$ at each occurrence may be ethylene, propylene or butylene;
m is from 1 to 300;
n is 3 to 8, preferably 3 or 4.
More specific examples of the comonomer of formula (V) may be selected from the group consisting of:

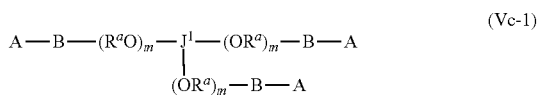

(Vc-1)

wherein $J^1$ is of formula $C_zH_{2z-1}$ (straight or branched chain) and wherein z is an integer from 1 to 8, preferably 3 to 8, and most preferably 3 or 4; and

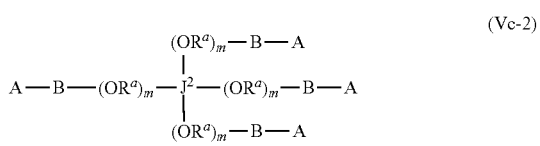

(Vc-2)

wherein $J^2$ is of formula $C_zH_{2z-2}$ (straight or branched chain) and wherein z is an integer from 1 to 8, preferably 3 to 8 and most preferably 3 or 4.
The group $R^5$ in the linker group (II) of the polymer-prostaglandin conjugate is preferably hydrogen or methyl.

In the monomer of formula (V), A represents a group comprising a terminal functional group comprising an alkyne or an azide functionality. The azide or alkyne functionality present in terminal functional group of moiety "A" is complementary to the azide or alkyne functionality present in the terminal functional group of X in formula (IV), such that upon reaction of the functional groups in A and X under click reaction conditions, a triazole moiety is formed.

In the monomer of formula (V), which may have formula (Va) or (Vb) the n is an integer and is at least 2. In some embodiments, n is an integer selected from the group consisting of 2, 3, 4, 5, 6, 7 and 8. In one form, in the monomer of formula (V) (which may have formula (Va) or (Vb)) n is 3-8, particularly 3 or 4. The monomer of formula (V) comprises at least two A moieties, which may be the same or different at each occurrence. When n is 2, the monomer is difunctional, may be linear and comprises two A moieties. When n is 3 or more, the monomer multifunctional and comprises 3 or more A moieties. In such embodiments, the monomer of formula (V) (which may have formula (Va) or (Vb)) may be a branched monomer. Three or more A moieties may be present when the monomer is branched. Monomers of formula (V) comprising at least three terminal functional groups provide branched architectures for the polymer conjugates of the invention.

As used herein, the term "group comprising a terminal functional group" encompasses embodiments where the group represents the terminal functional group per se, as well as embodiments where the terminal functional group is part of a larger chemical group.

The moiety "J" in formula (Va) and (Vb) represents an optionally substituted linker group. In some embodiments J may be a divalent group. Alternatively, J may be mulitvalent and be a branched group. When a monomers of formula (IV) and (Va) or (Vb) copolymerise, J forms a linker segment in the polymer backbone of the conjugate.

In some embodiments, J may comprise a linker moiety selected from the group consisting of optionally substituted linear or branched aliphatic hydrocarbon, optionally substituted carbocyclyl, optionally substituted heterocyclyl, optionally substituted aryl, optionally substituted heteroaryl, an optionally substituted polymeric segment, and combinations thereof.

Optionally substituted linear or branched aliphatic hydrocarbon linker moieties may be selected from optionally substituted $C_1$ to $C_{20}$, $C_1$ to $C_{10}$ or $C_1$ to $C_6$ linear or branched aliphatic hydrocarbons. The aliphatic hydrocarbons may be saturated or unsaturated hydrocarbon.

Optionally substituted carbocyclyl linker moieties may have from 3 to 12, 3 to 8 or 5 to 6 carbon ring members.

Optionally substituted heterocyclyl linker moieties may have from 3 to 12, 3 to 8 or 5 to 6 ring members and 1, 2, 3, 4 or more heteroatoms as a part of the ring. The heteroatoms may be independently selected from the group consisting of O, N and S.

Optionally substituted aryl linker moieties may have from 3 to 12, 3 to 8 or 5 to 6 carbon ring members and at least one unsaturation.

Optionally substituted heteroaryl linker moieties may have from 3 to 12, 3 to 8 or 5 to 6 ring members and 1, 2, 3, 4 or more heteroatoms as a part of the ring. The heteroatoms may be independently selected from the group consisting of O, N and S. The heteroaryl linker moiety also has at least one unsaturation.

Optionally substituted polymeric linker moieties may comprise any suitable polymer or copolymer. In some embodiments, it can be desirable for the polymeric moiety to comprise a biocompatible and/or biodegradable polymer. One skilled in the relevant art would be able to select suitable biocompatible and/or biodegradable polymers. Exemplary biocompatible polymers may include polyethers, polycarbonates, polyesters, polyamides, polyurethanes, and copolymers thereof, such as poly(ether-esters), poly(urethane-ethers), poly(urethane-esters), poly(ester-amides) and the like. Preferred biocompatible polymers are polyethers, polyesters, polycarbonates, polyurethanes, and copolymers thereof.

Exemplary polyethers include polymers of $C_2$ to $C_4$ alkylene diols, such as polyethylene glycol and polypropylene glycol, preferably polyethylene glycol.

Exemplary polyesters include polycaprolactone, poly(lactic acid), poly(glycolic acid) and poly(lactic-co-glycolic acid).

In one form, the polymeric linker moiety may comprise a biodegradable polymer. In general, biodegradable polymers comprise at least one biodegradable moiety. The biodegradable moiety may be selected from the group consisting of an ester, a carbamate, a carbonate, an amide, a urethane and a disulfide moiety. The biodegradable polymers comprise a combination of such moieties. One skilled in the relevant art would understand that such biodegradable moieties are capable of undergoing degradation or cleavage in a biological or physiological environment.

Optionally substituted polymeric linker moieties may be of any suitable molecular weight, and the desired molecular weight may depend on the type of polymer and its properties. In some embodiments, J comprises a polymeric moiety having a molecular weight of not more than 1500.

In one set of embodiments, J comprises a polyether linker moiety derived from polyethylene glycol (PEG). The polyether segment may be derived from a PEG of suitable molecular weight. In some embodiments, the PEG has a molecular weight in the range of from about 200 to 10,000, preferably from about 200 to about 3000.

In one set of embodiments, J comprises a linker moiety derived from lysine, including the ethyl ester of lysine such as ethyl-2,6-bis(((3-azidopropoxy)carbonyl)amino)hexanoate (ELDI) the di(1-pentynol)urethane of the ethyl ester of lysine and the di(1-pentynol)urethane of the 1-pentynol ester of lysine.

In some embodiments, the group "J" in the formula (Va) and (Vb) may comprise a functional group. The functional group may be selected from the group consisting of an amide, ether, ester, carbamate, urea, and carbonate ester functional group. Such functional groups will generally be cleavable functional groups, which can degrade in a biological environment.

In some embodiments of formula (V), J represents an optionally substituted polymeric linker moiety. The polymeric linker moiety may comprise a biocompatible and/or biodegradable polymer as described herein. In one set of embodiments B may comprises a polyether, polyester, polyamide, polyurethane, or copolymer thereof.

In one embodiment the co-monomer is of formula (Vb)

$$J\text{-}((OR^a)_m\text{---}B\text{-}A)_n \qquad (Vb)$$

wherein
J is selected from an optionally substituted hydrocarbon or hydrocarbon ether or polyether of from 2 to 4 hydrocarbon units in each ether unit;
$R^a$ at each occurrence may be ethylene, propylene or butylene;
m is from 1 to 300, such as 1 to 100 or 1 to 50;
n is from 2 to 8 (preferably 3 to 8 such as 3 or 4);

B is a bond, oxygen, the group of formula -MOC(O)N(H)M'- or the group formula (VIa)

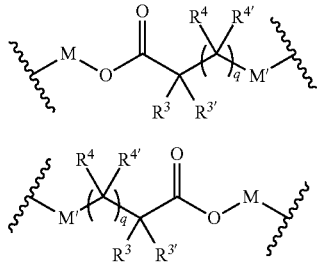

(VIa)

(VIb)

wherein
M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1; and
wherein in the monomers of formula (VIa) and (VIb) the groups
$R^3$, $R^{3'}$, $R^4$ and $R^{4'}$ are independently selected from the group consisting of hydrogen, alkyl, alkoxy and alkoxyalkyl and wherein one of the pairs of $R^3, R^{3'}$, $R^4, R^{4'}$, may between the members of the pair form a carbocycle or heterocycle of 3 to 6 constituent ring members wherein the heterocycle may comprise from 1 to 3 constituent oxygen heteroatom ring members.

In a preferred embodiment of the co-monomer of formula (V), (Va) and (Vb) the integer n is at least three, such as from 3 to 8 and most preferably is 3 or 4. In this embodiment the resulting co-monomer has 3 or more arms with reactive terminal group resulting in reaction with the drug-monomer of formula IV (including formula (IVa) to form a polymer network comprising pendent drug moieties covalently linked to the network of polymer backbone.

In a preferred set of embodiments the drug-polymer conjugate which is a co-polymer of a drug conjugate monomer of formula (IVa)

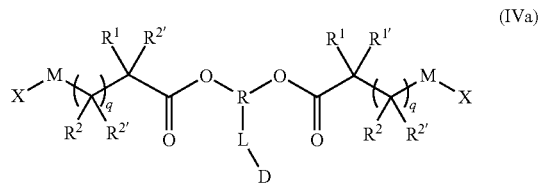

(IVa)

wherein
M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1;
X is a terminal functional group comprising an alkyne or an azide;
R is selected from the group consisting of linear or branched hydrocarbon;
L is a linker group; and
D is a releasable drug;
and a co-monomer of Formula (Vb $$J-((OR^a)_m—B-A)_n \qquad (Vb)$$

J is selected from an optionally substituted hydrocarbon or hydrocarbon ether or polyether of from 2 to 4 hydrocarbon units;
$R^a$ at each occurrence may be ethylene, propylene or butylene;
m is from 1 to 300;
n is from 3 to 8 (preferably 3 or 4);
B is a bond, oxygen, the group of formula -MOC(O)N(H)M'- or the group formula (IV)

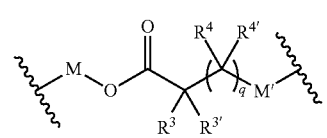

(VIa)

wherein
M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1; and
wherein in the monomers of formula (Ia) and (Vb) the groups
$R^1$, $R^{1'}$, $R^2$, $R^{2'}$, R3, R3', R4 and R4' are independently selected from the group consisting of hydrogen, alkyl, alkoxy, alkoxy-alkyl and wherein one of the pairs of $R^1$, R1' and $R^2$, R2', may between the members of the pair form a carbocycle or heterocycle of 3 to 6 constituent ring members wherein the heterocycle may comprise from 1 to 3 constituent oxygen heteroatom ring members; and one of the pairs of $R^3, R^{3'}$ and $R^4, R^{4'}$, may between the members of the pair form a carbocycle or heterocycle of 3 to 6 constituent ring members wherein the heterocycle may comprise from 1 to 3 constituent oxygen heteroatom ring members I.

In preferred embodiments the group B is of formula (IVa-1) or (IVb-1):

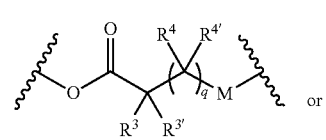

(VIa-1)

or

-continued (VIb-1)

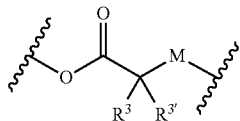

In one embodiment n in the co-monomer (V), such as (Va) or (Vb), is 3 or more and therefore branched and results in a network copolymer which we have found to provide a significant advantage in control of biodegradation. Accordingly the invention further provides a drug-polymer conjugate, which is a a copolymer, preferably a hyperbranched copolymer network, comprising network segments of formula (XXX):

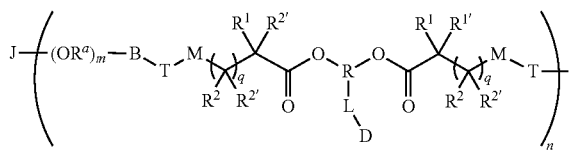

XXX wherein n groups are covalently bonded about group J and groups J, R, B, $R^a$, T, M, R, L and D and m and q are as hereinbefore defined for formulae (IVa) and (Vb) and n is an integer of from 2 to 8, preferably 3 to 8 and more preferably 3 or 4. Specific Examples of the network of formula XXX include compositions where L is of formula (II) and D selected from prostaglandins in Table 1.

In one set of embodiments of formula (Va), (Vb) and (XXX) the integer n is 3 to 8 and the branched linker J is a hydrocarbon of formula:

$C_zH_{2z+2-n}$ wherein z is from 1 to 8, preferably 3 to 8 and n is from 3 to 8 and preferably 3 or 4.

When n=2 the comonomer may be linear. Specific examples of the linker J where n is 2 include C1 to C10 alkylene such as ethylene and 1,2-propylene and 1,3-propylene:

—CH$_2$—CH$_2$—, —CH$_2$—CH(CH$_3$)— and —CH$_2$—CH$_2$—CH$_2$—.

Specific examples of the linker J where n is 3 to 8 include:

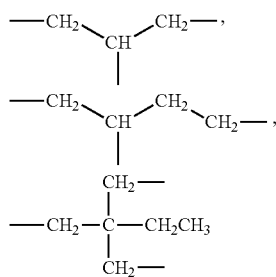

wherein n is 3; and

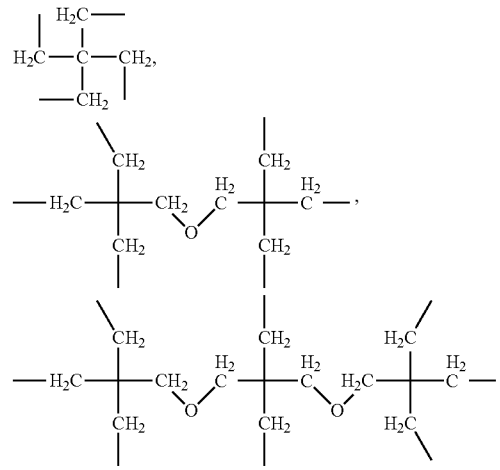

wherein n is from 4, 6 or 8.

In the formula IIIc the group $(OR^a)_m$ is a polymer of one or more of ethylene oxide, propylene oxide and butylene oxide.

In one set of embodiments the formula $(OR^a)_m$ in formula (V), (Va), (Vb) or formula (XXX) is selected from poly (ethylene oxide), poly(propylene oxide), poly(butylene oxide), block copolymers of one or more of poly(ethylene oxide), poly(propylene oxide) and poly(butylene oxide), block copolymers of two or more of poly(ethylene oxide), poly(propylene oxide) and poly(butylene oxide), wherein $(OR^a)_m$ has a molecular weight in the range of from 200 to 10,000.

Specific examples of the comonomer of formula (Vb) include:

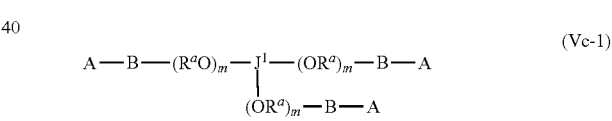
(Vc-1)

wherein $J^1$ is of formula $C_zH_{2z-1}$ (straight or branched chain) and wherein z is an integer from 1 to 8, preferably 3 to 8; and

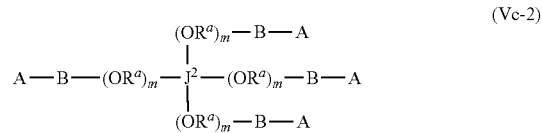
(Vc-2)

wherein $J^2$ is of formula $C_zH_{2z-2}$ (straight or branched chain) and wherein z is an integer from 1 to 8, preferably 3 to 8.

In formulae (I), (Ia), (Ib), (Ic), (IV), (IVa), (IVb), (V), (Va), (Vb) (Vc-1), (Vc-2), and (XXX) some or all of the substituents $R^1$, $R^{1'}$, $R^2$, $R^{2'}$, $R^3$, $R^{3'}$, $R^4$ and $R^{4'}$ are present. The substituents $R^1$, $R^{1'}$, $R^2$, $R^{2'}$, $R^3$, $R^{3'}$, $R^4$ and $R^{4'}$ independently selected from the group consisting of hydrogen, alkyl, alkoxy and alkoxyalkyl and wherein one of the pairs of $R^1,R^{1'}$ and $R^2,R^{2'}$, may between the members of the pair form a carbocycle or heterocycle of 3 to 6 constituent ring members wherein the heterocycle may comprise from 1 to 3 constituent oxygen heteroatom ring members; and wherein one of the pairs of $R^3,R^{3'}$, $R^4,R^{4'}$, may between the members of the pair form a carbocycle or heterocycle of 3 to 6 constituent ring members wherein the heterocycle may comprise from 1 to 3 constituent oxygen heteroatom ring members.

It is particularly preferred that at least one of the substituents on the carbon atom in a position alpha or beta to the carbonyl carbon, that is at least one of $R^1$, $R^{1'}$, $R^2$, $R^{2'}$, $R^3$, $R^{3'}$, $R^4$ and $R^{4'}$ (present in at least one of the reacting monomers) is other than hydrogen.

The substituents other than hydrogen significantly improve the control of biodegradation of the backbone. The control allows the backbone of the drug-polymer conjugate to be degraded in a controlled manner and any remaining drug active to be systemically diluted in the subject. The biodegradation allows the treatment term of the subject to be predetermined. This limitation on treatment term and biodegradation of the backbone are particularly advantageous in embodiments in which the drug polymer conjugate is used in localised treatment of tissue such as in the case of use of the drug-polymer conjugate in the form of an implant in treatment, for example of glaucoma.

In some embodiments at least one of $R^1$ and $R^{1'}$ is other than hydrogen and in further embodiments at least one of $R^2$ and $R^{2'}$ is other than hydrogen.

In embodiments of the invention where the monomer of formula (Va) and any one of the segment of formula (VIa), (VIb), (VIc) and (VId) are present, then substituents $R^3$, $R^{3'}$, $R^4,R^{4'}$ may be hydrogen where at least one of $R^1$, $R^{1'}$, $R^2$ and $R^{2'}$ are other than hydrogen or where $R^1$, $R^{1'}$, $R^2$ and $R^{2'}$ are hydrogen the control of biodegradation is significantly improved where at least one of $R^3,R^{3'}$, $R^4$ and $R^{4'}$ is other than hydrogen. In one set of embodiments at least one of $R^1$, $R^{1'}$, $R^2$ and $R^{2'}$ is other than hydrogen and at least one of $R^3$, $R^{3'}$, $R^4$, $R^{4'}$ is other than hydrogen.

It is generally preferred in order to enhance control of degradation that at least one of the groups on the carbon alpha to the carbonyl, that is $R^1$, $R^{1'}$, $R^3$ and $R^{3'}$, are other than hydrogen.

When one or more of $R^1$, $R^{1'}$, $R^2$, $R^{2'}$, $R^3$, $R^{3'}$, $R^4$ and $R^{4'}$ are other than hydrogen specific examples of the substituents other than hydrogen may be selected from the group selected from $C_1$ to $C_4$ alkyl such as methyl, ethyl, propyl, isopropyl, butyl, isobutyl, sec-butyl, and tert-butyl, $C_1$ to $C_4$ alkoxy such as methoxy, ethoxy, propyl, isopropoxy, butoxy, isobutoxy, sec-butoxy, and tert-butoxy; and $C_1$ to $C_4$ alkoxy substituted $C_1$ to $C_4$ alkyl such as one of the above $C_1$ to $C_4$ alkoxy examples substituted with one of the above $C_1$ to $C_4$ alkyl examples. Biodegradation may be enhanced by gemal-substitution with groups other than hydrogen. In cases where the carbon atom alpha or beta to the carbonyl carbon are di-substituted specific examples of the di-substitution pair may be selected from $C_1$ to $C_4$ alkyl such as methyl, ethyl, propyl, isopropyl, butyl, isobutyl, sec-butyl, and tert-butyl, $C_1$ to $C_4$ alkoxy such as methoxy, ethoxy, propyl, isopropoxy, butoxy, isobutoxy, sec-butoxy, and tert-butoxy; and C1 to C4 alkoxy substituted $C_1$ to $C_4$ alkyl such as one of the above $C_1$ to $C_4$ alkoxy examples substituted with one of the above $C_1$ to $C_4$ alkyl examples. Biodegradation is particularly enhanced where the carbon alpha to the carbonyl carbon is di-substituted, that is at least one or both of the pairs $R_1$, $R_{1'}$ and $R^3$, $R^{3'}$ are other than hydrogen.

The pairs of $R^1,R^{1'}$ and $R^2,R^{2'}$, may between the members of the pair form a carbocycle or heterocycle of 3 to 6 constituent ring members wherein the heterocycle may comprise from 1 to 3 constituent oxygen heteroatom ring members; and wherein one of the pairs of $R^3,R^{3'}$, $R^4,R^{4'}$, may between the members of the pair form a carbocycle or heterocycle of 3 to 6 constituent ring members wherein the heterocycle may comprise from 1 to 3 constituent oxygen heteroatom ring members.

Specific examples of carbocycles of this type include groups where one or more of the pairs $R^1,R^{1'}$; $R^2,R^{2'}$; $R^3,R^{3'}$ and; $R^4,R^{4'}$ between the pair form a spiro carbocycle via a linker selected from the group consisting of optionally substituted alkylene of from 2 to 5 methylene groups alkylene wherein the optional substituent is $C_1$ to $C_4$ alkyl or $C_1$ to $C_4$ alkoxy, and optionally substituted group of from 2 to 5 methylenes and from 1 to 3 oxygen heteroatoms wherein the optional substituents are $C_1$ to $C_4$ alkyl or $C_1$ to $C_4$ alkoxy.

Specific examples include the groups —$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—O—$CH_2$—$CH_2$—.

In formulas (Ia), (IVa), (Va), (vb), (Vc), Vd) and (XXX) the linking groups M or M and M' are present in the backbone portion of the monomer or polymer. The groups M and M' are independently selected and occurrences of M in portions of the drug-monomer conjugate and co-monomer are also independently selected. The drug-monomer conjugate contains two M linking groups which may be independently selected but in many embodiments it is convenient that they are the same.

The groups M and M' are each selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl. Preferred examples of embodiments where M and M' are $C_1$ to $C_{10}$ aliphatic include —$(CH_2)_y$— where y is from 1 to 6, preferably 1 to 4 such as methylene or ethylene and wherein one or two hydrogens in the chain —$(CH_2)_y$— may be substituted by methylene to form an alkene branch or $C_1$ to $C_4$ alkyl. In embodiments where one or both of M and M' are selected from —O ($C_1$ to $C_{10}$ straight or branched chain aliphatic) examples include —O—$(CH_2)_y$— where y is from 1 to 6, preferably 1 to 4 such as methylene or ethylene. In embodiments where one or both of M and M' are selected from ether linking group comprising $C_1$ to $C_{10}$ straight or branched chain aliphatic interrupted by a oxygen (—O—) examples include the group (CH2)-O—$(CH2)_y$ where y is from 1 to 6, preferably 1 to 4 such as methylene or ethylene. In embodiments where M and/or M' are the group —N($R^w$)—($C_1$ to $C_{10}$ straight or branched chain aliphatic) and an ether linking group comprising $C_1$ to $C_{10}$ straight or branched chain aliphatic interrupted by the group N($R^w$) wherein $R^w$ is selected from hydrogen and $C_1$ to $C_4$ alkyl examples include —N($R^w$)—$(CH2)_y$— where y is from 1 to 6, preferably 1 to 4 such as methylene or ethylene. In embodiments where one or both of M and M' are selected from amine linking group comprising $C_1$ to $C_{10}$ straight or branched chain aliphatic interrupted by a oxygen (—O—) examples include the group (CH2)-N($R^w$)—$(CH2)_y$ where y is from 1 to 6, preferably 1 to 4 such as methylene or ethylene.

In a number of embodiments of formulae (IVa), (IVb), (IVc) and (IVd) s is from 0 to 6 (preferably 0 to 2). The number s in some examples may be 0, 1 or 2.

According to one embodiment there is provided a method of delivering a drug to a subject, the method comprising administering to the subject a drug-polymer conjugate in accordance with the invention.

By the polymer conjugate being "suitable" for administration to a subject is meant that administration of the conjugate to a subject will not result in unacceptable toxicity, including allergenic responses and disease states. By the term "subject" is meant either an animal or human subject.

By "administration" of the conjugate to a subject is meant that the composition is transferred to the subject such that the drug will be released. The drug such as selected from one or more of prostaglandins, β-blocker, non-steroidal anti-inflammatory drugs (NSAIDs) and quinolones may be used in the treatment of eye disorders associated with increased intraocular pressure, such as glaucoma, it is preferred that the polymer conjugate is administered to an affected eye of a subject. Administration to the eye may be by way of intracameral to either the anterior or posterior chamber, intravitreal, subchoroidal or subconjunctival administration.

The polymer conjugates may be provided in particulate form and blended with a pharmacologically acceptable carrier to facilitate administration. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the conjugate is contained prior to being administered.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans. Suitable pharmacologically acceptable carriers are described in Martin, Remington's Pharmaceutical Sciences, 18th Ed., Mack Publishing Co., Easton, Pa., (1990).

The polymer drug conjugates may also form part of or be formed into an article or device, or be applied as a coating on an article or device, and implanted in a subject. By being "implanted" is meant that the article or device is totally or partly introduced medically into a subject's body and which is intended to remain there after the procedure.

Suitable dosage amounts of the drug and dosing regimens of the polymer conjugates can be determined by a physician and may depend on the particular condition being treated, the rate of release of the form the polymer backbone, the severity of the condition as well the general age, health and weight of the subject.

The form of the drug-polymer conjugate may be adjusted to be suited to the required application such as a coating, film, pellet, capsule, fibres, laminate, foam etc. The difference in the form of the conjugate provides a means to alter the release profile of the drug. For example the amount of polymer and drug may be the same in two different structures however the differences in the surface area to volume, rates of hydration and diffusion paths from the different physical forms or structures can result in different rates of drug release from essentially the same polymer.

The adjustment of the form of the polymer conjugate to suit the application and further to adjust the form to further control drug release provides an additional advantage over purely compositional and polymer structural means to control the release profile of the drug.

Some of the compositional/structural means to control the release of the drug include: controlling the loading of the drug; composition of the other co-monomers to adjust criteria such as hydrophobicity, flexibility, susceptibility to degradation, ability of the fragments to autocatalyse the polymer degradation, thermal stability of the polymer, mouldability, polymer solubility to assist casting etc.

In one set of embodiments, the drug may be released from the polymer conjugate such that it provides for a sustained drug delivery system. Such a delivery system may in its simplest form be the polymer conjugate provided in a desired shape, for example a pellet or more intricate shape. To promote surface area contact of the polymer conjugate under physiological conditions or with a biological environment, it may also be provided in the form of a foamed product or a coating on substrate.

By "sustained drug moiety delivery" is meant that the drug is released from the conjugate over a period of time, for example over a period of 10 or more minutes, 30 or more minutes, 60 or more minutes, 2 or more hours, 4 or more hours, 12 or more hours, 24 or more hours, 2 or more days, 5 or more days, 10 or more days, 30 or more days, 2 or more months, 4 or more months or over 6 or more months.

Drug-polymer conjugates of the present invention may be incorporated into drug delivery systems, therapeutic articles, devices or preparations, and pharmaceutical products for the treatment of ocular hypertension.

The drug-polymer conjugates of the present invention may be blended with one or more other polymers (for example, biodegradable polymers).

Drug-polymer conjugates in accordance with the invention can be formed into an article or device. The article or device may be fabricated in a range of forms. Suitably, the article or device is a medical device, preferably an ocular implant. The polymer conjugates in accordance with the invention can also be incorporated or made into coatings for target in vitro and in vivo applications.

The drug-polymer conjugates in accordance with the invention can be formed into an article or device that is suitable for administration to the eye.

In some embodiments, a drug-polymer conjugate may be in the form of a solid article (such as a particle, rod, sphere or pellet), a semi-solid, a deformable solid, a gel, or a liquid, for placement in the eye of the subject.

In another aspect, the present invention provides an ocular implant for the treatment of glaucoma comprising a drug-polymer conjugate of any one of the embodiments described herein.

In another aspect, the present invention provides an ocular implant for the treatment or prevention of endophthalmitis or ocular inflammation glaucoma comprising a drug-polymer conjugate of any one of the embodiments described herein.

In one form, the implant is a rod-shaped or sphere-shaped and is able to be housed within the lumen of a needle, such as a 20 to 27 gauge needle. The outer diameter of the implant would be less than 0.5 mm, preferably about 0.4 mm and more preferably 0.3 mm. The length of the rod-shaped implant can be selected to deliver the required dose of drug.

The implant can be of a number of different structural forms. The ocular implant could be a solid, a semi-solid or even a gel. A solid implant would comprise material with a melting point above 37° C., a semi-solid would have a glass transition temperature at or just below 25-37° C. A gel could be formed by appropriate formulation of the polymer conjugate with an appropriate plasticiser. In one set of embodiments, the implant could be a hydrogel.

In yet another aspect the present invention provides an injectable article for placement in an eye of the subject, wherein the injectable article comprises a drug-polymer conjugate of any one of the embodiments described herein. In one form, the injectable article is an injectable gel.

It is contemplated that an ocular implant may be a bi-component polymer structure where the drug-polymer conjugate can either be incorporated in the outer or inner layers of the bi-component structure. Incorporating the drug-polymer conjugate in the outer layer could be done to give a measured dose. Additionally the inner polymer layer could be to provide structural integrity to allow the delivery via the needle. Additionally the inner polymer could be designed to degrade either faster or slower than the polymer conjugate layer. This could be to alter the rate of bioerosion or the implant.

Possible means for producing rod-shaped implants include:

Melt extrusion of the drug-polymer conjugate or a material containing the drug-polymer conjugate through a shaped die.

In situ formation in a mold during the course of the polymerisation.

Simultaneous bi-component extrusion of the drug-polymer conjugate and other materials forming the outer or inner layers through an appropriate die.

Sequential overcoating extrusion of one polymer later with another. For example a core polymer fibre of PLGA could be melt overcoated with a polymer containing the drug-polymer conjugate.

It is also possible to solution coat an appropriate inner polymer carrier material (e.g. PLGA) with a solution containing the drug-polymer conjugate.

Possible means for producing rod-shaped or sphere-shaped implants include:

Injection moulding of the drug-polymer conjugate or a material containing the drug-polymer conjugate.

Solution casting in a mould of the drug-polymer conjugate or a material containing the drug-polymer conjugate.

In yet another aspect the present invention provides an injectable article for placement in an eye of the subject, wherein the injectable article comprises a drug-polymer conjugate of any one of the embodiments described herein. In one form, the injectable article is in the form of a gel.

In this specification "optionally substituted" is taken to mean that a group may or may not be substituted or fused (so as to form a condensed polycyclic group) with one, two, three or more of organic and inorganic groups (i.e. the optional substituent) including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups.

Preferred optional substituents include the aforementioned reactive functional groups or moieties, polymer chains and alkyl, (e.g. $C_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc.) alkoxy (e.g. $C_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), benzyl (wherein benzyl itself may be further substituted e.g., by $C_{1-6}$ alkyl, halo, hydroxy, hydroxy$C_{1-6}$alkyl, $C_{1-6}$ alkoxy, halo$C_{1-6}$ alkyl, cyano, nitro OC(O)$C_{1-6}$ alkyl, and amino), phenoxy (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), benzyloxy (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. NHC(O)$CH_3$), phenylamino (wherein phenyl itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$ alkyl, and amino), nitro, formyl, —C(O)-alkyl (e.g. $C_{1-6}$ alkyl, such as acetyl), 0-C(O)-alkyl (e.g. $C_{1-6}$alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$ alkyl, and amino), replacement of $CH_2$ with C=O, $CO_2H$, $CO_2$alkyl (e.g. $C_{1-6}$ alkyl such as methyl ester, ethyl ester, propyl ester, butyl ester), $CO_2$phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), $CONH_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro OC(O)$C_{1-6}$ alkyl, and amino), CONHalkyl (e.g. $C_{1-6}$ alkyl such as methyl amide, ethyl amide, propyl amide, butyl amide) CONHdialkyl (e.g. $C_{1-6}$ alkyl) aminoalkyl (e.g., HN $C_{1-6}$ alkyl-, $C_{1-6}$alkylHN-$C_{1-6}$ alkyl- and ($C_{1-6}$ alkyl)$_2$N—$C_{1-6}$ alkyl-), thioalkyl (e.g., HS $C_{1-6}$ alkyl-), carboxyalkyl (e.g., HO$_2$CC$_{1-6}$ alkyl-), carboxyesteralkyl (e.g., $C_{1-6}$ alkylO$_2$CC$_{1-6}$ alkyl-), amidoalkyl (e.g., H$_2$N(O)CC$_{1-6}$ alkyl-, H($C_{1-6}$ alkyl)N(O)CC$_{1-6}$ alkyl-), formylalkyl (e.g., OHCC$_{1-6}$alkyl-), acylalkyl (e.g., $C_{1-6}$ alkyl(O)CC$_{1-6}$ alkyl-), nitroalkyl (e.g., O$_2$NC$_{1-6}$ alkyl-), sulfoxidealkyl (e.g., R$^3$(O)SC$_{1-6}$ alkyl, such as $C_{1-6}$ alkyl(O)SC$_{1-6}$ alkyl-), sulfonylalkyl (e.g., R$^3$(O)$_2$SC$_{1-6}$ alkyl- such as $C_{1-6}$ alkyl(O)$_2$SC$_{1-6}$ alkyl-), sulfonamidoalkyl (e.g., 2HRN(O)SC$_{1-6}$ alkyl, H($C_{1-6}$ alkyl)N(O)SC$_{1-6}$ alkyl-).

It is understood that the compounds of the present invention (including monomers and polymers) may exist in one or more stereoisomeric forms (e.g. enantiomers, diastereomers). The present invention includes within its scope all of these stereoisomeric forms either isolated (in for example enantiomeric isolation), or in combination (including racemic mixtures).

The following examples are intended to illustrate the scope of the invention and to enable reproduction and comparison. They are not intended to limit the scope of the disclosure in any way.

EXAMPLES

General Experimental Procedures

The following compounds necessary for the invention were prepared according to literature methods or unless otherwise described using techniques well known to those skilled in the art.

2-(Prop-2-yn-1-yl)pent-4-yn-1-ol (CAS 432027-96-8); (2-Hydroxypropane-1,3-diyl bis(hex-5-ynoate) (CAS1627101-87-4); 1,3-Bis(prop-2-yn-1-yloxy)propan-2-ol (CAS 16169-22-5) were all prepared according to the procedure described in WO 2014134689 A1, Sep. 12, 2014. 2-(hydroxymethyl)-2-methylpropane-1,3-diyl bis alkyne esters were synthesized by treating a solution of 2-(hydroxymethyl)-2-methylpropane-1,3-diol and carboxylic acid (2 eq) in THF with DCC (2 eq) and DMAP (0.1 eq) for 16 h. The crude material was filtered and purified by flash chromatography to give the desired 2-(hydroxymethyl)-2-methylpropane-1,3-diyl bis(alkyne ester).

Linear poly(ethylene glycol) bis(azides) of differing molecular weights were purchase from commercial sources or prepared using standard literature methods.

Monomer Synthesis
Formation of Chloroalkyl Reagents
Method 1

Illustrated for Example 1-Chloroethyl (2-(prop-2-yn-1-yl)pent-4-yn-1-yl) carbonate To a solution of 2-(prop-2-yn-1-yl)pent-4-yn-1-ol (2.649 g, 21.7 mmol) in anhydrous pyridine (50 mL), 1-chloroethyl chloroformate (4.70 mL, 43.4 mmol) was added dropwise at 0° C. The reaction mixture was allowed to warm to room temperature and stirred for a further 2 days. The solvent was removed under reduced pressure. The residue was extracted with ethyl acetate and washed with water and brine. The organic phase was then dried over Na$_2$SO$_4$, filtered and concentrated and dried in vacuo. The crude residue was purified by flash chromatography.
Method 2

To an ice cold solution of 2-(prop-2-yn-1-yl)pent-4-yn-1-ol (2.0 g, 16.37 mmol) and DMAP (3.0 g, 24.55 mmol) in anhydrous dichloromethane (60 mL), was added 1-chloroethyl chloroformate (3.4 mL, 31.4 mmol). The reaction mixture was allowed to warm to room temperature and stirred for 18 h. The solvent was removed under reduced pressure. The crude was slurried with ethyl acetate and passed through a plug of silica. The title compound was isolated as a clear amber coloured liquid (3.01 g, 80% yield).
Formation of [alkoxycarbonyl)oxy]alkyl esters
Method 3

Illustrated for 1-((((2-(prop-2-yn-1-yl)pent-4-yn-1-yl)oxy)carbonyl)oxy)ethyl (Z)-7-((1R,2R, 3R, 5S)-3,5-dihydroxy-2-((R)-3-hydroxy-5-phenylpentyl)cyclopentyl)hept-5-enoate Example 6

To a 0° C. solution of latanoprost free acid (1.80 mmol) in DMF (5 mL) was added K$_2$CO$_3$ (3.66 mmol). After 5 mins a solution of alkyl chloride (e.g. 1-chloroethyl (2-(prop-2-yn-1-yl)pent-4-yn-1-yl) carbonate 5.98 mmol) in DMF (20 mL) was added via cannula and the resultant solution was allowed to warm to room temperature and stirred for 5 days or until the reaction is complete. EtOAc and sat. aq. NH$_4$Cl were added, the product was extracted (EtOAc), washed (H$_2$O, then brine), dried (Na$_2$SO$_4$), filtered and concentrated under reduced pressure. Flash chromatography (20%-100% EtOAc/petrol gradient elution) gave 1-((((2-(prop-2-yn-1-yl)pent-4-yn-1-yl)oxy)carbonyl)oxy)ethyl (Z)-7-((1R,2R, 3R,5S)-3,5-dihydroxy-2-((R)-3-hydroxy-5-phenylpentyl)cyclopentyl)hept-5-enoate (643.4 mg, 1.10 mmol, 61%) as a colourless viscous oil. R$_f$=0.60 (EtOAc).
Preparation of Precursors for Drug-Monomers Using the above methods and methods known to those skilled in the art, the following building block presursors to the drug-monomers were prepared.

TABLE 2

Examples of Building Block Precursors for drug-monomers:

| Ex | Structure/Name | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|
| 1 | 1-chloroethyl (2-(prop-2-yn-1-yl)pent-4-yn-1-yl) carbonate | clear colourless liquid | δ 6.43 (q, J = 5.8 Hz, 1H), 4.31 (d, J = 6.1 Hz, 2H), 2.48-2.36 (m, 4H), 2.25-2.14 (m, 1H), 2.03 (t, J = 2.6 Hz, 2H), 1.84 (d, J = 5.8 Hz, 3H). | — | — |

TABLE 2-continued

Examples of Building Block Precursors for drug-monomers:

| Ex | Structure/Name | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|
| 2 | 2-((((1-chloroethoxy)carbonyl)oxy) methyl)-2-methylpropane-1,3-diyl bis(2,2-dimethylpent-4-ynoate) | Colourless oil | $^1$H NMR (400 MHz, CDCl$_3$) δ 6.40 (q, J = 5.8 Hz, 1H), 4.18 (s, 2H), 4.06 (m, 4H), 2.43 (d, J = 2.6 Hz, 4H), 2.02 (t, J = 2.7 Hz, 2H), 1.83 (d, J = 5.8 Hz, 3H), 1.29 (s, 12H), 1.08 (s, 3H). | $^{13}$C NMR (100 MHz, CDCl$_3$) δ 176.1, 152.9, 84.8, 81.0, 70.9, 70.3, 65.9, 65.9, 42.6, 39.1, 29.8, 25.3, 24.8, 17.1. | — |
| 3 | 2-((((1-chloroethoxy)carbonyl)oxy) methyl)-2-methylpropane-1,3-diyl bis(hex-5-ynoate) | Colourless oil | $^1$H NMR (400 MHz, CDCl$_3$) δ 6.40 (q, J = 5.8 Hz, 1H), 4.15 (s, 2H), 4.03 (m, 4H), 2.48 (t, J = 7.4 Hz, 4H), 2.27 (td, J = 6.9, 2.6 Hz, 4H), 1.98 (t, J = 2.6 Hz, 2H), 1.88-1.81 (m, 7H), 1.05 (s, 3H). | $^{13}$C NMR (100 MHz, CDCl$_3$) δ 172.8, 152.9, 84.9, 83.2, 70.2, 69.5, 65.7, 65.6, 38.7, 32.8, 25.3, 23.6, 18.0, 17.1. | — |
| 4 | Chloromethyl (2-(prop-2-yn-1-yl)pent-4-yn-1-yl) carbonate | Colourless oil | $^1$H NMR (400 MHz, CDCl$_3$) δ 5.74 (s, 2H), 4.33 (d, J = 6.1 Hz, 2H), 2.41 (dd, J = 6.5, 2.7 Hz, 4H), 2.21 (m, 1H), 2.03 (t, J = 2.7 Hz, 2H). | — | — |
| 5 | 2-(((1-chloroethoxy)carbonyl)oxy) propane-1,3-diyl bis(hex-5-ynoate) | Colourless oil | δ 6.42 (q, J = 5.8 Hz, 1H), 5.19 (ddt, J = 6.7, 5.9, 3.9 Hz, 1H), 4.38 (ddd, J = 12.6, 8.9, 3.9 Hz, 2H), 4.21 (ddd, J = 12.3, 9.5, 6.3 Hz, 2H), 2.50 (td, J = 7.4, 2.5 Hz, 4H), 2.27 (td, J = 6.9, 2.6 Hz, 4H), 1.97 (td, J = 2.6, 0.9 Hz, 2H), 1.91-1.80 (m, 7H). | δ 172.43, 172.39, 152.24, 84.82, 83.03, 82.99, 73.94, 69.34, 61.88, 61.76, 32.49, 32.47, 25.09, 23.36, 23.35, 17.72, 17.68. | — |

Using the above methods and the building blocks prepared in Table 2 the following drug-monomers were prepared.

TABLE 3

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 6 | 1-((((2-(prop-2-yn-1-yl)pent-4-yn-1-yl)oxy)carbonyl)oxy)ethyl (Z)-7-((1R,2R,3R,5S)-3,5-dihydroxy-2-((R)-3-hydroxy-5-phenylpentyl)cyclopentyl)hept-5-enoate | 7 | colourless viscous oil | δ 7.30-7.27 (m, 2H), 7.23-7.17 (m, 3H), 6.76 (q, J = 5.4 Hz, 1H), 5.51-5.35 (m, 2H), 4.25 (d, J = 6.2 Hz, 2H), 4.16 (m, 1H), 3.95 (m, 1H), 3.67 (m, 1H), 2.80 (m, 1H), 2.68 (m, 1H), 2.41-2.09 (m, 11H), 2.02 (t, J = 2.6 Hz, 2H), 1.87 (t, J = 3.0 Hz, 2H), 1.82-1.55 (m, 8H), 1.51 (d, J = 5.4 Hz, 3H), 1.43-1.31 (m, 2H). | $^{13}$C NMR (101 MHz, CDCl$_3$) δ 171.84, 152.98, 142.19, 129.7, 129.68, 129.3, 128.47, 125.88, 91.52, 80.69, 80.64, 78.73, 74.67, 74.64, 71.35, 70.8, 70.78, 68.93, 52.82, 51.86, 42.57, 39.11, 36.27, 35.86, 33.43, 33.4, 32.18, 29.69, 26.96, 26.51, 26.49, 24.51, 24.49, 19.73, 19.71, 19.59. | 605.3 [M + Na]$^+$ |
| 7 | 2-((((1-(((Z)-7-((1R,2R,3R,5S)-3,5-dihydroxy-2-((R)-3-hydroxy-5-phenylpentyl)cyclopentyl)hept-5-enoyl)oxy)ethoxy)carbonyl)oxy)methyl)-2-methylpropane-1,3-diyl bis(2,2-dimethylpent-4-ynoate) | K$_2$CO$_3$ | Colourless oil | (400 MHz, CDCl$_3$) δ 7.32-7.26 (m, 2H), 7.21-7.16 (m, 3H), 6.73 (q, J = 5.4 Hz, 1H), 5.50-5.35 (m, 2H), 4.17 (br s, 1H), 4.12 (s, 2H), 4.04 (s, 4H), 3.95 (br s, 1H), 3.67 (m, 1H), 2.84-2.64 (m, 2H), 2.43 (d, J = 2.6 Hz, 1H), 2.40-2.10 (m, 6H), 2.02 (t, J = 2.6 Hz, 2H), 1.91-1.53 (m, 16H), 1.50 (d, J = 5.4 Hz, 3H), 1.43-1.32 (m, 2H), 1.28 (s, 12H), 1.07 (s, 3H). | $^{13}$C NMR (100 MHz, CDCl$_3$) δ 176.0, 171.7, 152.9, 142.1, 129.6, 129.3, 128.4, 128.4, 125.9, 91.5, 80.8, 78.8, 74.8, 71.3, 70.8, 69.7, 65.8, 53.0, 51.9, 42.6, 42.5, 39.1, 38.9, 35.8, 33.34, 33.30, 32.1, 29.7, 29.6, 27.0, 26.48, 26.45, 24.6, 24.4, 19.5, 16.9. | 818.8 [M + Na]$^+$ |
| 8 | 2-((((1-(((Z)-7-((1R,2R,3R,5S)-3,5-dihydroxy-2-((R)-3-hydroxy-5-phenylpentyl)cyclopentyl)hept-5-enoyl)oxy)ethoxy)carbonyl)oxy)methyl)-2-methylpropane-1,3-diyl bis(hex-5-ynoate) | K$_2$CO$_3$ | Colourless oil | (400 MHz, CDCl$_3$) δ 7.30-7.26 (m, 2H), 7.24-7.18 (m, 3H), 6.74 (q, J = 5.4 Hz, 1H), 4.16 (br s, 1H), 4.10 (s, 2H), 4.01 (m, 4H), 3.95 (br s, 1H), 3.67 (m, 1H), 2.83-2.64 (m, 2H), 2.47 (t, J = 7.4 Hz, 4H), 2.38-2.00 (m, 15H), 1.98 (t, J = 2.6 Hz, 2H), 1.87-1.54 (m, 14H), 1.51 (d, J = 5.4 Hz, 3H), 1.42-1.25 (m, 2H), 1.03 (s, 3H). | $^{13}$C NMR (100 MHz, CDCl$_3$) δ 172.9, 171.8, 153.1, 142.2, 129.8, 129.7, 129.5, 128.57, 128.55, 126.0, 91.7, 83.2, 79.0, 75.0, 71.5, 69.7, 69.5, 65.7, 53.2, 52.0, 42.7, 39.3, 38.7, 36.0, 33.50, 33.46, 32.8, 32.3, 29.8, 27.2, 26.63, 26.60, 24.59, 24.58, 23.6, 19.7, 18.0, 17.1. | 790.8 [M + Na]$^+$ |
| 9 | ((((2-(prop-2-yn-1-yl)pent-4-yn-1-yl)oxy)carbonyl)oxy)methyl (Z)-7-((1R,2R,3R,5S)-3,5-dihydroxy-2-((R)-3-hydroxy-5-phenylpentyl)cyclopentyl)hept-5-enoate | K$_2$CO$_3$ | — | (400 MHz, CDCl$_3$) δ 7.33-7.27 (m, 2H), 7.24-7.19 (m, 3H), 5.78 (s, 2H), 5.53-5.37 (m, 2H), 4.31 (d, J = 6.1 Hz, 2H), 4.19 (br s, 1H), 3.98 (br s, 1H), 3.70 (m, 1H), 2.86-2.67 (m, 2H), 2.44-2.11 (m, 11H), 2.05 (t, J = 2.6 Hz, 2H), 1.95-1.51 (m, 13H), 1.45-1.33 (m, 2H). | — | 568.9 [M + H]$^+$ |

Using the procedures described above the following monomers shown in Table 4 may be prepared.

TABLE 4
| Example | Drug | Linking Point | Alkyne/azide precursor | Production Method | Monomer |
|---|---|---|---|---|---|
| 10 | TVP | 1-COOH | 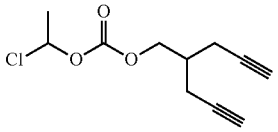 | Method 3 | 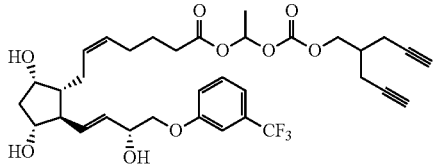 |
| 11 | TAF | 1-COOH | 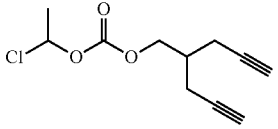 | Method 3 | 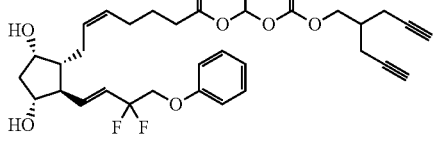 |
| 12 | BIM (free acid) | 1-COOH | 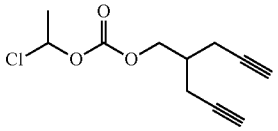 | Method 3 | 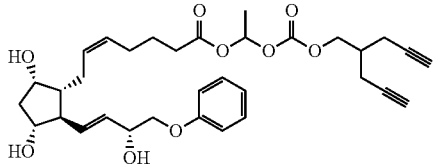 [SMILES: C#CCC(CC#C)COC(=O)OC(C)OC(=O)CCC/C=C\C[C@@H]1[C@@H](/C=C/[C@@H](O)COc2ccccc2)[C@H](O)C[C@@H]1O] |
| 13 | LTP | 1-COOH | 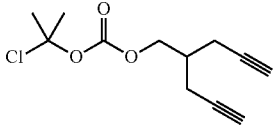 [SMILES: C#CCC(CC#C)COC(=O)OC(C)(C)Cl] | Method 3 | 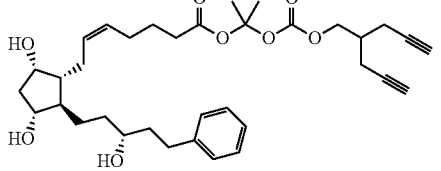 |
| 14 | LTP | 1-COOH | 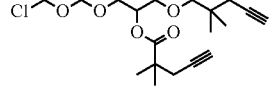 | Method 3 | 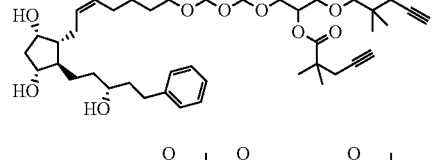 |
| 15 | LTP | 1-COOH | 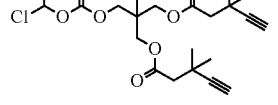 | Method 3 | 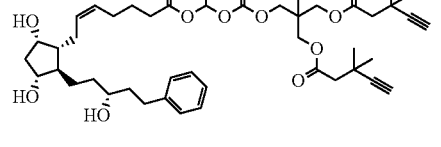 |
| 16 | TVP | 1-COOH | 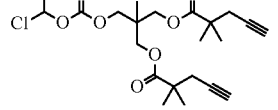 | Method 3 | 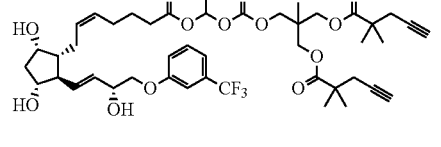 |
| 17 | TAF | 1-COOH | 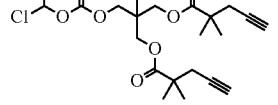 | Method 3 | 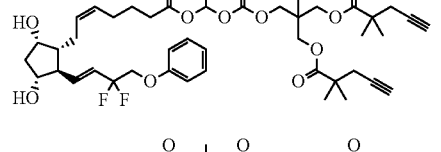 |
| 18 | BIM (free acid) | 1-COOH | 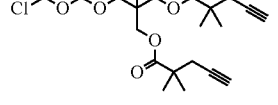 | Method 3 | 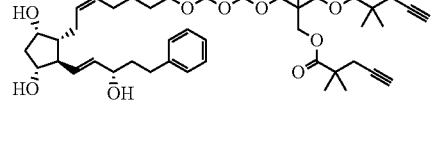 |

TABLE 4-continued

| Example | Drug | Linking Point | Alkyne/azide precursor | Production Method | Monomer |
|---|---|---|---|---|---|
| 19 | TVP | 1-COOH | [structure] | Method 3 | [structure] |
| 20 | TAF | 1-COOH | [structure] | Method 3 | [structure] |
| 21 | BIM (free acid) | 1-COOH | [structure] | Method 3 | [structure] |
| 22 | TVP | 1-COOH | [structure] | Method 3 | [structure] |
| 23 | TAF | 1-COOH | [structure] | Method 3 | [structure] |
| 24 | BIM (free acid) | 1-COOH | [structure] | Method 3 | [structure] |
| 25 | LTP | 1-COOH | [structure] | Method 3 | [structure] |
| 26 | TVP | 1-COOH | [structure] | Method 3 | [structure] |

TABLE 4-continued

| Example | Drug | Linking Point | Alkyne/azide precursor | Production Method | Monomer |
|---|---|---|---|---|---|
| 27 | TAF | 1-COOH | (structure) | Method 3 | (structure) |
| 28 | BIM (free acid) | 1-COOH | (structure) | Method 3 | (structure) |
| 29 | LTP | 1-COOH | (structure) | Method 3 | (structure) |
| 30 | LTP | 1-COOH | (structure) | Method 3 | (structure) |
| 31 | LTP | 1-COOH | (structure) | Method 3 | (structure) |
| 32 | LTP | 1-COOH | (structure) | Method 3 | (structure) |

LTP = latanoprost;
TVP = travoprost;
TAF = tafluprost;
BIM = bimatoprost.

Preparation of Drug-Polymer Conjugates
Preparation of Co-Monomers
Method 4: General Method A: For the Preparation of PEG Azide Co-Monomers: Esters Illustrated Using Example 44

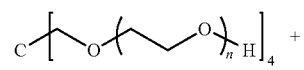

-continued

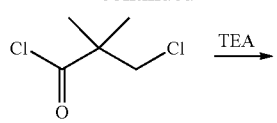

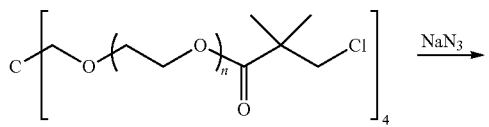

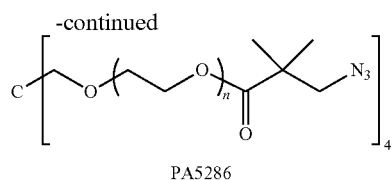

PA5286

4-arm PEG$_{2000}$-OH (5 g, 2.5 mmol), TEA (3.1 mL, 4.4 eq) and DCM (50 mL) were introduced into a round-bottom flask equipped with a rubber septum and a magnetic stirrer bar and placed under a nitrogen atmosphere. The solution was stirred and cooled to 0° C. in an ice bath. A mixture of 3-chloro-2,2-dimethylpropionyl chloride (2.6 mL, 8 eq) in 10 mL of DCM was added dropwise with a syringe equipped with a needle. The solution was allowed to warm to room temperature and stirred overnight. After filtration, DCM was removed under vacuum and the product was purified by flash chromatography (EtOAc [DCM/MeOH 95/5] 100:0→0:100) to give the product (5.14 g, 83%) which was was analysed by MALDI-ToF mass spectrometry ($M_n$=2458.3 g·mol$^{-1}$; $M_w$=2474.8 g·mol$^{-1}$; Đ =1.007). Đ C-(PEG-OCO—C(CH$_3$)$_2$—CH$_2$—Cl)$_4$ (5.135, 2.09 mmol), NaN$_3$ (5.43 g, 40 eq) and DMF (75 mL) were introduced into a round-bottom flask equipped with a rubber septum and a magnetic bar. The solution was stirred for 24 h at 50° C. The solvent was evaporated and the polymer was purified by flash chromatography (EtOAc:Acetone 100:0→0:100) and dried under vacuum to give the product (Example 44) (3.48 g, 67%). MALDI-ToF mass spectrometry (Mn=2439.7 g·mol$^{-1}$; Mw=2451.7 g·mol$^{-1}$; Đ =1.005). $^1$H NMR (C—(CH$_2$—CH$_2$—O)—CO—C(CH$_3$)$_2$—CH$_2$—N$_3$)$_4$: 1.30 ppm (6H, (CH$_3$)$_2$; 3.4 ppm -3.8 ppm (44H, —CH$_2$—CH$_2$—O); 4.28 ppm (—CH$_2$—N$_3$)). Overall yield=56%.

Method 5:
General Method B for the Preparation of PEG Azide Co-Monomers: Esters

Illustrated Using Example 37

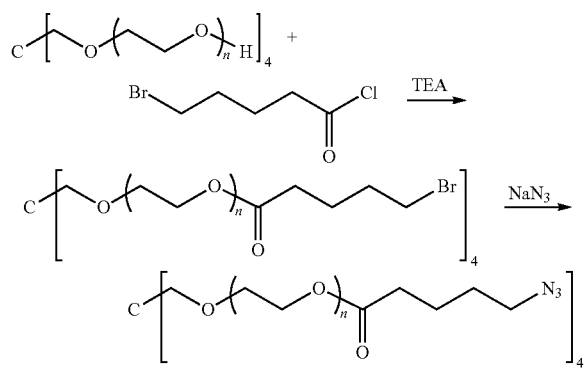

4-arm PEG$_{2000}$-OH (5.0 g, 2.5 mmol), TEA (2.23 g, 3.1 ml, 22 mmol, 8.8 eq) and DCM (50 mL) were introduced in to a round-bottom flask equipped with a stir bar and placed under nitrogen. The solution was stirred and cooled to 0° C. A mixture of 5-bromovaleryl chloride (3.99 g, 2.68 ml, 20.0 mmol, 8 eq) in 10 mL of DCM was added dropwise. The solution was stirred overnight and allowed to warm to room temperature. After filtration, 30 mL of brine was added to the mixture and the aqueous phase was washed three times with DCM (3×100 ml). The organic phases were combined, dried (MgSO$_4$) and under vacuum. The product was purified by column chromatography (EtOAc:Hex=40:60 to 100:0).

C-(PEG-Br)$_4$, (4.36 g. 1.64 mmol), NaN$_3$ (4.27 g, 65.7 mmol and DMF (50 mL) were introduced in to a round-bottom flask. The solution was stirred for 24 h at room temperature. The solvent was evaporated, the mixture solubilised in acetone and filtered. The acetone was evaporated, brine (50 mL) was added and the mixture was washed with ethyl acetate (3×50 mL). The organic phases were combined, dried over MgSO$_4$ and dried under vacuum.

Method 6: General Method C for the Preparation of PEG Azide Co-Monomers: Carbamate Illustrated Using Example 49

4-Arm PEG$_{2000}$-Carbamate Tetraazide Co-Monomer

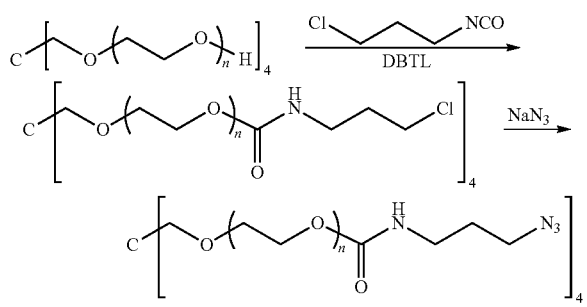

4-arm PEG$_2$000-OH (6 g, 3 mmol), dibutyltin dilaurate (0.19 g, 0.3 mmol) and dichloromethane (18 mL) were introduced in to a RBF equipped with a septum and a magnetic bar. 3-Chloropropyl isocyanate (2.15 g, 18.0 mmol) was added dropwise and the mixture was stirred for 24 h at room temperature. The solvent was evaporated and the product analysed by $^1$H NMR and MALDI-TOF spectroscopies.

4-arm PEG$_{2000}$-OCONH—C$_3$H$_6$—Br (4.56 g, 3.91 mmol), NaN$_3$ (10.2, 157 mmol) and DMF (120 mL) were introduced into a round-bottom flask. The solution was stirred for 48 h at 50° C. The solvent was evaporated, the mixture solubilised in EtOAc (50 mL) and filtered, washed with brine (25 mL), dried over NaSO$_4$ and the solvent removed under vacuum. The product was purified by flash chromatography (EtOAc:Hex=40:60 to 100:0 then Acetone 100).

Method 7: General Method for the Preparation of PEG Azide Co-Monomers: Amide

Illustrated Using Example 47 Amide

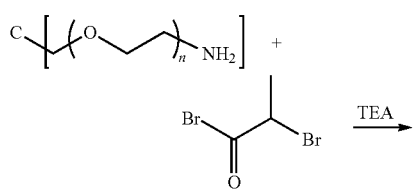

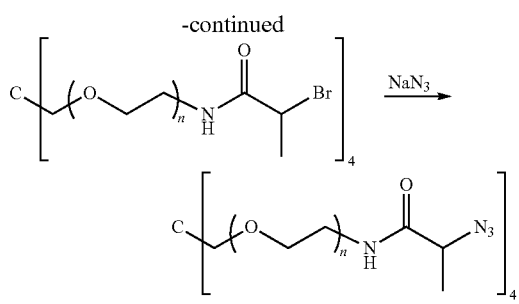

4arm amino-PEG (2.5 g, 1.25 mmol), TEA (1.53 mL, 11 mmol, 8.8 eq) and DCM (28 mL) were introduced in a two-neck round-bottom flask equipped with a pressure equalizing addition funnel and placed under nitrogen. The solution was stirred and cooled down to 0° C. Then, a mixture of 2-bromopropionyl bromide (1.05 mL, 10 mmol, 8 eq) in 2 mL of DCM was added dropwise through the dropping funnel. The solution was stirred overnight and allowed to warm up to room temperature. The mixture was dried, solubilised in 50 mL EtOAc, filtered and washed with brine (25 mL). The aqueous phase was washed twice with EtOAc, the organic phases were combined and dried over MgSO$_4$ and then under vacuum. MALDI-ToF: Mn=2437.4 g/mol; Mw=2440.7 g/mol; Đ=1.001.

(Br—CONH-PEG-)$_4$-C (0.792 g, 0.325 mmol), NaN$_3$ (0.845 g, 1.3 mmol, 40 eq) and DMF (10 mL) were introduced to a round-bottom flask. The solution was stirred during 24 h at room temperature. The solvent was evaporated, the mixture solubilised in 50 mL of ethyl acetate, filtered, washed with brine (25 mL), dried over NaSO$_4$ and under vacuum. MALDI-ToF: Mn=2185.5 g/mol; Mw=2191.6 g/mol; Đ=1.002.

Using the above methods the following azide monomers in Table 5 were made.

TABLE 5

| Ex. | Structure | PEG used | MALDI-ToF |
|---|---|---|---|
| 33 | 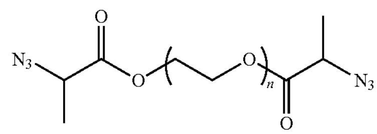 | PEG400 | $M_n$ = 659.0 g/mol<br>$M_w$ = 672.0 g/mol<br>Đ = 1.02 |
| 34 | 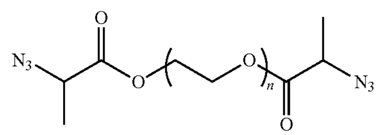 | PEG1000 | $M_n$ = 1256.4 g/mol<br>$M_w$ = 1278.5 g/mol<br>Đ = 1.002 |
| 35 | 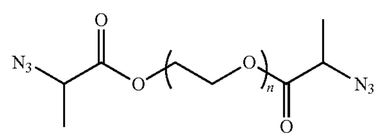 | PEG3000 | $M_n$ = 3186.4 g/mol<br>$M_w$ = 3205.8 g/mol<br>Đ = 1.01 |
| 36 | 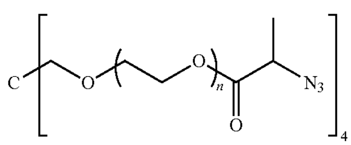 | PEG2000<br>4 arm | $M_n$ = 2266.4 g/mol<br>$M_w$ = 2315.8 g/mol<br>Đ = 1.02 |
| 37 | 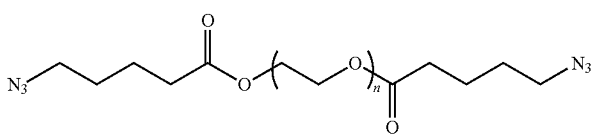 | PEG400 | $M_n$ = 599.1 g/mol<br>$M_w$ = 605.1 g/mol<br>Đ = 1.01 |
| 38 | 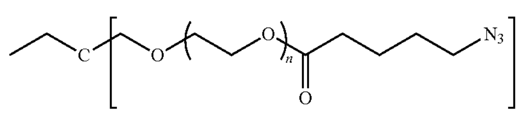 | PEG1000<br>3 arm | $M_n$ = 1361.8 g/mol<br>$M_w$ = 1375.4 g/mol<br>Đ = 1.01 |
| 39 | 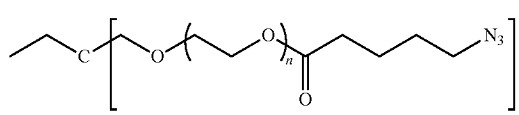 | PEG450<br>3 arm | — |
| 40 | 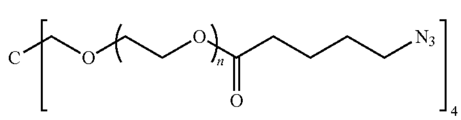 | PEG2000<br>4 arm | $M_n$ = 2351.5 g/mol<br>$M_w$ = 2372.1 g/mol<br>Đ = 1.008 |

TABLE 5-continued

| Ex. | Structure | PEG used | MALDI-ToF |
|---|---|---|---|
| 41 | 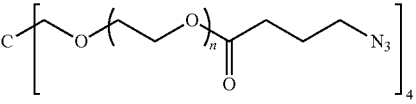 | PEG2000 4 arm | $M_n$ = 2420.0 g/mol<br>$M_w$ = 2439.7 g/mol<br>Đ = 1.008 |
| 42 | 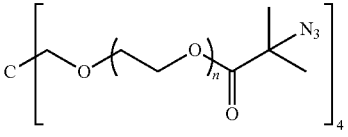 | PEG2000 4 arm | $M_n$ = 2350.4 g/mol<br>$M_w$ = 2368.9 g/mol<br>Đ = 1.008 |
| 43 | 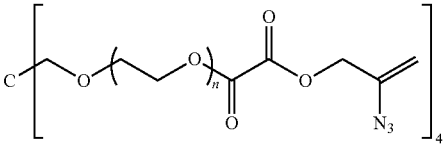 | PEG2000 4 arm | $M_n$ = 2395.0 g/mol<br>$M_w$ = 2409.8 g/mol<br>Đ = 1.006 |
| 44 | 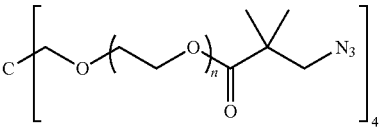 | PEG2000 4 arm | $M_n$ = 2439.7 g/mol<br>$M_w$ = 2451.7 g/mol<br>Đ = 1.005 |
| 45 | 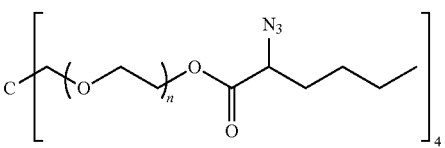 | PEG2000 4 arm | $M_n$ = 2480.3 g/mol<br>$M_w$ = 2490.0 g/mol<br>Đ = 1.004 |
| 46 | 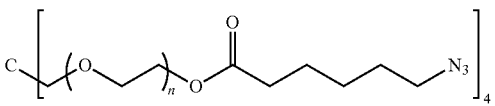 | PEG2000 4 arm | $M_n$ = 2436 g/mol<br>$M_w$ = 2474 g/mol<br>Đ = 1.016 |
| 47 | 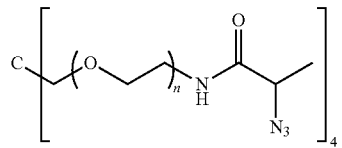 | PEG2000 4 arm | $M_n$ = 2202.1 g/mol<br>$M_w$ = 2208.3 g/mol<br>Đ = 1.003 |
| 48 | 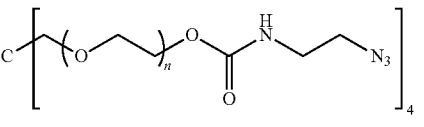 | PEG2000 4 arm | $M_n$ = 2438.1 g/mol<br>$M_w$ = 2458.1 g/mol<br>Đ = 1.008 |
| 49 | 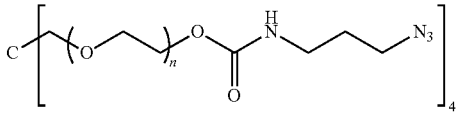 | PEG2000 4 arm | $M_n$ = 2525.9 g/mol<br>$M_w$ = 2535.1 g/mol<br>Đ = 1.003 |
| 50 | 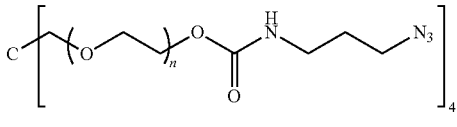 | PEG800 | $M_n$ = 1217.9 g/mol<br>$M_w$ = 1222.1 g/mol<br>Đ = 1.003 |
| 51 | 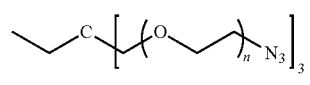 | PEG450 3 arm | $M_n$ = 664.2 g/mol<br>$M_w$ = 677.1 g/mol<br>Đ = 1.02 |
| 52 | 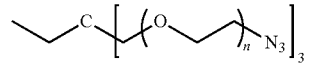 | PEG1000 3 arm | |

Polymer Synthesis
Linear Polytriazole Synthesis
Method 8: Copper (II)

The dialkyne-drug-monomer (1.0 eq), a diazide co-monomer (1.0 eq) and sodium ascorbate (0.45 eq) were placed into a vial fitted with a stirrer bar and then sealed with a Suba-Seal®. Anhydrous DMF pre-purged with $N_2$ or argon was introduced into the vial and the mixture was stirred to form a clear solution under constant flow of inert atmosphere. An amount of catalyst stock solution (CuBr2 (14.2 mg) and PMDETA (11.0 mg) in 2 mL of DMF) was added into the mixture to give 0.15 eq of $CuBr_2$ and 0.15 eq. PMDETA in the final reaction mixture. The solution was stirred for 24 hours at room temperature under constant flow of $N_2$. At the end of the reaction, the solution was diluted with THF and passed through a column of neutral alumina. The column was washed further with THF followed by DCM to collect the remaining polymers. The solution was then concentrated to around 1 mL and then precipitated into diethyl ether to give the desired polymer upon drying in vacuo.

Method 9: Copper (I)

The dialkyne-drug-monomer (1 eq) and diazide co-monomer (1 eq) were placed into a 4 mL vial fitted with a stirrer bar and then sealed with a Suba-Seal®. 0.5 mL of toluene pre-purged with $N_2$ was introduced into the vial and the mixture was stirred to form a clear solution under constant flow of $N_2$. 0.2 mL of CuBr (0.15 eq) and PMDETA (0.15 eq) stock solution (20 mg/mL in toluene, stirred for 30 minutes under $N_2$ prior to use) was subsequently added into the reaction mixture and the solution was stirred for 24 hours, at room T under constant flow of $N_2$. At the end of the reaction, the solution was diluted with 3 mL of THF and passed through a column of neutral alumina. The column was washed further with 20 mL of THF to ensure all polymer were collected. The solution was then concentrated to around 1 mL and then precipitated into 40 mL of diethyl ether and dried in vacuo.

Method 10: Ruthenium Catalysed Click Reaction

The dialkyne-drug-monomer (1 eq), diazide comonomer (1 eq), and DMF were introduced into vial with a stirrer bar and then sealed with a Suba-Seal®. The solution was purged for 10 minutes with Argon before 14.7 mg of Cp*RuCl $(PPh_3)_2$ was added and the reaction heated at 35° C. under Argon for 24 hours. The reaction mixture was added dropwise to ethyl ether to precipitate the product before being dried in vacuo overnight.

Cross Linked Polytriazole Synthesis
Method 11: Cross-Linked or Hyper-Branched Polymer The dialkyne-drug-monomer (1 eq), a tetra-azide co-monomer (0.5 eq) or a tri-azide co-monomer (0.66 eq), Na ascorbate (0.45 eq) and DMF were introduced into a vial equipped with a magnetic stirrer bar. Catalyst stock solution (CuBr2 (14.2 mg) and PMDETA (11.0 mg) in 2 mL of DMF) was added into the mixture to give 0.15 eq of CuBr2 and 0.15 eq. PMDETA (in the final reaction mixture. The vial was sealed with a rubber septum, stirred at room temperature under nitrogen for 24 h. The resulting gel was dialysed in acetonitrile (3×1 L) and dried under high vacuum.

Method 12: Cross-Linked Rods and Bulk Polymer Synthesis

The dialkyne-drug-monomer (1 eq), a tetra-azide co-monomer (0.5 eq) or a triazide co-monomer (0.66 eq), Na ascorbate (0.45 eq) and DMF were introduced into a vial equipped with a magnetic stirrer bar and PTFE tubes (Ø=0.35 mm, I=10 mm, 100 tubes). Catalyst stock solution $(CuBr_2$ (14.2 mg) and PMDETA (11.0 mg) in 2 mL of DMF) was added into the mixture to give 0.15 eq. of and 0.15 eq. PMDETA in the final reaction mixture. The vial was sealed with a rubber septum, and degassing cycle (5 times nitrogen/vacuum cycles) were done to remove the bubbles trapped inside the tubes. The solution was subsequently stirred at room temperature under nitrogen for 24 h during which time gels formed. The tubes were separated from the bulk gels and soaked in isopropanol for minimum 16 hours and the rods were pushed out from the tubes using 0.305 mm stylet/wire. The resulting rods were washed in acetonitrile (3×250 mL) and the bulk gels with 3×1 L acetonitrile for 24 hours and dried under high vacuum.

Method 13: Cross-Linked or Hyper-Branched Polymer—Ruthenium Catalysed

Dialkyne-drug-monomer ((1 eq.), tetra-azide comonomer (0.5 eq), and DMF were introduced into a vial with a stirrer bar and then sealed with a Suba-Seal®. The mixture was then purged with Argon for 5 minutes before Cp*RuCl $(PPh_3)_2$ catalyst was added. The mixture was heated at 35° C. under Argon for 24 hours—before the temperature was raised to 50° C. for a second 24 hours. The resulting gel was dialysed in acetonitrile (3×1 L) and dried in vacuo overnight.

Method 14: Cross-Linked Rods and Bulk Polymer Synthesis Containing 2 Different Cross-Linkers The dialkyne-drug-monomer (1 eq), a tetra-azide co-monomer 1 (0.25 eq) and another tetra-azide co-monomer 2 (0.25 eq), Na ascorbate (0.45 eq) and DMF were introduced into a vial equipped with a magnetic stirrer bar and PTFE tubes (Ø=0.35 mm, I=10 mm, 100 tubes). Catalyst stock solution (CuBr2 (14.2 mg) and PMDETA (11.0 mg) in 2 mL of DMF) was added into the mixture to give 0.15 eq. of CuBr2 and 0.15 eq. PMDETA in the final reaction mixture. The vial was sealed with a rubber septum, and degassing cycle (5 times nitrogen/vacuum cycles) were done to remove the bubbles trapped inside the tubes. The solution was subsequently stirred at room temperature under nitrogen for 24 h to form gels. The tubes were separated from the bulk gels and soaked in isopropanol for minimum 16 hours and the rods were pushed out from the tubes using 0.305 mm stylet/wire. The resulting rods were washed in acetonitrile (3×250 mL) and the bulk gels with 3×1 L acetonitrile for 24 hours and dried under high vacuum.

Method 15: Cross-Linked or Hyper-Branched Polymer Containing Two Different Drug-Monomers Dialkyne-drug-monomer (1) (0.5 eq), and dialkyne-drug-monomer (2) (0.5 eq), a tetra-azide co-monomer (0.5 eq) or a tri-azide co-monomer (0.66 eq), Na ascorbate (0.45 eq) and DMF (were introduced in a vial equipped with a magnetic stirring bar. Catalyst stock solution (CuBr2 (14.2 mg) and PMDETA (11.0 mg) in 2 mL of DMF) was added into the mixture to give 0.15 eq of CuBr2 and 0.15 eq. PMDETA in the final reaction mixture. The vial was sealed with a rubber septum, stirred at room temperature under nitrogen for 24 h. The gel was dialysed in acetonitrile (3×1 L) and dried under high vacuum.

Method 16: Polymer Conjugate Prepared with Diazide-Drug-Monomer.

The diazide-drug-monomer (1 eq.) and a dialkyne co-monomer (1 eq.) are dissolved in the solvent of choice. The solution is purged with argon for 30 minutes before copper (II) bromide $(CuBr_2)$ (0.05 mol eq.), PMDETA (0.05 mol eq.) and sodium ascorbate (0.15 mol eq.) are added into the solution. The heterogeneous mixture is stirred vigorously overnight at room temperature until complete consumption of starting materials, as indicated by TLC. The mixture is diluted with water and any precipitate that forms is collected. Purification of the product by precipitation from DMF and further purification on Sephadex LH-20 gives the title drug-polymer conjugate. The drug-polymer conjugates are analysed by IR, $^1$H NMR and $^{13}$C NMR and GPC Method 17: Linear Click Polymer Conjugate Prepared with Dialkyne-Drug-Monomer with Additives.

The dialkyne-drug-monomer and diazide co-monomer 1 and co-monomer 2 are dissolved in the solvent of choice while keeping an equimolar ratio between the number of alkyne units and azide units. The solution is purged with argon for 30 minutes before copper (II) bromide (CuBr$_2$) (0.05 mol eq.), PMDETA (0.05 mol eq.) and sodium ascorbate (0.15 mol eq.) are added into the solution. The heterogeneous mixture is stirred overnight under argon atmosphere and at room temperature for 24 hours. The reaction mixture is then passed through a column of basic alumina to remove the CuBr$_2$ catalyst, and then concentrated in vacuo before being precipitated several times in excess of diethyl ether to afford the desired polymer a solid. The drug-polymerconjugates are analysed by $^1$H NMR and GPC.

Method 18: Polymer Conjugate Prepared with Alkyne-Azide-Drug-Agent Conjugate Monomer (Drug Monomer Only)

The alkyne-azide drug-monomer (1 eq.) is dissolved in the solvent of choice. The solution is purged with argon for 30 minutes before copper (II) bromide (CuBr$_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title drug-polymer conjugate. The drug-polymer conjugates are analysed by IR, $^1$H NMR and $^{13}$C NMR and GPC Method 19: Polymer Conjugate Prepared with Alkyne-Azide-Drug-Monomer (and Co-Monomer)

The alkyne-azide-drug-monomer (1 eq.) and an alkyne-azide co-monomer (1 eq.) are dissolved in the solvent of choice. The solution is purged with argon for 30 minutes before copper (II) bromide (CuBr$_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title drug-polymer conjugate. The drug-polymer conjugates are analysed by IR, $^1$H NMR and $^{13}$C NMR and GPC.

Using the above methods the following polymers in Table 6 were prepared.

TABLE 6

Examples of Click Polymers

| Example | Drug | Drug-monomer 1 (mg) | Co-Monomer 1 (mg) | Co-Monomer 2 (mg) | ProductionMethod (solvent) | Characterisation |
|---|---|---|---|---|---|---|
| 53 | LTP | Example 6 (73.7) | Example 40 (156.4) | — | 11/12 (DMF) | N/A Cross-linked hydrogel |
| 54 | LTP | Example 6 (157.7) | Example 43 (327.2) | — | 11/12 (DMF) | N/A Cross-linked hydrogel |
| 55 | LTP | Example 6 (157.3) | Example 42 (321.6) | — | 11/12 (DMF) | N/A Cross-linked hydrogel |
| 56 | LTP | Example 6 (211.4) | Example 41 (439.1) | — | 11/12 (DMF) | N/A Cross-linked hydrogel |
| 57 | LTP | Example 6 (105.8) | Example 45 (224.9) | — | 11/12 (DMF) | N/A Cross-linked hydrogel |
| 58 | LTP | Example 6 (105.7) | Example 40 (106.9) | Example 49 (113.4) | 14 (DMF) | N/A Cross-linked hydrogel |
| 59 | LTP | Example 6 (105.8) | Example 36 (205.8) | — | 11/12 (DMF) | N/A Cross-linked hydrogel |
| 60 | LTP | Example 8 (139.7) | (N3-PEG500)4-C (182.1) | — | 11/12 (DMF) | N/A Cross-linked hydrogel |
| 61 | LTP | Example 6 (106.6) | (N3-PEG500)4-C (91.4) | Example 40 (108.0) | 14 (DMF) | N/A Cross-linked hydrogel |
| 62 | LTP | Example 6 (122.6) | Example 46 (255.6) | — | 11/12 (DMF) | N/A Cross-linked hydrogel |
| 63 | LTP | Example 6 (122.3) | (N3-PEG500)4-C (105.9) | Example 46 (128.0) | 14 (DMF) | N/A Cross-linked hydrogel |
| 64 | LTP | Example 6 (122.5) | Example 49 (132.0) | Example 46 (128.0) | 14 (DMF) | N/A Cross-linked hydrogel |
| 65 | LTP | Example 7 (105.9) | (N3-PEG500)4-C (133.3) | — | 11/12 (DMF) | N/A Cross-linked hydrogel |
| 66 | LTP | Example 6 (211.4) | Example 49 (457.4) | — | 11/12 (DMF) | N/A Cross-linked hydrogel |

TABLE 6-continued

Examples of Click Polymers

| Example | Drug | Drug-monomer 1 (mg) | Co-Monomer 1 (mg) | Co-Monomer 2 (mg) | ProductionMethod (solvent) | Characterisation |
|---|---|---|---|---|---|---|
| 67 | LTP | Example 6) (109.9) | Example 49 (116.2) | — | 11/12 (DMF) | N/A Cross-linked hydrogel |
| 68 | LTP | Example 6 (76.5) | Example 49 (79.1) | — | 11/12 (DMF) | N/A Cross-linked hydrogel |
| 69 | LTP | Example 6 (74.6) | $(N_3\text{-}PEG_{500})_4\text{-}C$ (128.7) | — | 11/12 (DMF) | N/A Cross-linked hydrogel |

Using the above methods the following co-monomers in Table 7 may also be prepared.

TABLE 7

| Ex. | Structure | PEG used |
|---|---|---|
| 70 | 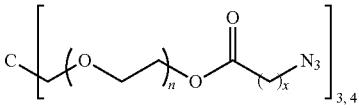 with x = 6 to 12 | PEG2000 PEG1000 PEG800 PEG450 |
| 71 | 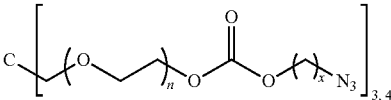 with x = 1 to 12 | PEG2000 PEG1000 PEG800 PEG450 |
| 72 | 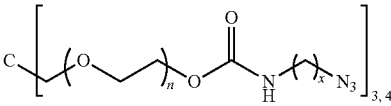 with x = 1, 4 to 12 | PEG2000 PEG1000 PEG800 PEG450 |
| 73 | 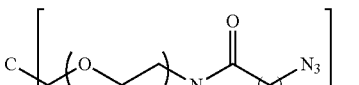 with x = 1 to 12 | PEG2000 PEG1000 PEG800 PEG450 |
| 74 | 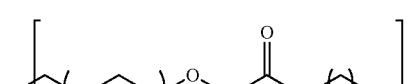 with x = 1 to 12 | PEG2000 PEG1000 PEG800 PEG450 |
| 75 | 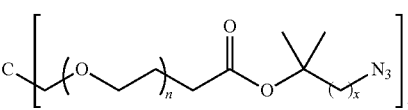 with x = 1 to 12 | PEG2000 PEG1000 PEG800 PEG450 |
| 76 | 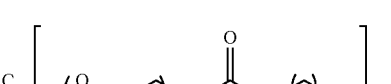 with x = 1 to 12 | PEG2000 PEG1000 PEG800 PEG450 |

Using the above methods the following polymers in Table 8 may also be prepared.

TABLE 8

| Example | Drug | Drug-monomer conjugate | Co-Monomer 1 | Co-Monomer 2 | Method of Synthesis |
|---|---|---|---|---|---|
| 77 | LTP | Example 6 | PEG400diN3 | — | 8 |
| 78 | LTP | Example 6 | PEG1000diN3 | — | 8 |
| 79 | LTP | Example 6 | PEG2000diN3 | — | 8 |
| 80 | LTP | Example 6 | PEG1000diN3 | — | 10 |
| 81 | LTP | Example 6 | (N3-PEG500)4-C | — | 13 |
| 82 | LTP | Example 6 | Example 40 | — | 13 |
| 83 | LTP | Example 7 | (N3-PEG500)4-C | — | 13 |
| 84 | LTP | Example 7 | Example 40 | — | 11/12 |
| 85 | LTP | Example 7 | Example 46 | — | 11/12 |
| 86 | LTP | Example 7 | (N3-PEG500)4-C | Example 46 | 14 |
| 87 | TVP | Example 10 | (N3-PEG500)4-C | Example 46 | 14 |
| 88 | TAF | Example 11 | (N3-PEG500)4-C | Example 46 | 14 |
| 89 | BIM | Example 12 | (N3-PEG500)4-C | Example 46 | 14 |
| 90 | LTP | Example 6 | Example 70 | — | 11/12 |
| 91 | LTP | Example 6 | Example 70 | (N3-PEG500)4-C | 11/12 |
| 92 | LTP | Example 6 | Example 70 | Example 49 | 11/12 |
| 93 | LTP | Example 6 | Example 71 | — | 11/12 |
| 94 | LTP | Example 6 | Example 71 | (N3-PEG500)4-C | 11/12 |
| 95 | LTP | Example 6 | Example 71 | Example 49 | 11/12 |
| 96 | TVP | Example 10 | Example 38 | — | 11/12 |
| 97 | TVP | Example 10 | Example 39 | — | 11/12 |
| 98 | TVP | Example 10 | Example 40 | — | 11/12 |
| 99 | TVP | Example 10 | Example 40 | (N3-PEG500)4-C | 11/12 |
| 100 | TVP | Example 10 | Example 40 | Example 49 | 11/12 |
| 101 | TVP | Example 10 | Example 41 | — | 11/12 |
| 102 | TVP | Example 10 | Example 49 | Example 46 | 11/12 |
| 103 | TVP | Example 10 | Example 46 | — | 11/12 |
| 104 | TVP | Example 10 | Example 41 | (N3-PEG500)4-C | 11/12 |
| 105 | TVP | Example 10 | Example 41 | Example 49 | 11/12 |
| 106 | TVP | Example 10 | Example 46 | — | 11/12 |
| 107 | TVP | Example 10 | Example 70 | — | 11/12 |
| 108 | TVP | Example 10 | Example 70 | (N3-PEG500)4-C | 11/12 |
| 109 | TVP | Example 10 | Example 70 | Example 49 | 11/12 |
| 110 | TVP | Example 10 | Example 71 | — | 11/12 |
| 111 | TVP | Example 10 | Example 71 | (N3-PEG500)4-C | 11/12 |
| 112 | TVP | Example 10 | Example 71 | Example 49 | 11/12 |
| 113 | TAF | Example 11 | Example 38 | — | 11/12 |
| 114 | TAF | Example 11 | Example 39 | — | 11/12 |
| 115 | TAF | Example 11 | Example 40 | — | 11/12 |
| 116 | TAF | Example 11 | Example 40 | (N3-PEG500)4-C | 11/12 |
| 117 | TAF | Example 11 | Example 40 | Example 49 | 11/12 |

TABLE 8-continued

| Example | Drug | Drug-monomer conjugate | Co-Monomer 1 | Co-Monomer 2 | Method of Synthesis |
|---|---|---|---|---|---|
| 118 | TAF | Example 11 | Example 41 | — | 11/12 |
| 119 | TAF | Example 11 | Example 41 | (N3-PEG500)4-C | 11/12 |
| 120 | TAF | Example 11 | Example 41 | Example 49 | 11/12 |
| 121 | TAF | Example 11 | Example 46 | — | 11/12 |
| 122 | TAF | Example 11 | Example 70 | — | 11/12 |
| 123 | TAF | Example 11 | Example 49 | Example 46 | 11/12 |
| 124 | TAF | Example 11 | Example 46 | (N3-PEG500)4-C | 11/12 |
| 125 | BIM | Example 12 | Example 70 | — | 11/12 |
| 126 | BIM | Example 12 | Example 70 | (N3-PEG500)4-C | 11/12 |
| 127 | BIM | Example 12 | Example 70 | Example 49 | 11/12 |
| 128 | LTP | Example 13 | Example 38 | — | 11/12 |
| 129 | LTP | Example 13 | Example 39 | — | 11/12 |
| 130 | LTP | Example 13 | Example 40 | — | 11/12 |
| 131 | LTP | Example 13 | Example 40 | (N3-PEG500)4-C | 11/12 |
| 132 | LTP | Example 13 | Example 40 | Example 49 | 11/12 |
| 133 | LTP | Example 13 | Example 41 | — | 11/12 |
| 134 | LTP | Example 13 | Example 41 | (N3-PEG500)4-C | 11/12 |
| 135 | LTP | Example 13 | Example 41 | Example 49 | 11/12 |
| 136 | LTP | Example 13 | Example 46 | — | 11/12 |
| 137 | LTP | Example 13 | Example 70 | — | 11/12 |
| 138 | LTP | Example 13 | Example 70 | (N3-PEG500)4-C | 11/12 |
| 139 | LTP | Example 13 | Example 70 | Example 49 | 11/12 |
| 140 | LTP | Example 13 | Example 71 | — | 11/12 |
| 141 | LTP | Example 13 | Example 71 | (N3-PEG500)4-C | 11/12 |
| 142 | LTP | Example 13 | Example 71 | Example 49 | 11/12 |
| 143 | LTP | Example 13 | Example 49 | Example 46 | 11/12 |
| 144 | LTP | Example 13 | Example 46 | (N3-PEG500)4-C | 11/12 |

Drug Release Method

Polymer samples were tested for in vitro drug release following guidelines recommended by the International Organisation of Standardisation. The samples were placed onto a wire mesh folded into an M shape and suspended in isotonic phosphate buffer (IPB) pH 7.4 or pH 8.4 (Table 1), and stirred at 37° C. or 55° C. Aliquots of the receptor solution were collected at pre-determined time points until the drug was depleted from the polymer.

In-Vitro Release Sample Preparation 15 mL of isotonic phosphate buffer (pH 7.4) was added to approximately 10 mg of bulk polymer material and allowed to stir in a 37° C. water bath in the absence of light. 100 µL aliquots of each sample were removed at defined time points. 100 µL of isotonic phosphate buffer was replaced back into each sample after each aliquot removal. The amount of drug in the aliquots was quantified by reverse phase high performance liquid chromatography (HPLC) coupled with UV detection. Analytes were separated on a C18 column with a solvent mixture as outlined for each drug class in Table 9 below.

TABLE 9

| Assay | Column | Mobile Phase | Flow rate (mL/min) | Wavelength (nm) | Retention time (min) |
|---|---|---|---|---|---|
| 1: Latanoprost free acid: | Kinetex® XB C18 150 × 4.6 mm; 5 µm, 100 Å | Acetonitrile:water 38:62 pH 3.0 (adjusted with phosphoric acid) | 1.0 | 210 | 7.0 |
| 2: Bimatoprost | Kinetex® EVO C18 150 × 4.6 mm; 5 µm, 100 Å | Acetonitrile: 0.1% TEA in water 37:63 pH 6.0 (adjusted with acetic acid) | 1.0 | 210 | 20.0 |

Degradation Sample Preparation

In Vitro Degradation of Cross-Linked Polymers

A degradation sample consists of three to four rods of cross-linked polymer (total polymer mass=0.5 to 1.1 mg) wrapped in a stainless-steel mesh, placed in an amber glass vial filled with 15 mL of isotonic phosphate buffer (pH 7.4) and equipped with a stir bar and a PTFE/silicone septum screw cap. The initial mass of both mesh and rods is recorded.

Ten to twelve of these samples were placed in a thermostatted water bath at either 37° C. or 55° C., equipped with a multi-stirring plate. The samples are stirred at 300 rpm at the required temperature and a sample is removed at pre-determined time points. The polymer is removed from the sample and the mesh with the rods was washed twice with milliQ water and dried under vacuum. The rods were weighed. When rods could not be removed from the mesh (rods stuck), the mesh with rods was weighed. In addition, the drug concentration of the buffer was measured by HPLC.

The amount of drug release from samples undergoing biodegradation was also determined. 100 µL aliquots of each sample were removed at defined time points. The amount of drug in the aliquots was quantified by reverse phase high performance liquid chromatography (HPLC) coupled with UV detection, as outlined below.

In Vitro Degradation of Linear Polymers

A degradation sample consists of carefully weighed polymer (~10 mgs) placed in an 8 mL vial filled with 5 mL of isotonic phosphate buffer (pH 7.4) and equipped with a stir bar and a PTFE/silicone septum screw cap. Four to five samples of each polymer were placed in a thermostatted water bath at either 37° C. or 55° C., equipped with a multi-stirring plate. The samples are stirred at 300 rpm at the required temperature and a sample is removed at pre-determined time points. 100 µL aliquots were removed from each sample and the amount of drug in the aliquots was quantified by reverse phase high performance liquid chromatography (HPLC) coupled with UV detection, as outlined below. The remaining solution was dried in a freeze dryer for 72 hours. Gel permeation chromatography (GPC) analysis was done on each sample to analyse the molecular weight of the polymer.

GPC Analysis:

Gel permeation chromatography (GPC) analysis of the polymer samples was performed on Shimadzu liquid chromatography system equipped with a Shimadzu RID-10A differential refractive index detector ($\lambda$=633 nm) and Shimadzu SPD-20A ultraviolet detector connected to a 5.0 µm bead-size guard column (50×7.8 mm) followed by three Shodex KF-805L columns (300×8 mm, bead size: 10 µm, pore size maximum: 5000 Å) in series operating at 40° C. The eluent was N,N-dimethylacetamide (HPLC grade, with 0.03% w/v LiBr) and running at 1 mL/min. A molecular weight calibration curve was produced using polystyrene standards with narrow molecular weights distribution ranging from 500 to $2 \times 10^6$ Da.

The amount of drug release from samples undergoing biodegradation was also determined. 100 µL aliquots of each sample were removed at defined time points. The amount of drug in the aliquots was quantified by reverse phase high performance liquid chromatography (HPLC) coupled with UV detection, as outlined below.

TABLE 10

Drug release from polymers.

| Example no. | Buffer pH for release study | Drug | Rate [μg/10 mg/24 hrs] |
|---|---|---|---|
| 66 | 7.4 | Latanoprost free acid | 11.73 |
| 53 | 7.4 | Latanoprost free acid | 7.52 |
| 67 | 7.4 | Latanoprost free acid | 2.61 |
| 68 | 7.4 | Latanoprost free acid | 3.18 |
| 59 | 7.4 | Latanoprost free acid | 74.34 |
| 60 | 7.4 | Latanoprost free acid | 9.73 |
| 56 | 7.4 | Latanoprost free acid | 13.42 |
| 57 | 7.4 | Latanoprost free acid | 28.25 |
| 54 | 7.4 | Latanoprost free acid | 85.78 |
| 58 | 7.4 | Latanoprost free acid | 10.35 |
| 62 | 7.4 | Latanoprost free acid | 7.34 |
| 63 | 7.4 | Latanoprost free acid | 12.09 |
| 64 | 7.4 | Latanoprost free acid | 10.24 |
| 65 | 7.4 | Latanoprost free acid | 2.99 |

Dog IOP and Pupil Size Study Method

The in vivo performance of select drug polymer conjugates were studied in purpose bred dogs (*Canis lupus familiaris*), homozygous for the G661R missense mutation in ADAMTS10, and therefore affected with primary angle glaucoma.

The needle containing a rod-shaped implant of the selected conjugate was inserted into the anterior chamber at the limbus by penetrating the conjunctiva, sclera and cornea. The needle was moved as far as possible into the anterior chamber so that its tip was close to the inferior iridocorneal angle. The implant was expelled from the needle and placed into the inferior iridocorneal angle by moving a stylet inside the needle towards the needle tip. The needle was then removed from the anterior chamber and the conjunctiva around the injection site held off with forceps for 1-2 minutes to minimize leakage of aqueous humour.

The measurement of diurnal intraocular pressure (IOP) was performed by means of a rebound tonometer (TONOVET™; Icare Finland Oy, Vantaa, Finland) on awake, unsedated dogs. IOP measurements taken at 8 am, 12 μm, and 4 μm and the mean of all measurements was also calculated in order to determine the mean diurnal IOP.

Pupil diameter was measured by means of Jameson™ calipers. Pupil sizes were assessed at the same time points as IOP measurements (08:00, 12:00, and 16:00) and immediately following the tonometry. The room light was turned off, and a red LED headlight used to visualize the fundic reflection for outline of the pupil by retroillumination. Pupil sizes for measurements at 8 am, 12 μm, and 4 μm were used to calculate the average pupil size.

Example 150

Discussion of Drawings

Referring to the drawings the figures show specific examples demonstrating the effect of variation in the monomers and the presence of biodegradable groups such as each of the monomer of formula (IVa) and the monomer of formula (V) when (VIa, b, c or d) are present.

In FIG. 1 the plots show the cumulative release (μg/10 mg) of latanoprost free acid with time exposed to isotonic phosphate buffer (pH 7.4) at 37.0° C. from drug-polymer conjugates with a common backbone segment Q to the Example drug-polymer conjugates but different chemistry in and around the segment Q. Example 60 (n-alkyl ester) and Example 65 (α, α-dimethyl ester) are derived from a common 4-arm PEG500 azide co-monomer but have different ester moieties at Q-X. Shows that the same zero-order release rate is consistently achieved despite the Q-X chemistry differences and that the linker chemistry can be used to vary the rate of drug release. Drug-polymer conjugates of Example 60 and Example 65 were produced. Both compositions of a stoichiometric product of a latanoprost free acid drug monomer and a common 4-arm PEG500 azide,

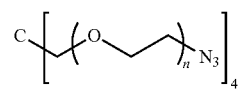

co-monomer. The structures of the respective drug monomers are:

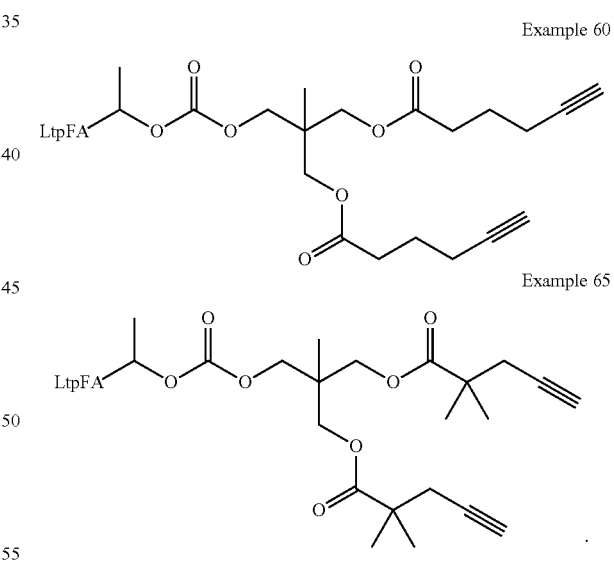

In both cases the rate of drug release is shown (refer FIG. 1) to be zero-order, which provides a product that delivers a constant daily dose for the entire treatment period. The actual dose per day can be selected by controlling the weight of product administered. Furthermore, the rate of release of latanoprost free acid varies providing products with different treatment periods.

Figure 2:
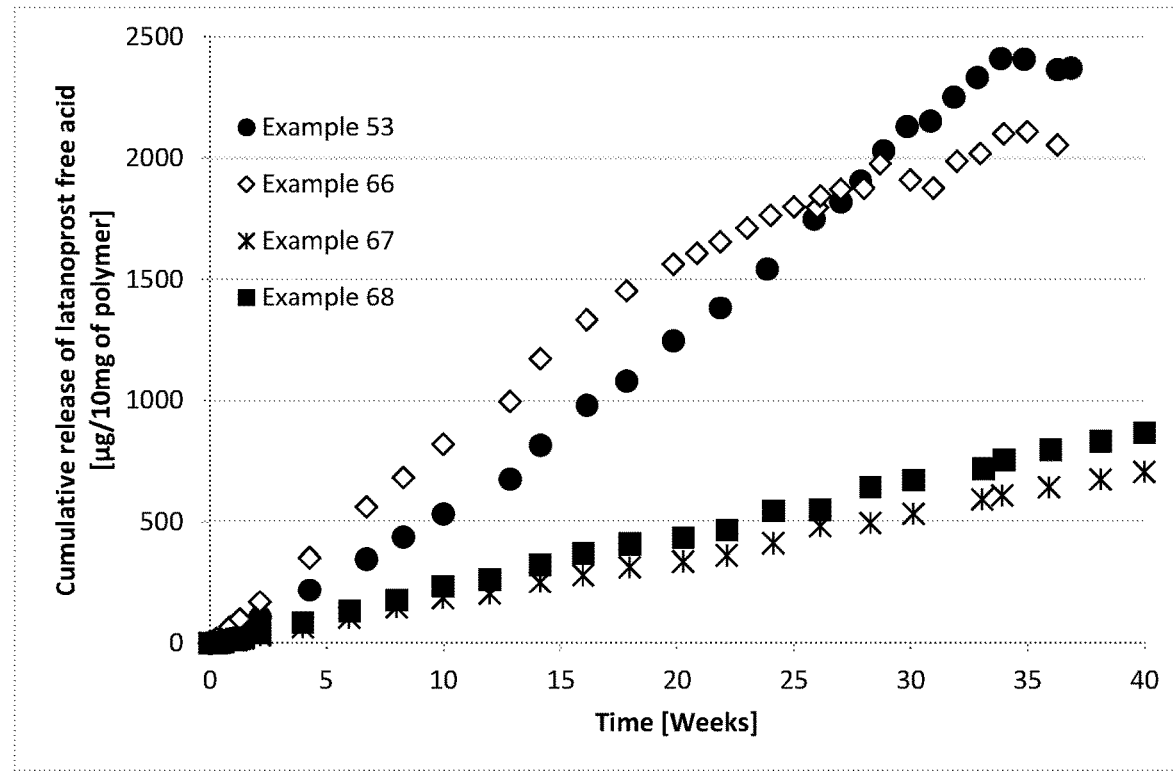
FIG. 2 is a graph including four plots comparing the cumulative release (μg/10 mg) of latanoprost free acid with time exposed to isotonic phosphate buffer (pH 7.4) at 37.0° C. and 55.0° C., respectively of drug-polymer conjugates of Examples 53 and 66 with drug polymer conjugates of Examples 67 and 68.

In FIG. 2 the plots show the cumulative release (μg/10 mg) of latanoprost free acid with time exposed to isotonic phosphate buffer (pH 7.4) at 37.0° C. and 55.0° C., respectively, from drug-polymer conjugates with linker (L) common to the Example drug-polymer conjugates but different co-monomers. Example 53 and Example 66 have proportionally greater PEG content with respect to drug-monomer compared with Example 67 and Example 68, showing that PEG content can be used to vary rate of drug release even with different polymer chemistry. Example 53 and Example 66 use the same PEG content but different Q-X components in the drug monomer, an ester and carbamate respectively, showing that the linker (L) of the prostaglandin to the backbone is the predominant determinant of rate of drug release rather than changes to chemistry of Q-X. Example 67 and Example 68 have the same chemical composition but with Example 68 of higher cross-linking density, showing that cross-linking density does not have a significant effect on rate of drug release.

Drug-polymer conjugates of Example 53, Example 66, Example 67 and Example 68 were produced. The composition of all 4 examples are derived from a common latanoprost free acid drug monomer, Example 6:

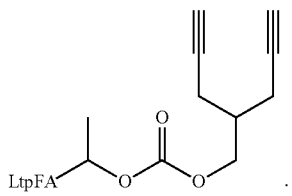

Example 67 and Example 68 are both compositions of a stoichiometric product of Example 6 and a common 4-arm PEG200 azide

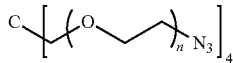

L 4 co-monomer. Example 67 was produced with the reactants at a 0.09M concentration and Example 68 with the reactants at a concentration of 0.18M to ensure Example 68 has a higher cross-linking density. Example 53 is a composition of a stoichiometric product of Example 6 and the co-monomer 4-arm PEG500 ester azide,

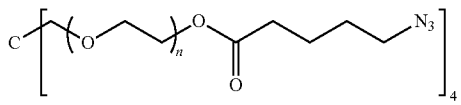

whereas, Example 66 is a composition of a stoichiometric product of Example 6 and the co-monomer 4-arm PEG500 carbamate azide,

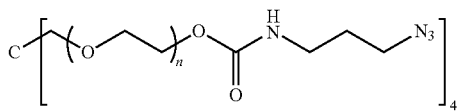

In all cases the rate of drug release is shown (FIG. 2) to be zero-order to provide a product that delivers a constant daily dose for the entire treatment period. The actual dose per day can be selected by controlling the weight of product administered. Example 53 and Example 66 use the same PEG content but different Q-X components in the drug monomer, an ester and carbamate respectively, showing that the linker (L) is the predominant determinant of rate of drug release rather than changes to chemistry of Q-X. Example 53 and Example 66 have proportionally greater PEG content with respect to drug-monomer compared with Example 67 and Example 68, showing that PEG content can be used to vary rate of drug release even with different polymer chemistry. Example 67 and Example 68 have the same chemical composition but with Example 68 of higher cross-linking density, showing that cross-linking density does not have a significant effect on rate of drug release.

Figure 3:
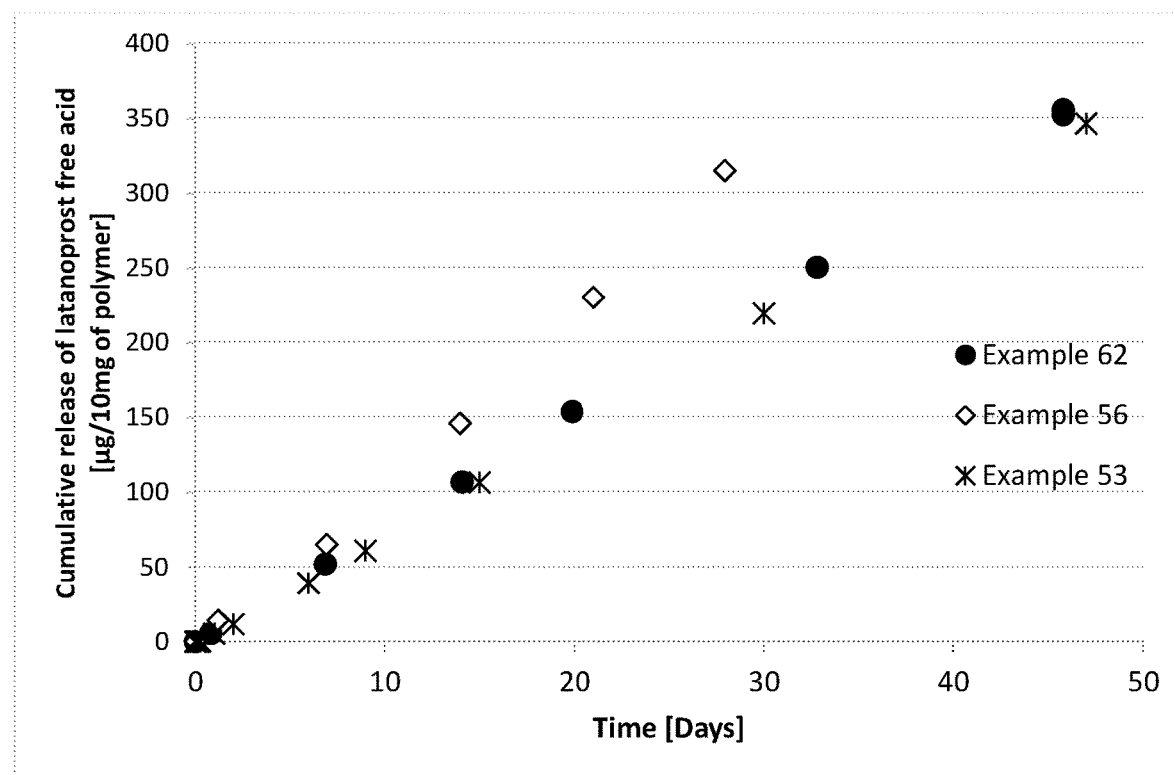
FIGS. 3(a) and 3(b) include two graphs (a) and (b) showing: a) cumulative release (μg/10 mg) of latanoprost free acid, and b) % mass loss with time exposed to isotonic phosphate buffer (pH 7.4) at 37.0° C. from drug-polymer conjugates with different co-monomers of Example 56, Example 53 and Example 62 which are derived from the same drug-monomer.
Figure 3:
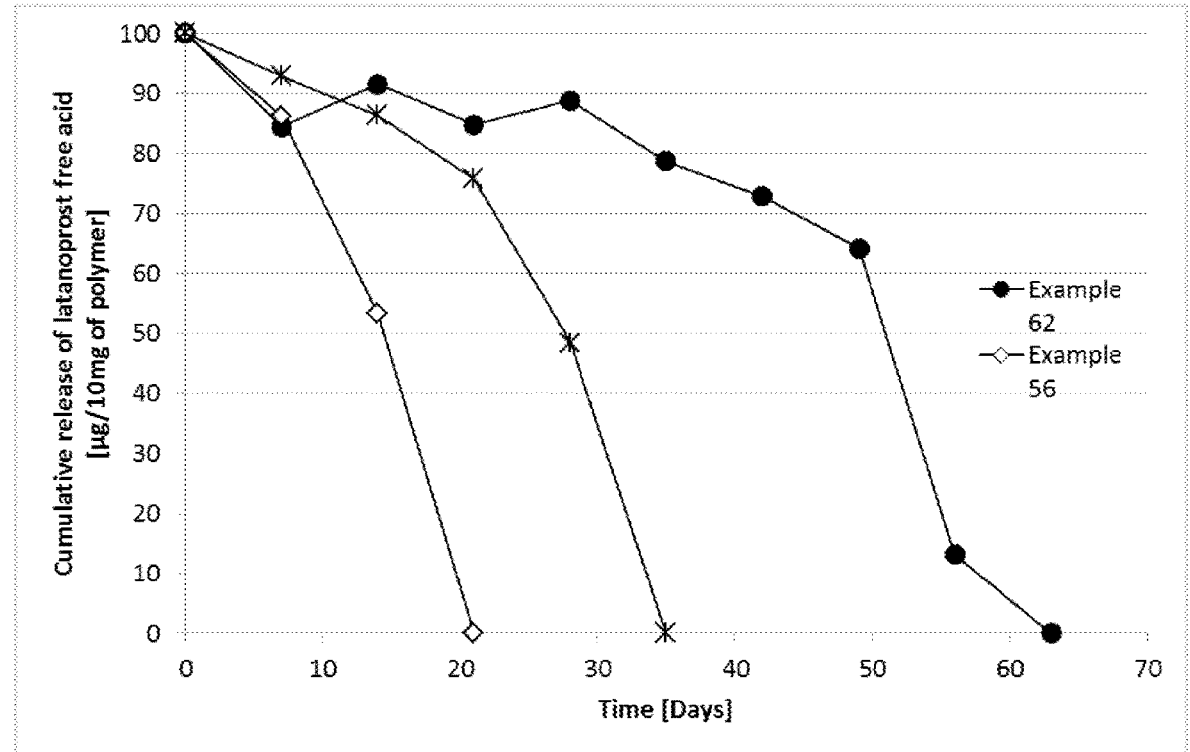

In FIG. 3 the plots show a). cumulative release (μg/10 mg) of latanoprost free acid, and b). % mass loss with time exposed to isotonic phosphate buffer (pH 7.4) at 37.0° C. from drug-polymer conjugates with linker (L) common to the Example drug-polymer conjugates but different co-monomers. Example 56, Example 53 and Example 62 are derived from the same drug-monomer, Example 6, but use 4-arm PEG500 azide co-monomer containing an n-alkyl ester and C3, C4 and C5 methylene chains about the ester, respectively. The release rates do not vary significantly with changes to the n-alkyl ester of the co-monomer, whereas, the period until complete mass loss does vary. Furthermore, the mass loss is non-linear with very little loss initially but accelerating after a lag period. Such a profile allows a product to be produced to ensure very little mass loss during its treatment period with rapid mass loss after the treatment period. Drug-polymer conjugates of Example 56, Example 53 and Example 62 were produced. The composition of all 4 examples are derived from a common latanoprost free acid drug monomer, Example 6:

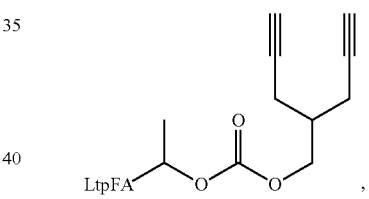

and 4-arm PEG200 azide co-monomers containing an n-alkyl ester with C3, C4 and C5 methylene groups about the ester. Following are the structures of the co-monomers used in each construct:

Example 56

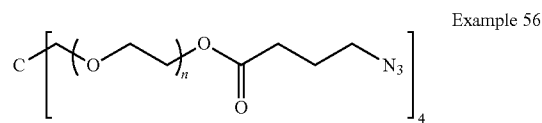

Example 53

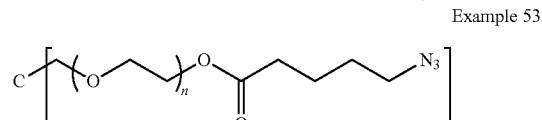

Example 62

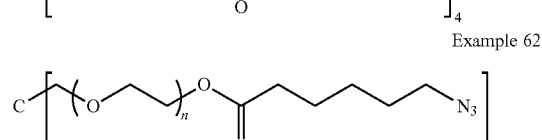

In all cases the rate of drug release (FIG. 4) is shown to be zero-order to provide a product that delivers a constant daily dose for the entire treatment period and that the release rates do not vary significantly with changes to the n-alkyl ester of the co-monomer despite significantly different chemical degradation rates (% mass loss with respect to exposure to isotonic phosphate buffer, pH 7.4, at 55.0° C.). The mass loss is non-linear with very little loss initially but accelerating after a lag period. Such a profile allows a product to be produced to ensure very little mass loss during its treatment period with rapid mass loss after the treatment period.

Figure 4:
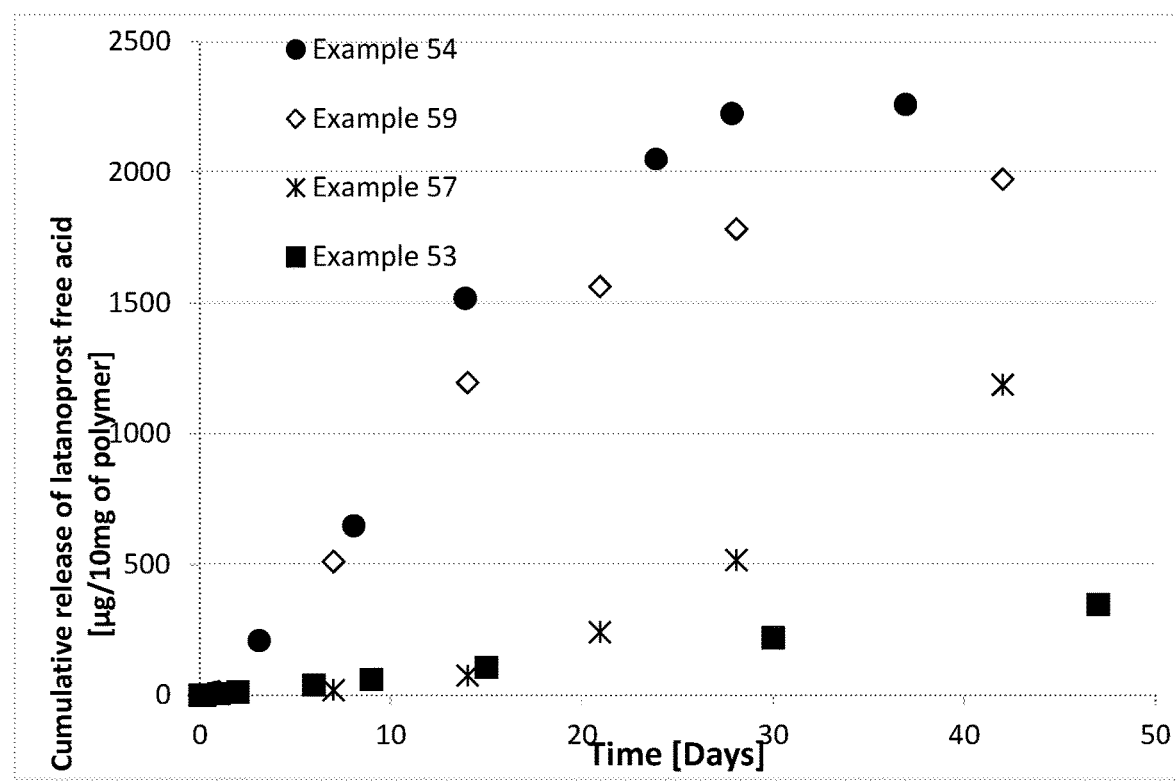
FIG. 4 is a graph with four plots showing the cumulative release (μg/10 mg) of latanoprost free acid with time exposed to isotonic phosphate buffer (pH 7.4) at 37.0° C. from drug-polymer conjugates with segment Q common to the Example drug-polymer conjugates but different co-monomers of Example 59, Example 57, Example 54 and Example 53 (for comparison).

In FIG. 4 the plots show the cumulative release (μg/10 mg) of latanoprost free acid with time exposed to isotonic phosphate buffer (pH 7.4) at 37.0° C. from drug-polymer conjugates with linker (L) common to the Example drug-polymer conjugates but different co-monomers. Example 59 and Example 57 comprise a common drug monomer and similar co-monomer that all use an ester with different R-groups alpha to the carbonyl of the ester. Example 54 uses an oxallyl moiety neighbouring to the carbonyl. These are compared with Example 53 that has no substituent R-group alpha to the carbonyl of a simple n-alkyl ester. The drug release rates for Example 54, Example 59 and Example 57 are rapid compared with Example 53. Such systems would be suitable for controlled drug delivery in applications that have a short treatment period. Drug-polymer conjugates of Example 54, Example 59 and Example 57 were produced to be compared with Example 53. The composition of all 4 examples are derived from a common latanoprost free acid drug monomer, Example 6:

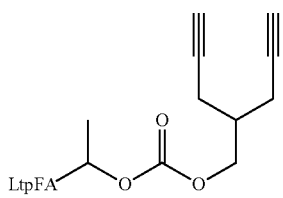

Example 53 uses a 4-arm PEG500 azide co-monomer containing an n-alkyl C4 ester

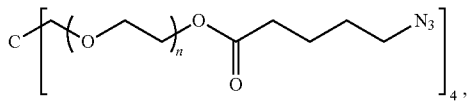

whereas, Example 54, Example 59 and Example 57 use a 4-arm PEG500 azide co-monomer containing a branched ester in a similar position with respect to the azide as Example 53. Following are the structures of the co-monomers used in each construct:

Example 54

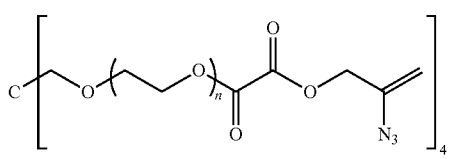

Example 59

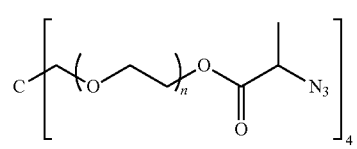

Example 57

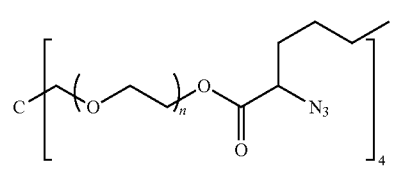

The drug release rates for Example 54, Example 59 and Example 57 are rapid compared with Example 53 (refer FIG. 4) and are noted to chemically biodegrade to a fully soluble product within 7-days. Such systems would be suitable for controlled drug delivery in applications that have a short treatment period.

Figure 5:
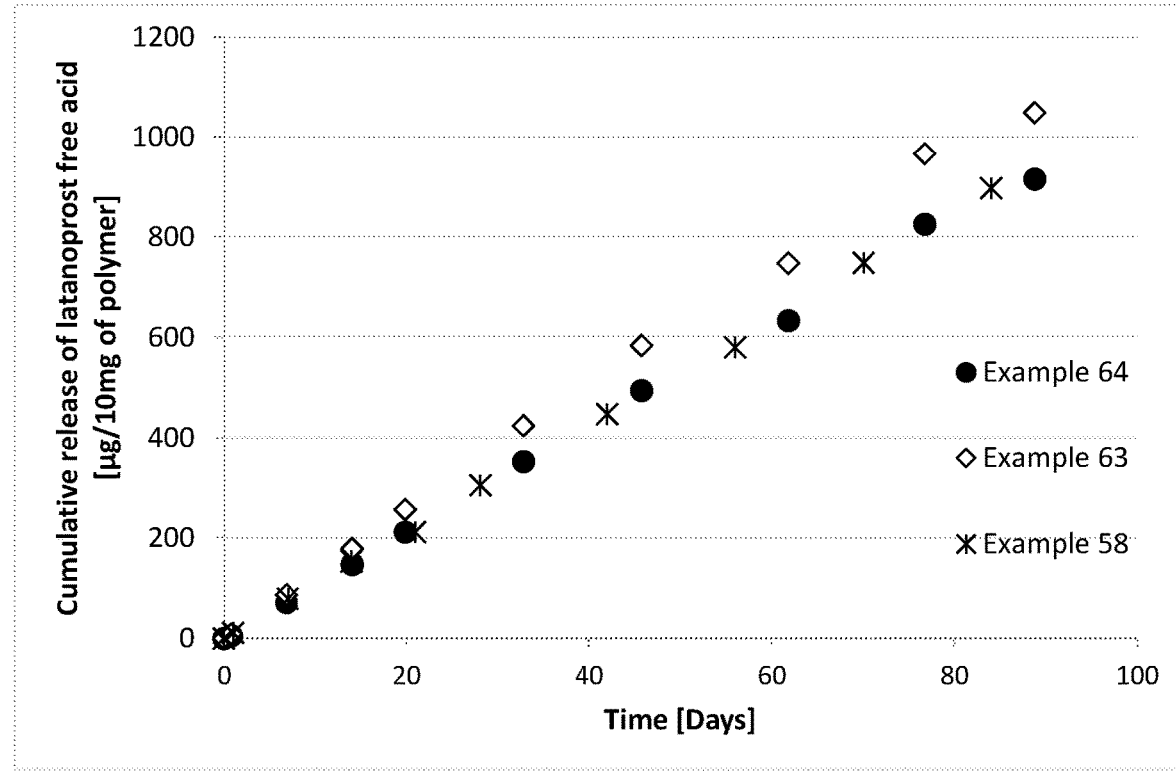
FIG. 5 is a graph having four plots showing the cumulative release (μg/10 mg) of latanoprost free acid with time exposed to isotonic phosphate buffer (pH 7.4) at 37.0° C. from drug-polymer conjugates. Example 63, Example 64 and Example 58 which have the same drug monomer and different comonomers.

In FIG. 5 the plots show the cumulative release (μg/10 mg) of latanoprost free acid with time exposed to isotonic phosphate buffer (pH 7.4) at 37.0° C. from drug-polymer conjugates with linker (L) common to the Example drug-polymer conjugates. Example 63, Example 64 and Example 58 comprise a common drug monomer and combinations of two co-monomers with different chemistries. Shows that the polymer chemistry can be altered to introduce other features (e.g. biodegradation) yet maintain the preferred drug release. Drug-polymer conjugates of Example 63, Example 64 and Example 58 were produced. The composition of all 4 examples are derived from a common latanoprost free acid drug monomer, Example 6:

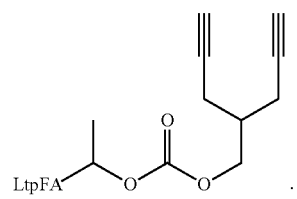

Following are the structures of the co-monomers used in for each construct:

Example 63

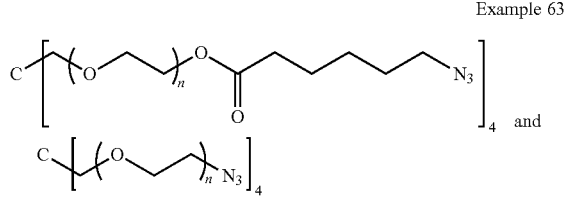
and

Example 64

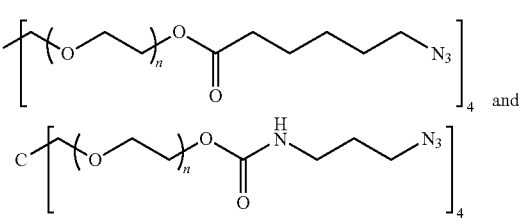
and

Example 58

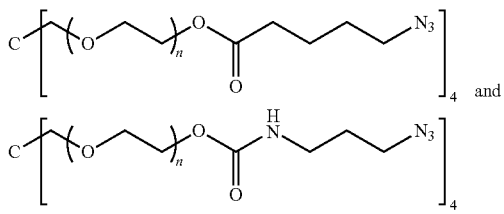

For each construct the composition comprises an equal molar ratio of each of the co-monomers in stoichiometric amounts with the drug monomer, Example 6. The drug release rates for Example 63, Example 64 and Example 58 are comparable (refer FIG. 5) and show that the polymer chemistry can be altered to introduce other features (e.g. biodegradation) yet maintain the preferred drug release rate.

Figure 6:
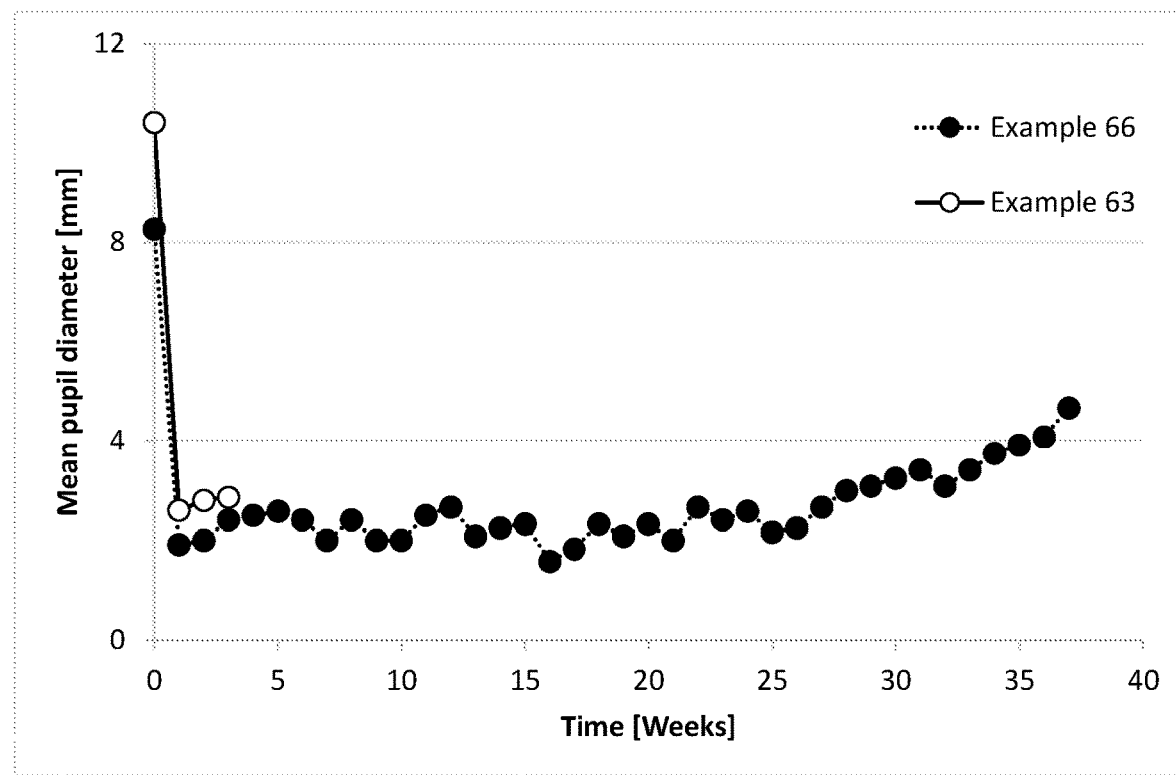
FIG. 6 is a graph having two plots showing the miotic pupil response (mm) in dog eyes treated with polymer-prostaglandin conjugates of Example 66 and Example 63.

In FIG. 6 the plots show the miotic pupil response (mm) in dog eyes treated with Example 66 and Example 63 each with a common drug monomer segment Q. These results demonstrate therapeutic levels of drug (latanoprost free acid) are released. Rod-shaped implants of Example 66 and Example 63 were produced suitable for administration to dogs with a 27G needle. The implant were administered to the dogs and pupil size (mm) measured. Dog pupils show a miotic response to a prostaglandin analogue. The pupil response was measured weekly following administration (refer FIG. 6). In both cases therapeutic concentrations of the prostaglandin analogue, latanoprost free acid, was shown to be released during the near-zero order release period as indicated by a pupil size less than 4 mm. In the case of Example Example 66 the pupil response was shown to diminish at about 37 weeks, which coincides with depletion of the latanoprost free acid from the material following an extended period of drug release. Such a result demonstrates that the chemistry of the linker (L) can be used to vary the treatment period of the product.

Figure 7A:
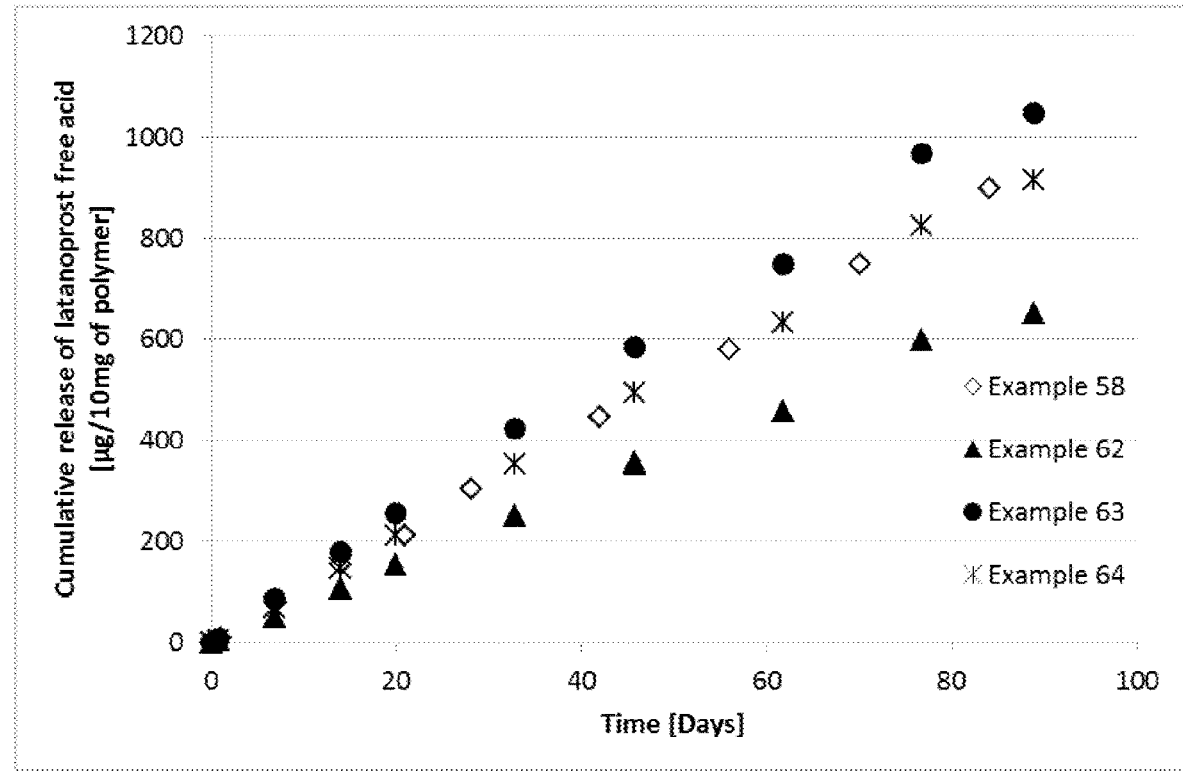
FIGS. 7a and 7(b) include two graphs (a) and (b) showing a). cumulative release (μg/10 mg) of latanoprost free acid, and b). % mass loss with time exposed to isotonic phosphate buffer (pH 7.4) at 37.0° C. and 55.0° C., respectively, from drug-polymer conjugates of Example 58, Example 62, Example 63 and Example 64.
Figure 7:
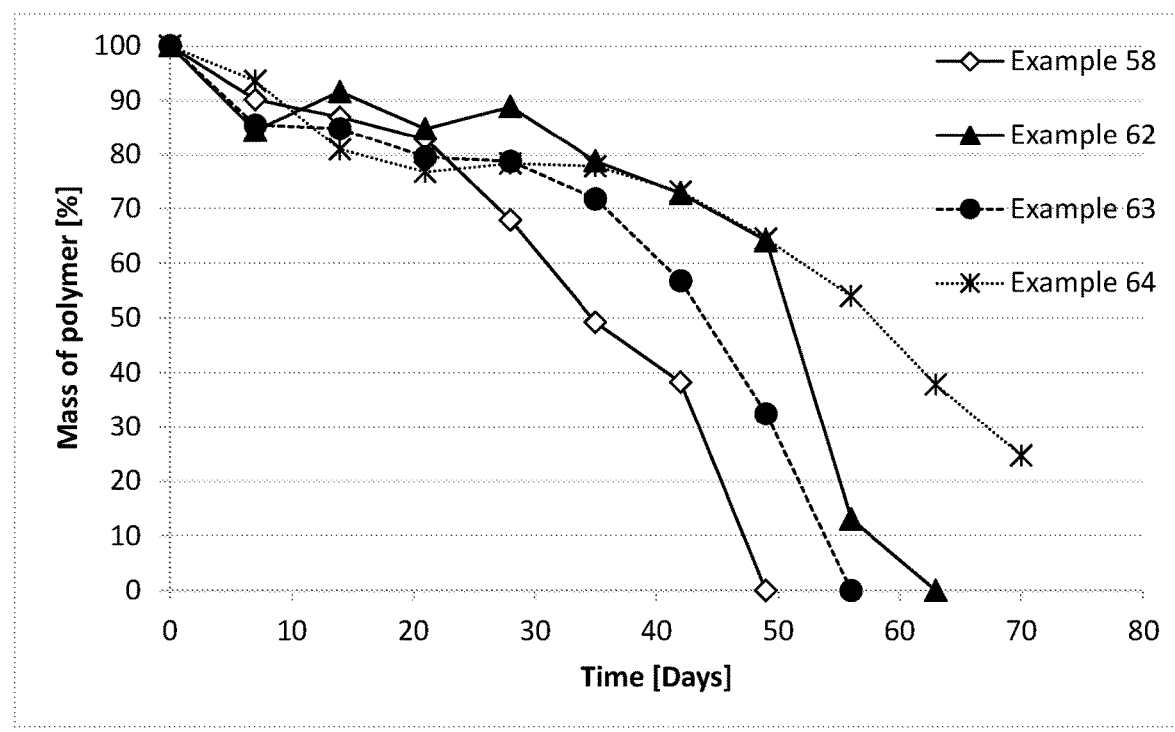

In FIG. 7 the plots showing a) cumulative release (μg/10 mg) of latanoprost free acid, and b) % mass loss with time exposed to isotonic phosphate buffer (pH 7.4) at 37.0° C. and 55.0° C., respectively, from preferred Examples drug-polymer conjugates. Example 58, Example 62, Example 63 and Example 64 are derived from the same drug-monomer, Example Example 6, but use different 4-arm PEG azide co-monomers. The release rates do not vary significantly with changes to the co-monomer, whereas, the period until complete mass loss does vary. Furthermore, the mass loss is a preferred non-linear profile with a predicted period until complete mass loss in a mammalian eye of a preferred period of between 20 weeks and 45 weeks. Drug-polymer conjugates of Example 58, Example 62, Example 63 and Example 64 were produced. The composition of all 4 examples are derived from a common latanoprost free acid drug monomer, Example 6:

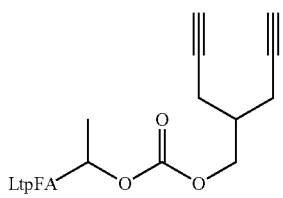

Following are the structures of the co-monomers used in each construct:

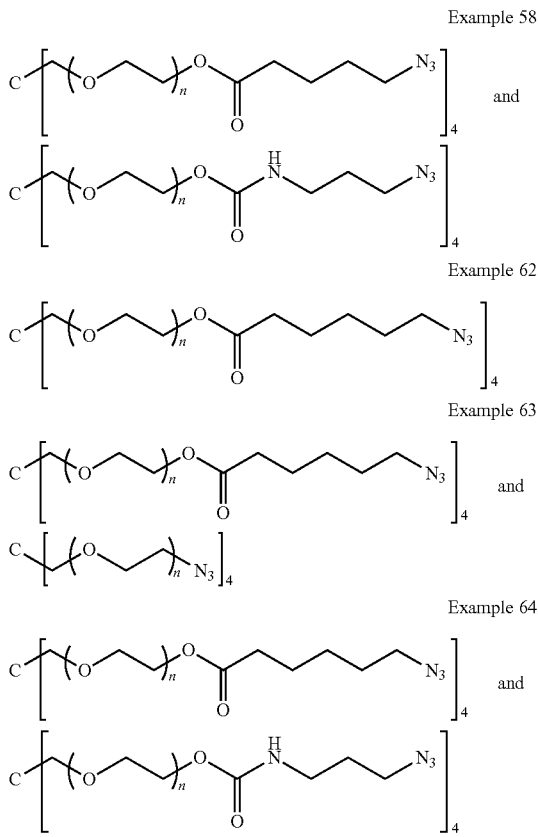

For each construct the composition comprises an equal molar ratio of each of the co-monomers in stoichiometric amounts with the drug monomer, Example 6.

In all cases the rate of drug release (FIG. 7) is shown to be zero-order to provide a product that delivers a constant daily dose for the entire treatment period and that the release rates do not vary significantly with changes to the chemistry of the polymer from use of the different co-monomers. Furthermore, the mass loss is a preferred non-linear profile with a predicted period until complete mass loss in a mammalian eye of a preferred period of between 20 weeks and 45 weeks. Such a profile allows a product to be produced to provide a preferred effective treatment period of between 20 and 45 weeks.

The invention claimed is:

1. A polymer-prostaglandin analogue conjugate comprising:
a polymer backbone comprising a plurality of moieties of formula (I):

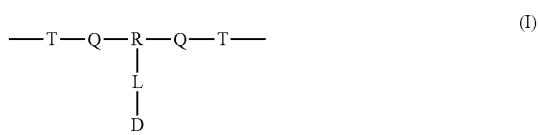

wherein:

T represents a triazole moiety;

Q is independently selected at each occurrence and may be present or absent and when present is a linking group selected from linking group Q of the following formulae Q-X, wherein X represents linkage to T and m is an integer from 0 to 10:

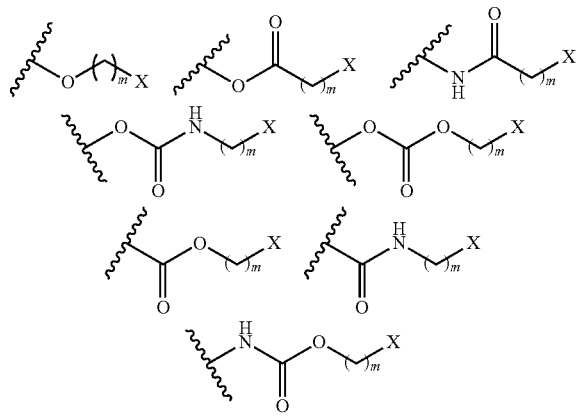

R is a linear or branched hydrocarbon;

L is a group of formula (II):

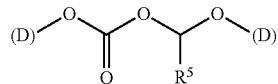

(II)

wherein:

R⁵ is selected from hydrogen, methyl, ethyl, propyl, isopropyl, butyl, isobutyl, sec-butyl, and tert-butyl;

(R) indicates the point of attachment to R; and (D) indicates the point of attachment to D; and D is a prostaglandin analogue D of formula (Xb):

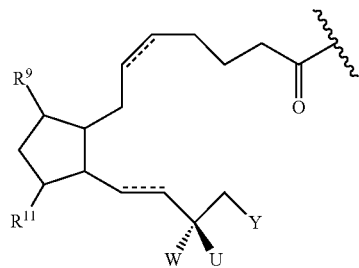

(Xb)

wherein:

⌇⌇⌇ represents the point of attachment of the prostaglandin analogue to L;

each ------ independently represents a double or single bond;

Y is an optionally substituted $C_4$ to $C_{10}$ hydrocarbyl group or optionally substituted $C_4$ to $C_{10}$ hydrocarbyloxy group;

$R^9$ and $R^{11}$ each are hydroxy; and

W is hydroxy and U is hydrogen, or W and U are both fluoro, or W and U together form an oxo moiety.

2. The polymer-prostaglandin conjugate of claim 1, wherein Q is absent.

3. The polymer-prostaglandin conjugate of claim 1, wherein m is an integer from 0 to 6.

4. The polymer-prostaglandin conjugate of claim 1, wherein D is selected from the group consisting of:

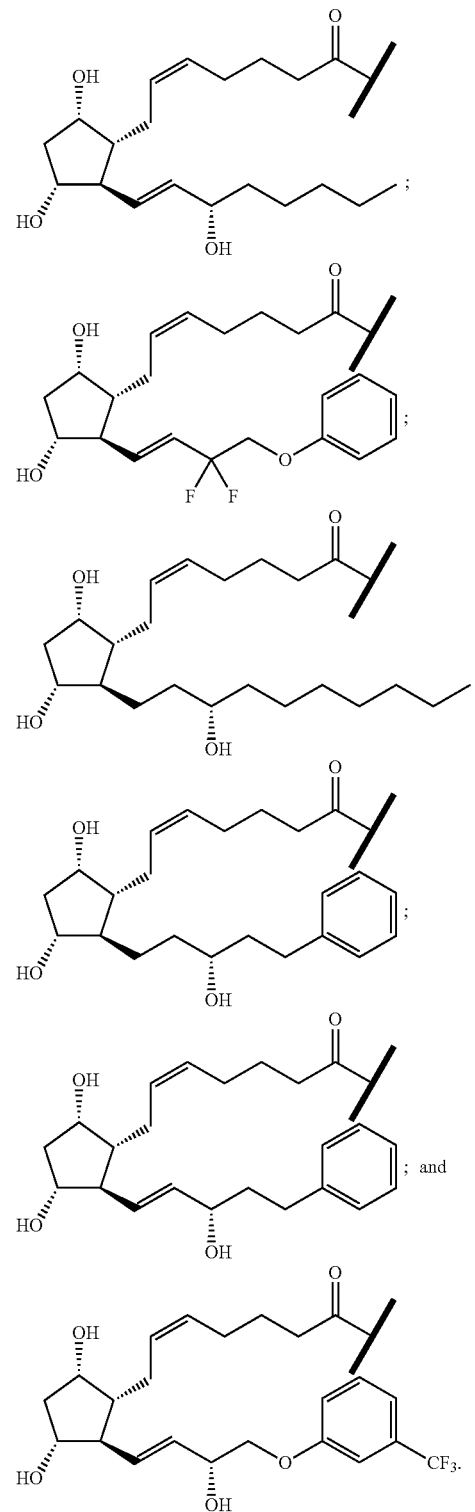

5. A polymer-prostaglandin analogue conjugate, wherein the conjugate is a copolymer of at least one monomer of formula (IV):

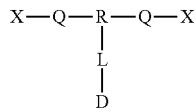

wherein:
X may be the same or different at each occurrence and represents a terminal functional group comprising an alkyne or an azide moiety;
Q is independently selected at each occurrence and may be present or absent and when present is a linking group selected from linking group Q of the following formulae Q-X, wherein m is an integer from 0 to 10:

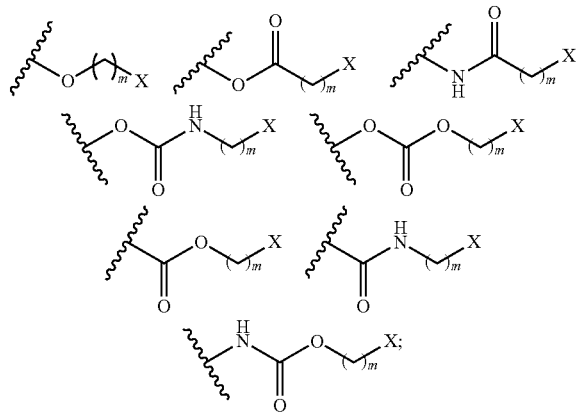

R is a linear or branched hydrocarbon;
D is a prostaglandin analogue of formula (Xb):

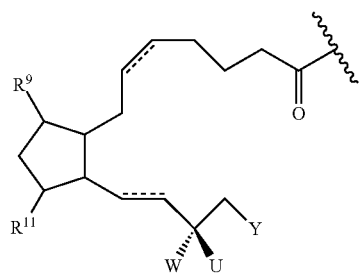

wherein:
~~~ represents the point of attachment of the prostaglandin analogue to L;
each ----- independently represents a double or single bond;
Y is an optionally substituted $C_4$ to $C_{10}$ hydrocarbyl group or optionally substituted $C_4$ to $C_{10}$ hydrocarbyloxy group;
$R^9$ and $R^{11}$ each are hydroxy; and
W is hydroxy and U is hydrogen, or W and U are both fluoro, or W and U together form an oxo moiety;

L is a group of formula (II):

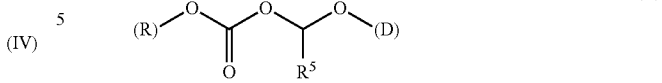

wherein:
$R^5$ is selected from hydrogen and $C_1$ to $C_6$ alkyl;
(R) indicates the point of attachment to R; and
(D) indicates the point of attachment to D; and
a monomer of formula (Va):

$$J\text{-}(Y\text{-}A)_n \qquad \text{Va}$$

wherein
J is an optionally substituted polymeric linker comprising a polyether, polyester, polyamide, polyurethane, or copolymer of any thereof,
n is an integer from 2 to 8;
Y comprises a chain of one or more groups selected from the group consisting of ether (—O—), ester, amide, carbonate, and carbamate; and
A may be the same or different at each occurrence and is a group comprising a terminal functional group comprising an alkyne or azide moiety, wherein said terminal functional group is complementary to the terminal functional group X of formula (IV).

6. The polymer-prostaglandin analogue of claim 5, wherein $R^5$ is methyl.

7. The polymer-prostaglandin conjugate of claim 5, wherein m is an integer from 0 to 6.

8. The polymer-prostaglandin analogue of claim 5, wherein Y of formula (Va) comprises an ester.

9. The polymer-prostaglandin analogue of claim 5, wherein J of formula (Va) comprises a polyether linker moiety derived from polyethylene glycol (PEG).

10. The polymer-prostaglandin analogue of claim 5, wherein J of formula (Va) comprises a polyethylene glycol having a molecular weight of from about 200 to about 10,000.

11. The polymer-prostaglandin analogue of claim 5, wherein n of formula (Va) is 3 or 4.

12. The polymer-prostaglandin analogue conjugate of claim 5, wherein Q is absent.

13. The polymer-prostaglandin conjugate of claim 5, wherein in the monomer of formula (IV) the prostaglandin analogue D is selected from the group consisting of:

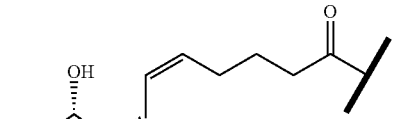

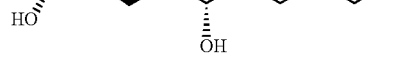
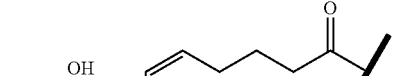

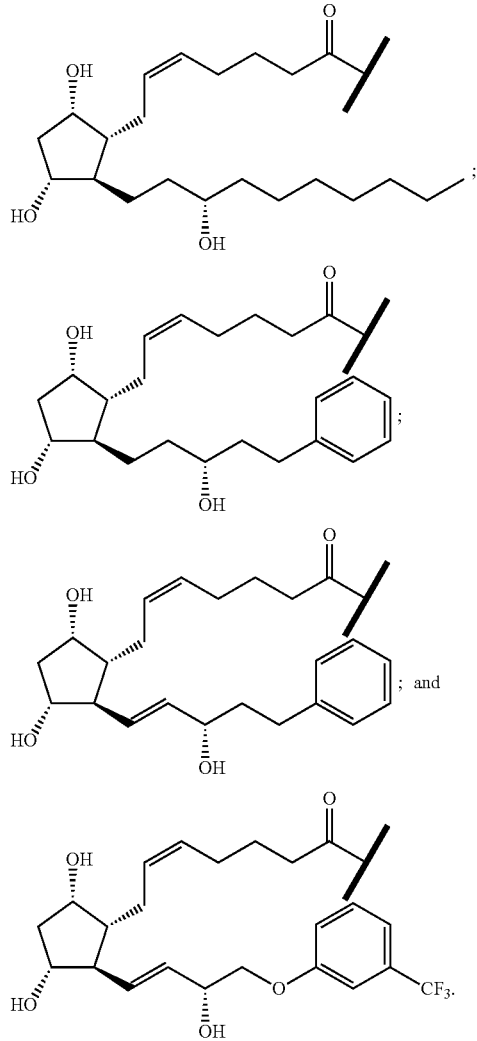

14. The polymer-prostaglandin analogue of claim 5, wherein formula (IV) is selected from the group consisting of:

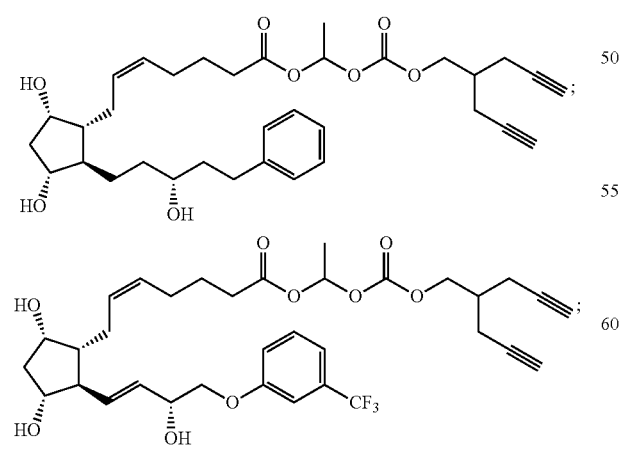

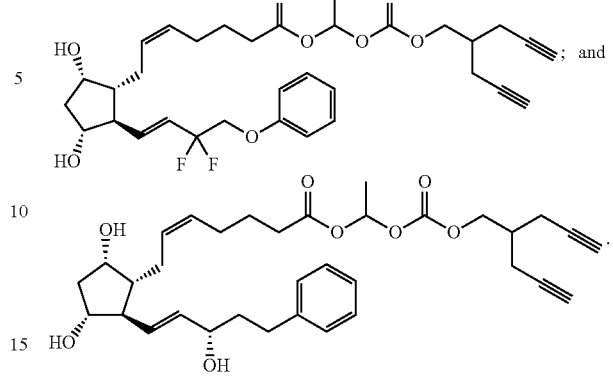

15. A monomer-prostaglandin conjugate, formula (IV):

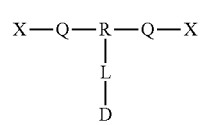

wherein:
X may be the same or different at each occurrence and represents a terminal functional group comprising an alkyne or an azide moiety;
Q is independently selected at each occurrence and may be present or absent and when present, represents a linking group selected from linking group Q of the following formulae Q-X, wherein X represents linkage to T and m is an integer from 0 to 10:

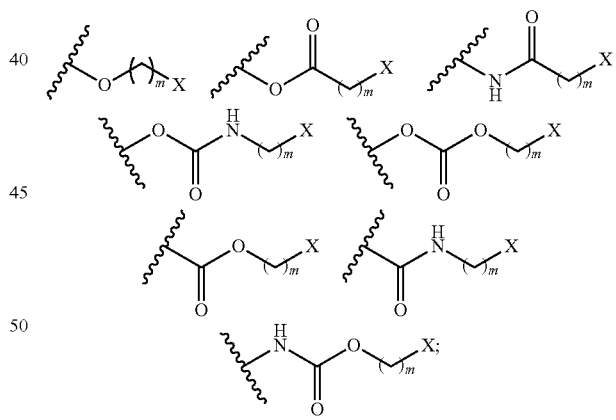

R is a linear or branched hydrocarbon;
L is a group of formula (II):

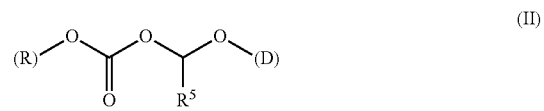

wherein:
$R^5$ is selected from hydrogen, methyl, ethyl, propyl, isopropyl, butyl, isobutyl, sec-butyl, and tert-butyl;

(R) indicates the point of attachment to R; and
(D) indicates the point of attachment to D; and
D is a prostaglandin analogue of formula (Xb):

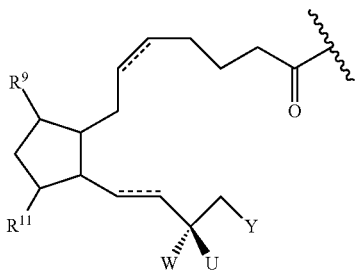

wherein:
  ⁓⁓⁓ represents the point of attachment of the prostaglandin analogue to L;
  each ----- independently represents a double or single bond;
  Y is an optionally substituted $C_4$ to $C_{10}$ hydrocarbyl group or optionally substituted $C_4$ to $C_{10}$ hydrocarbyloxy group;
  $R^9$ and $R^{11}$ each are hydroxy; and
  W is hydroxy and U is hydrogen, or W and U are both fluoro, or W and U together form an oxo moiety.

16. The monomer-prostaglandin conjugate of according to claim 15, wherein in formula (IV) the group Q is absent.

17. The monomer-prostaglandin conjugate of claim 15, wherein m is an integer from 0 to 6.

18. The monomer-prostaglandin conjugate of according to claim 15, wherein formula (IV) is selected from the group consisting of:

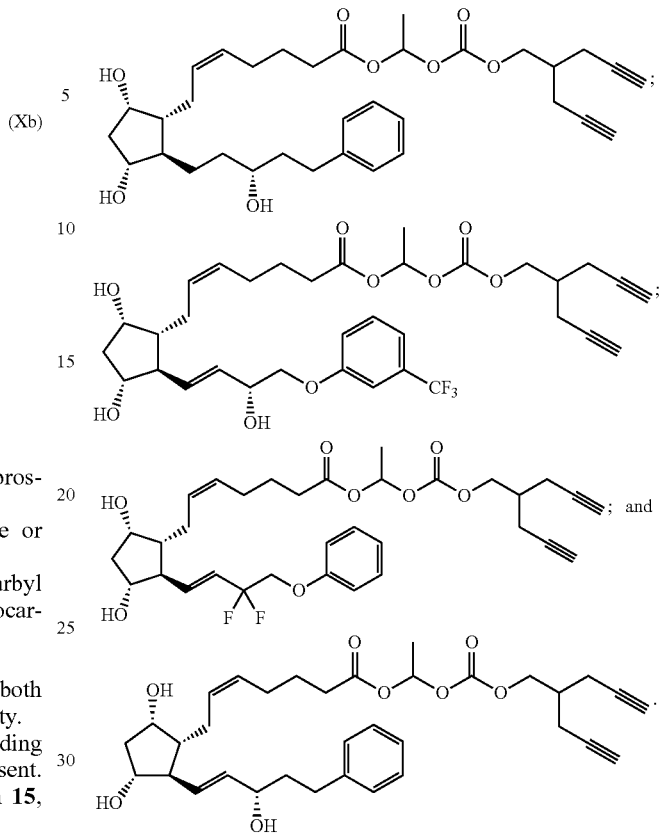

* * * * *